(12) United States Patent
Arico et al.

(10) Patent No.: US 10,864,262 B2
(45) Date of Patent: Dec. 15, 2020

(54) MUTANT BACTERIA FOR PRODUCTION OF GENERALIZED MODULES FOR MEMBRANE ANTIGENS

(71) Applicant: GlaxoSmithKline Biologicals s.a., Rixensart (BE)

(72) Inventors: Maria Arico, Poggibonsi (IT); Giuseppe Ercoli, Siena (IT); Nathalie Norais, Rapolano Terme (IT); Marco Soriani, Siena (IT); Chiara Tani, Siena (IT)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

(21) Appl. No.: 14/786,641

(22) PCT Filed: Apr. 24, 2014

(86) PCT No.: PCT/EP2014/058396
§ 371 (c)(1),
(2) Date: Oct. 23, 2015

(87) PCT Pub. No.: WO2014/174043
PCT Pub. Date: Oct. 30, 2014

(65) Prior Publication Data
US 2016/0067326 A1   Mar. 10, 2016

Related U.S. Application Data

(63) Continuation-in-part of application No. 14/396,881, filed as application No. PCT/EP2013/058459 on Apr. 24, 2013, now Pat. No. 10,279,026.

(30) Foreign Application Priority Data

Apr. 24, 2013  (WO) ............... PCT/EP2013/058459

(51) Int. Cl.
*A61K 39/102*    (2006.01)
*A61K 39/095*    (2006.01)
*C07K 14/285*    (2006.01)
*A61K 39/02*     (2006.01)
*C12R 1/21*      (2006.01)
*A61K 39/00*     (2006.01)

(52) U.S. Cl.
CPC .......... *A61K 39/102* (2013.01); *A61K 39/095* (2013.01); *A61K 39/099* (2013.01); *C07K 14/285* (2013.01); *C12R 1/21* (2013.01); *A61K 2039/55505* (2013.01); *A61K 2039/55566* (2013.01); *Y02A 50/30* (2018.01)

(58) Field of Classification Search
None
See application file for complete search history.

(56) References Cited

U.S. PATENT DOCUMENTS 7,749,518 B2 *   7/2010   Masignani ........... C07K 14/285
                                                       424/185.1

FOREIGN PATENT DOCUMENTS

WO     WO 2002 28889      4/2002
WO     WO 2010 092176     8/2010

OTHER PUBLICATIONS

Henry et al. Research Microbiology vol. 155, pp. 437-446, 2004.*
T. Uehara et al., "LytM-Domain Factors Are Required for Daughter Cell Separation and Rapid Ampicillin-Induced Lysis in *Escherichia coli*", Journal of Bacteriology, vol. 191, No. 16, Aug. 15, 2009, pp. 5094-5107.
Giuseppe Ercoli et al., "LytM Proteins of non-typeable Haemophilus influenzae are involved in cell separation, OMV production and host colonization", EMID 10th Annual Meeting, Couvent Royal De Saint-Maximin-La-Sainte-Baume, FR, Oct. 2-4, 2013, XP055119705.
Bernadac Alain et al., "*Escherichia coli* tol-pal mutants form outer membrane vesicles" Journal of Bacteriology, American Society for Microbiology, vol. 180, No. 18, Sep. 1, 1998, pp. 4872-4878.
Sebastian Poggio et al., "A protein critical for cell constriction in the Gram-negative bacterium Caulobacter crescentus localizes at the division site through its peptidoglycan-binding LysM domains", Molecular Microbiology, vol. 77, No. 1, May 24, 2010, pp. 74-89.
Ercoli, et al., *LytM proteins play a crucial role in cell separation, outer membrane composition, and pathogenesis in nontypeable Haemophilus influenza*, 2015 MBio 6(2):e02575 (10 total pages).

* cited by examiner

*Primary Examiner* — Jana A Hines
*Assistant Examiner* — Khatol S Shahnan Shah

(57) ABSTRACT

Gram-negative bacterial strains are generated by inactivating at least one LytM catalytic domain-containing protein, such as NT013, NT017 and NT022 of non typeable *H influenzae*. The vesicles from these strains are useful for vaccination.

7 Claims, 14 Drawing Sheets
Specification includes a Sequence Listing.

Figure 6
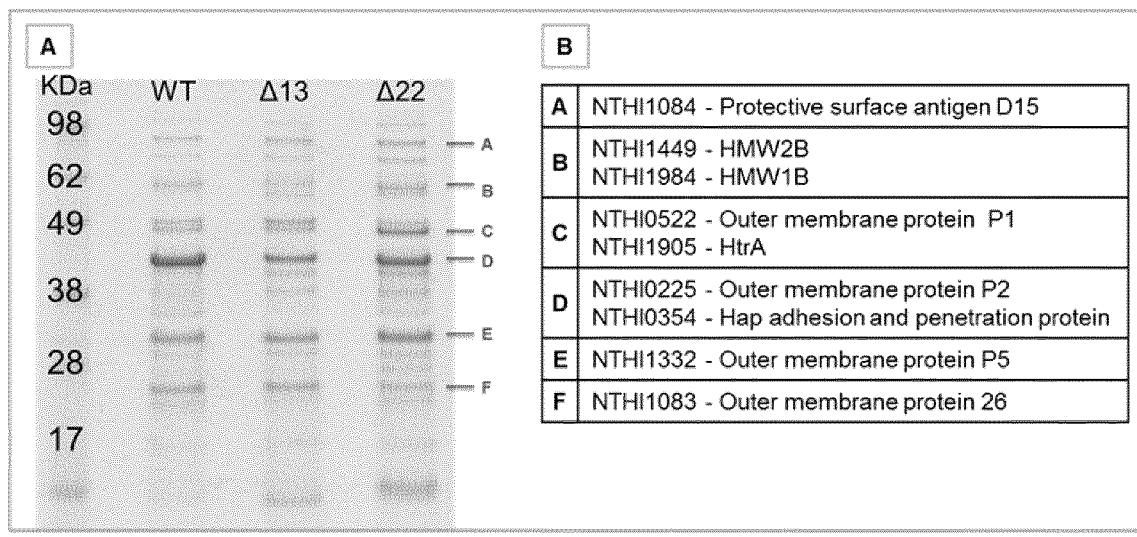
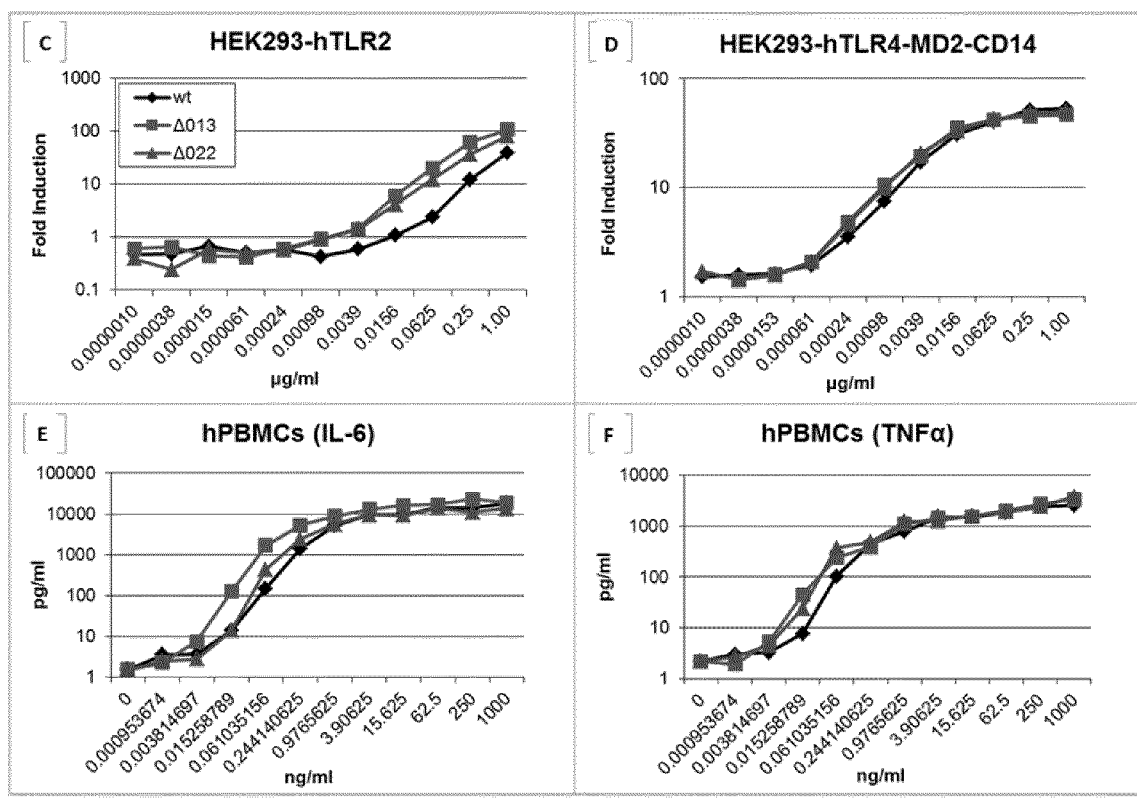

| | WT | ΔTolR | Δ17 | Δ13 | Δ22 |
|---|---|---|---|---|---|
| lipoprotein | | = | = | ++ | ++ |
| outer membrane | | - | = | -- | -- |
| periplasmic | | + | -- | + | + |
| cytoplasmic | | = | + | = | = |
| other | | = | + | = | = |

Bp W28 9G/129K                Bp W28 9G/129K ΔNlpD

Figure 16

```
N.meningitidis    --------MLKQTTLLAACTAVAALLGGCAT--QQPAPVIAGNSGMQDAPSSAVYNNPYG
B.pertussis       ------------------------------------------------------------
E.coli            MSAGSPKFTVRRIAA---LSLVSLWLAGCSDTSNPPAPVSSVNGNAPANT----------
NTHi              --------MKKSFLL---LPLSLVVLSACT--SNFPAPISDADGNLSPSVIQSVNGSNVG N.meningitidis    ----------------ATPYSPAP------AGDAPYVPPVQSAPVYTPPAYVPPSAPAVSG
B.pertussis       ------------------MLNG--------------QLQLTESQS-VAGA----------
E.coli            --------------NSGMLITPPPKMGTTSTAQQPQIQPVQQPQIQ--A-----------
NTHi              GAWQPEIQKNSLPTTGNMVTPQP-----------NFQPINQQPTMPTA------------
                                                    .                    .:.
N.meningitidis    TYVPSYAPVDINAATHTIVRGDTVYNISKRYHISQDDFRAWNGMTDNTLSIGQIVKVKPA
B.pertussis       SAAAASRPV-------------------------------LWAGVLAIALLAGCAS----
E.coli            TQQPQIQPVQ-----------------------------------------PVA-QQP-
NTHi              PAQPPAFQPSPKT-----VVSA-----------------PTVQTKTV-TKTVADCVD-GQH-
                                *
N.meningitidis    GYAAPKAAAVKSRPAVPAAAQPPVQSAPVDINAATHTIVRGDTVYNISKRYHISQDDFRA
B.pertussis       --KGPRAPVV----DL--TGQP----GASGPTDGSYVVKPGDTLYKIARANNVDIENLKR
E.coli            -VQMENGRIV----YNRQYGNI----PKGSYSGSTYTVKKGDTLFYIAWITGNDFRDLAQ
NTHi              -INIPRNPNT----NVPDYSKI----SKGSYKGNTYKVNKGDTMFLIAYLAGIDVKELAA
                          .          .:         . ::  : ***::  *:      .   ::
N.meningitidis    WNGMTD-NMLSIGQIVKVKPAGYAAPKTAAVE---------------SRPAVPAAVQTPVK
B.pertussis       WNNLTDPNQISVGQVLRLSSSGAGGAQTTPVTSSKPQPKPLDQGSAET------------
E.coli            RNNIQAPYALNVGQTLQVGNASGTPITGG---NAITQADAAEQGVVIKPAQNSTVAVASQ
NTHi              LNNLSEPYNLSLGQVLKISNCSTKTVTTT---VSVKQP-----------AVITSTATPVK
                   *  :     :.:**  :::   ..
N.meningitidis    PAAQPPVQSAPQPA-----------APAAENKAVPA-----------PAPQSPAASPSG
B.pertussis       P-------AGGMEAGAGGETGGATTPPAAT----------------------VPDPKPAR
E.coli            PTITYSESSGEQSA---NKML-PNNKPTATTVTAPVTVP---------TASTTEPTVSST
NTHi              PAVTYTPGANGTQIGSDGTIIGPIKSEAGTSPSVPVATSSTQVTSSVNNANSTPINSNVV
                  *          :                  :.
N.meningitidis    TRSVGGIVWQRPTQGKVVADFGGN---NKGVDIAGNAGQPVLAAADGKVVYAGSGLRGYG
B.pertussis       AADAAVINWGWPANGAILQTFNSN---TKGIDLAGSLGDPVIAAADGKVMYSGNGVRGLG
E.coli            STSTPISTWRWPTEGKVIETFGASEGGNKGIDIAGSKGQAIIATADGRVVYAGNALRGYG
NTHi              APIASHVVWQWPTSGNIIQGFSSTDGGNKGIDISGSRGQAVKAAAAGRIVYAGNALRGYG
                   :  .   *  *:.*  ::   *  ..  .**:*::*, *: : *:*  *:::*:*.. :** *
N.meningitidis    NLVIIQHNSSFLTAYGHNQKLLVGEGQQVKRGQQVALMGNTDASRTQLHFEVRQNGKPVN
B.pertussis       NLIINHQNGFITAYAHNRALLVKTGQNVKRGAKIAEIGETDTTSPRLHFEIRRQGTPVD
E.coli            NLIIKHNDDYLSAYAHNDTMLVREQQEVKAGQKIATMGSTGTSSTRLHFEIRYKGKSVN
NTHi              NLIIKHNDDFLSAYAHNDKILVADQQEVKAGQDIAKMGSSGTNTVKLHFEIRYKGKSVD
                  **:**:*:.  :::**.**  :**    *:** *  :*  *..: :.    :****:*   :*.  *:
N.meningitidis    PNSYIAF-
B.pertussis       PMQYLPPR
E.coli            PLRYLPQR
NTHi              PVRYLPRH
                   *  *:
```

N.meningitidis 0.34342
B.pertussis 0.29703
E.coli 0.27175
NTHi 0.2758

Figure 17

```
E.coli          MQ--------QIARSVALAFN----NLPRPHRVMLGSLTVLT--LAVAV-WRPYVYHRDA
NTHi            ----------MPVQHVKLARD----RRKKRTYIKVGVFFVAILLILTGI-LLTIKDKSEE
N.meningitidis  ---------------MAVF---PLSAKHRKYA--LRALAVSIIL--VSAAYIAS------
B.pertussis     MNRGPNSLVRSFKRKVAALFAPPVEPTSRGGALLRRTLTVSALGLFAGAAALGM------
                                      :  : *   ..

E.coli          TPIVKTIELEQ--------N-EIRSLLPEAS-------------EPIDQ---AAQEDEAIP
NTHi            NPIFSTSDSGEYHELNTSPNKNSTALQPDEDATSYDDELQAKDDEVDEVKLSSDDLGTLP
N.meningitidis  -----T-----------------------------------------------ERTERVRP
B.pertussis     ---VQQ-----------------------------------------------PDRSELPP
                                                                          *

E.coli          QD---EL------D---DKIAGEAGVHEYVVSTGDTLSSILNQYGIDMGDITQLAAA---
NTHi            QHAQDALNGLLDAA---DQAIRITDQFSYTVTEGDTLKDVLVLSGLDDSSVQPLIKL---
N.meningitidis  QRVEQNLPPLSWGGSG----VQTAYWVQEAVQPGDSLADVLARSGMARDEIARITEKYGG
B.pertussis     LRLIDSVLPLEAGQMQVSDASNAPYISETRIRAGDTLAAVLQRLDIDSPRLQNFLTHDAS
                    :       .   **:*  :*     :    :

E.coli          DKELRNLKIGQQLSWTLTADGELQRLTWEVSRRET-------RTYDRTAANGFK-MTSEM
NTHi            DPELAHLKAGQQFYWILNKNDNLEYLNWLVSEKEE-------RIYERLEDGKFK-RQVIE
N.meningitidis  EADLRHLRADQSVHVLVGGDGGAREVQFFT---------------DEDGERNLVALEK
B.pertussis     ARSIYKLYPGRSVQAATNENGDLVWLRYIHTPGNESGGQVVTRLLHVAPDGANGYKAEEV
                 .:  .*    :..       :        : :

E.coli          QQGEWVNNLL------KGTV-----GGSFVASARNAGLTSAEVSAVIKAMQWQM-DFRKL
NTHi            KKSIWRKEVL------KGEI-----QNSLNSSLREQGLDTRQISQLSNALQWQV-SLRKL
N.meningitidis  KGGIWRRSASEADMKVLPTLRSVVVKTSARGSLARAEVPVEIRESLSGIFAGRF-SLDGL
B.pertussis     TQGTE-----QQTRVAVGTI-----RSSLFGATDAAGIPDSVTMQMADILSSKIDFLRDL
                .        :     *   .:   :         :    : :.   :   *

E.coli          KKGDEFAVLMSREMLDGKR-EQSQLLGVRLRSEGKDYYAIR--------AEDGKFYDRNGT
NTHi            KKGTQFAILVSREYLGDKLTGQGNVEALRISSGGKNYYAVQ--------AANGRYYNQQGE
N.meningitidis  KEGDAVRLMYDSLYFHGQQVAAGDILAAEVVKGGTRHQAFYYRSDKEGGGGGNYYDEDGK
B.pertussis     RQGDQFRVVYEVRTHEGRYAGAGRVQALEFINGDKTYNAVWFSPD---GKSGSYYDFDGT
                ::*    .::   .       :   . :  ..   .: *.      . * :*: :*

E.coli          GL--AKGFLRFPTAKQFRISSNFNPRRTNPVTGRVAPHRGVDFAMPQGTPVLSVGDGEVV
NTHi            TL--GKGFARYPLQRQARVSSPFNPNRRHPVTGRVRPHKGVDFSVSQGTPVIAPADGTVE
N.meningitidis  VLQEKGGFNIEPL-VYTRISSPFGY-RMHPILHTWRLHTGIDYAAPQGTPVRASADGVIT
B.pertussis     SL--RGAFLRTAL-KFSRISSTFGM-RMHPIHKTWTGHKGVDYAAPTGTPIHATADGTVE
                 *     .*        *:** *   * .*:       * *:*::   ***: : .** :

E.coli          -VAKRSGAAGYYVAIRHGRSYTTRYMHLRKIL--VKPGQKVKRGDRIALSGNTGRSTGPH
NTHi            KVAYQAGGAGRYVMLRHGREYQTVYMHLSKSL--VKAGQTVKKGERIALSGNTGISTGPH
N.meningitidis  -FKGRKGGYGNAVMIRHANGVETLYAHLSAFSQA---EGNVRGGEVIGFVGSTGRSTGPH
B.pertussis     -FAGWQNGYGNVVIIKHHGKYSTLYAHQSRIASGLKKGQKIAQGELVGYVGSTGWATGPH
                 .       *  *  ::*    * * *            .: *: :.  *.** :****

E.coli          LHYEVWINQQAVNPLTAKLPRTE-GLTGSDRREFLAQAKEIVPQLRFD---------
NTHi            LHYEFRINGRAVNPLTVKLPGTSSGMTSAERKQFLVRVREAEKMLKP---------
N.meningitidis  LHYEARINGQPVNPVSVALPTPE-LTQA-DKAAFAAQKQKADALLARLRGIPVTVSQSD-
B.pertussis     LHYEFRVNNQPIDPLAVDLPVAR-KLEPAELRAFTQAVQPYKQQIKLLTEFQQTLPEGSA
                ****  :*  :  ::*::. **       :   *      :

E.coli          -----
NTHi            -----
N.meningitidis  -----
B.pertussis     TVASR
```

E.coli 0.29785
NTHi 0.28109
N.meningitidis 0.33229
B.pertussis 0.34241

Figure 18

```
N.meningitidis    ---------------MRYKPLLLALMLVFSTPAVAAHDAAHNRSAEVKKQTKNKKEQP
B.pertussis       ------------------MRVAAGLLVWAAVAVAPPAAWA-VSDLAGRQSE-------
E.coli            MTRAVKPRRFAI---RPIIYASVLSAGVLLCAFSAHAD---------------------
NTHi              ------MLRFGVNQKTSLLLTALLSCGLLIFSPVS------------------------
                           :  .:*:  :  :

N.meningitidis    EAAEGKKEKGKNGAVKDKKTGGKEAAKEGKESKKTAKNRKEAEKEATSRQSARKGREGDK
B.pertussis       ------------------------------------------------------------
E.coli            ------------------------------------------------------------
NTHi              ------------------------------------------------------------

N.meningitidis    KSKAEHKKAHGKPVSGSKEKNAKTQPENKQGKKEAKGQGNPRKGGKAEKDTVSANKKVRS
B.pertussis       ----------------------------------------AERQQAALRDRIDA------
E.coli            ------------------------------------------------ERDQLKS------
NTHi              -------------------------------------------------QSSDLNQ-----
                                                              . :.

N.meningitidis    DKNGKAVKQDKKYREEKNAKTDSDELKAAVAAATNDVENKKALLKQSEGMLLHVSNSLKQ
B.pertussis       -------LQKEIDTRE------------AARKEAADALKESESAISRINLRLRELG-----
E.coli            -------IQADIAAKERAVRQ-----KQQQRASLLAQLKKQEEAISEATRKLRETQNTLNQ
NTHi              -------IQKQIKQQESKIEK-----QKREQAKLQANLKKHESKINTVEGELLETEISLKE
                         ::  :    :*                  :::  :  :.       *  .

N.meningitidis    LQEERIRQERIRQARGNLASVNRKQREAWDKFQKLNTELNRLKTEVAA-------TKAQI
B.pertussis       --E-------------------AS--------RKAEAELAGLEKQVVAQQAVLQKRRAEL
E.coli            LNK-------------------QI--------DEMNASIAKLEQQKAA-------QERSL
NTHi              IRK-------------------QI--------ADADKQFKQLEKQERE-------QKARL
                    :                . .  .: *:  :                         . .

N.meningitidis    SRFVSGNYKNSQPNAVALFLKNAEPGQKNRFLRYTRYVNASNREVVKDLEKQQKALAVQE
B.pertussis       ADQLRTQYTSGLSPWT-ALLSGDDPQQLGRNLGYLDYVSRARAQAVHALREDIARLAALQ
E.coli            AAQLDAAFRQGEHTGIQLILSGEESQRGQRLQAYFGYLNQARQETIAQLKQTREEVAMQR
NTHi              AKQMDIIYRSGINPSLIERMFAQDPTKAERMKVYYQHLNQVRIEMIDNLKATQAQIAVQK
                   :     :     ..     :    :   : *   *  ::.  .: :  *.    :*  .

N.meningitidis    QKINNELARLKKIQANVQSLLKKQGVTDAAEQ--------TESRRQNAKIAKDARKLLEQK
B.pertussis       GQADARRD-------DIQTLVAETSSQKAALVEQQKTRATLLAKLEGQIAAQRAEAGKLG
E.coli            AELEEKQS-------EQQTLLYEQRAQQAKLTQALNERKKTLAGLESSIQQGQQQLSELR
NTHi              EAILAQQK-------NHRNQLSTQKKQQQALQKAQQEHQSTLNELNKNLALDQDKLNALK
                   .           : :.:.               .         :  .: :

N.meningitidis    GNEQQLNKLLSNLEKKKAEHRIQDA-------------------------EAKRK
B.pertussis       RDDQRLSHLIDDLGSAIARQAEEEDARRRAAEEARRKEEEARQAEAARRAEAARQQEAARQ
E.coli            ANESRLRN-----------------------------------------------SIARA
NTHi              ANEQALRQ-----------------------------------------------EIQRA
                   ::. * .                                                . *

N.meningitidis    LAEA-------------------RLAAAEKARKEAAQQKA-----------------
B.pertussis       AAAAREADARRQAETARQAQQARDAEARDAAAAREQAEAAARQGRGPVALADPDAAGLRQ
E.coli            EAAAKA-------------RAEREAREAQAVRDR-QKEA-----------------
NTHi              EQAARE---------------QEKRE---REALAQRQKAEE---------------
                      *                      *   : : *

N.meningitidis    ---------------EARRAE-MSNLTAEDRNIQAPSVMGIGSADGFSRMQGRLKKPVDG
B.pertussis       VEGGRLVDPQAAPPRETRPAARAEPAEPAPREAAPARTASAAPVGGGNGLRRGLPMPVRG
E.coli            -------------------TRK---GTTYKPTESE-----KSLMSRTGGLGAPRGQAFWPVRG
NTHi              -----------------KRT---SKPYQPTVQE-----RQLINSTSGLGAAKKQYSLPVSG
                                    *          :          . *     :       ** *

N.meningitidis    VPTGLFGQNRSGGDIWKGVEYSTAP-ATVESIAPGTVSYADELDGYGKVVVVDHGENYIS
B.pertussis       TIQGRFGVDRPDGGVWRGLVLRTAEGTPVKVVAPGTVVYAEWLRGFGNLIIVDHGQQYLT
E.coli            PTLHRYGEQLQGELRWKGMVIGASEGTEVKAIADGRVILADWLQGYGLVVVVEHGKGDMS
NTHi              SILHTFGSIQAGEVRWKGMVIGASAGTPVKAIAAGRVILAGYLNGYGYMVIVKHGETDLS
                   :*      *:*:..   :  :* :* * *   *:* *.* .* :** *: ::

N.meningitidis    IYAGLSEISVGKGYMVAAGSKIGSSGSL-PDGEEGLYLQIRYQGQVLNPSSWIR-
B.pertussis       VYAYNQSLLKRVGDRVAAGDTIATVGATGGQVESGLYFEIRHRGAPVDPAQWLAQ
E.coli            LYGYNQSALVSVGSQVRAGQPIALVGSSGGQGRPSLYFEIRRQGQAVNPQPWLGR
NTHi              LYGFNQAVSVKVGQLVSAGQVIAQVGNTGEISRSALYFGISRKGTPVNPAGWVR-
                   :*. .      *  * **. *. *       . .**: *  :*    ::* *:
```

N.meningitidis 0.39328
B.pertussis 0.32748
E.coli 0.29673
NTHi 0.30918

SEQUENCE LISTING

<160> NUMBER OF SEQ ID NOS: 87

<210> SEQ ID NO 1
<211> LENGTH: 475
<212> TYPE: PRT
<213> ORGANISM: Haemophilus influenzae

<400> SEQUENCE: 1

```
Met Pro Val Gln His Val Lys Leu Ala Arg Asp Arg Lys Lys Arg
1               5                   10                  15

Thr Tyr Ile Lys Val Gly Val Phe Phe Val Ala Ile Leu Leu Ile Leu
                20                  25                  30

Thr Gly Ile Leu Leu Thr Ile Lys Asp Lys Ser Glu Glu Asn Pro Ile
                35                  40                  45

Phe Ser Thr Ser Asp Ser Gly Glu Tyr His Glu Leu Asn Thr Ser Pro
    50                  55                  60

Asn Lys Asn Ser Thr Ala Leu Gln Pro Asp Glu Asp Ala Thr Ser Tyr
65                  70                  75                  80

Asp Asp Glu Leu Gln Ala Lys Asp Asp Glu Val Asp Glu Val Lys Leu
                85                  90                  95

Ser Ser Asp Asp Leu Gly Thr Leu Pro Gln His Ala Gln Asp Ala Leu
                100                 105                 110

Asn Gly Leu Leu Asp Ala Ala Asp Gln Ala Ile Arg Ile Thr Asp Gln
                115                 120                 125

Phe Ser Tyr Thr Val Thr Glu Gly Asp Thr Leu Lys Asp Val Leu Val
    130                 135                 140

Leu Ser Gly Leu Asp Asp Ser Ser Val Gln Pro Leu Ile Lys Leu Asp
145                 150                 155                 160

Pro Glu Leu Ala His Leu Lys Ala Gly Gln Gln Phe Tyr Trp Ile Leu
                165                 170                 175

Asn Lys Asn Asp Asn Leu Glu Tyr Leu Asn Trp Leu Val Ser Glu Lys
                180                 185                 190

Glu Glu Arg Ile Tyr Glu Arg Leu Glu Asp Gly Lys Phe Lys Arg Gln
            195                 200                 205

Val Ile Glu Lys Lys Ser Ile Trp Arg Lys Glu Val Leu Lys Gly Glu
    210                 215                 220

Ile Gln Asn Ser Leu Asn Ser Ser Leu Arg Glu Gln Gly Leu Asp Thr
225                 230                 235                 240

Arg Gln Ile Ser Gln Leu Ser Asn Ala Leu Gln Trp Gln Val Ser Leu
                245                 250                 255

Arg Lys Leu Lys Lys Gly Thr Gln Phe Ala Ile Leu Val Ser Arg Glu
            260                 265                 270

Tyr Leu Gly Asp Lys Leu Thr Gly Gln Gly Asn Val Glu Ala Leu Arg
    275                 280                 285

Ile Ser Ser Gly Gly Lys Asn Tyr Tyr Ala Val Gln Ala Ala Asn Gly
    290                 295                 300

Arg Tyr Tyr Asn Gln Gly Glu Thr Leu Gly Lys Gly Phe Ala Arg
305                 310                 315                 320

Tyr Pro Leu Gln Arg Gln Ala Arg Val Ser Ser Pro Phe Asn Pro Asn
                325                 330                 335
```

```
Arg Arg His Pro Val Thr Gly Arg Val Arg Pro His Lys Gly Val Asp
            340                 345                 350

Phe Ser Val Ser Gln Gly Thr Pro Val Ile Ala Pro Ala Asp Gly Thr
        355                 360                 365

Val Glu Lys Val Ala Tyr Gln Ala Gly Ala Gly Arg Tyr Val Met
370                 375                 380

Leu Arg His Gly Arg Glu Tyr Gln Thr Val Tyr Met His Leu Ser Lys
385                 390                 395                 400

Ser Leu Val Lys Ala Gly Gln Thr Val Lys Lys Gly Glu Arg Ile Ala
                405                 410                 415

Leu Ser Gly Asn Thr Gly Ile Ser Thr Gly Pro His Leu His Tyr Glu
            420                 425                 430

Phe Arg Ile Asn Gly Arg Ala Val Asn Pro Leu Thr Val Lys Leu Pro
        435                 440                 445

Gly Thr Ser Ser Gly Met Thr Ser Ala Glu Arg Lys Gln Phe Leu Val
    450                 455                 460

Arg Val Arg Glu Ala Glu Lys Met Leu Lys Pro
465                 470                 475

<210> SEQ ID NO 2
<211> LENGTH: 97
<212> TYPE: PRT
<213> ORGANISM: Haemophilus influenzae

<400> SEQUENCE: 2

Arg Pro His Lys Gly Val Asp Phe Ser Val Ser Gln Gly Thr Pro Val
1               5                   10                  15

Ile Ala Pro Ala Asp Gly Thr Val Glu Lys Val Ala Tyr Gln Ala Gly
                20                  25                  30

Gly Ala Gly Arg Tyr Val Met Leu Arg His Gly Arg Glu Tyr Gln Thr
            35                  40                  45

Val Tyr Met His Leu Ser Lys Ser Leu Val Lys Ala Gly Gln Thr Val
    50                  55                  60

Lys Lys Gly Glu Arg Ile Ala Leu Ser Gly Asn Thr Gly Ile Ser Thr
65                  70                  75                  80

Gly Pro His Leu His Tyr Glu Phe Arg Ile Asn Gly Arg Ala Val Asn
                85                  90                  95

Pro

<210> SEQ ID NO 3
<211> LENGTH: 410
<212> TYPE: PRT
<213> ORGANISM: Haemophilus influenzae

<400> SEQUENCE: 3

Met Leu Arg Phe Gly Val Asn Gln Lys Thr Ser Leu Leu Thr Ala
1               5                   10                  15

Leu Leu Ser Cys Gly Leu Leu Ile Phe Ser Pro Val Ser Gln Ser Ser
                20                  25                  30

Asp Leu Asn Gln Ile Gln Lys Gln Ile Lys Gln Gln Glu Ser Lys Ile
            35                  40                  45

Glu Lys Gln Lys Arg Glu Gln Ala Lys Leu Gln Ala Asn Leu Lys Lys
        50                  55                  60

His Glu Ser Lys Ile Asn Thr Val Glu Gly Glu Leu Leu Glu Thr Glu
65                  70                  75                  80
```

```
Ile Ser Leu Lys Glu Ile Arg Lys Gln Ile Ala Asp Ala Asp Lys Gln
                85                  90                  95
Phe Lys Gln Leu Glu Lys Gln Glu Arg Glu Gln Lys Ala Arg Leu Ala
            100                 105                 110
Lys Gln Met Asp Ile Ile Tyr Arg Ser Gly Ile Asn Pro Ser Leu Ile
        115                 120                 125
Glu Arg Met Phe Ala Gln Asp Pro Thr Lys Ala Glu Arg Met Lys Val
    130                 135                 140
Tyr Tyr Gln His Leu Asn Gln Val Arg Ile Glu Met Ile Asp Asn Leu
145                 150                 155                 160
Lys Ala Thr Gln Ala Gln Ile Ala Val Gln Lys Glu Ala Ile Leu Ala
                165                 170                 175
Gln Gln Lys Asn His Arg Asn Gln Leu Ser Thr Gln Lys Lys Gln Gln
            180                 185                 190
Gln Ala Leu Gln Lys Ala Gln Gln Glu His Gln Ser Thr Leu Asn Glu
        195                 200                 205
Leu Asn Lys Asn Leu Ala Leu Asp Gln Asp Lys Leu Asn Ala Leu Lys
    210                 215                 220
Ala Asn Glu Gln Ala Leu Arg Gln Glu Ile Gln Arg Ala Glu Gln Ala
225                 230                 235                 240
Ala Arg Glu Gln Glu Lys Arg Glu Arg Glu Ala Leu Ala Gln Arg Gln
                245                 250                 255
Lys Ala Glu Glu Lys Arg Thr Ser Lys Pro Tyr Gln Pro Thr Val Gln
            260                 265                 270
Glu Arg Gln Leu Ile Asn Ser Thr Ser Gly Leu Gly Ala Ala Lys Lys
        275                 280                 285
Gln Tyr Ser Leu Pro Val Ser Gly Ser Ile Leu His Thr Phe Gly Ser
    290                 295                 300
Ile Gln Ala Gly Glu Val Arg Trp Lys Gly Met Val Ile Gly Ala Ser
305                 310                 315                 320
Ala Gly Thr Pro Val Lys Ala Ile Ala Ala Gly Arg Val Ile Leu Ala
                325                 330                 335
Gly Tyr Leu Asn Gly Tyr Gly Tyr Met Val Ile Val Lys His Gly Glu
            340                 345                 350
Thr Asp Leu Ser Leu Tyr Gly Phe Asn Gln Ala Val Ser Val Lys Val
        355                 360                 365
Gly Gln Leu Val Ser Ala Gly Gln Val Ile Ala Gln Val Gly Asn Thr
    370                 375                 380
Gly Glu Ile Ser Arg Ser Ala Leu Tyr Phe Gly Ile Ser Arg Lys Gly
385                 390                 395                 400
Thr Pro Val Asn Pro Ala Gly Trp Val Arg
                405                 410

<210> SEQ ID NO 4
<211> LENGTH: 96
<212> TYPE: PRT
<213> ORGANISM: Haemophilus influenzae

<400> SEQUENCE: 4

Val Arg Trp Lys Gly Met Val Ile Gly Ala Ser Ala Gly Thr Pro Val
1               5                   10                  15
Lys Ala Ile Ala Ala Gly Arg Val Ile Leu Ala Gly Tyr Leu Asn Gly
            20                  25                  30
Tyr Gly Tyr Met Val Ile Val Lys His Gly Glu Thr Asp Leu Ser Leu
        35                  40                  45
```

```
Tyr Gly Phe Asn Gln Ala Val Ser Val Lys Val Gly Gln Leu Val Ser
            50                  55                  60

Ala Gly Gln Val Ile Ala Gln Val Gly Asn Thr Gly Glu Ile Ser Arg
 65                  70                  75                  80

Ser Ala Leu Tyr Phe Gly Ile Ser Arg Lys Gly Thr Pro Val Asn Pro
                85                  90                  95

<210> SEQ ID NO 5
<211> LENGTH: 405
<212> TYPE: PRT
<213> ORGANISM: Haemophilus influenzae

<400> SEQUENCE: 5

Met Lys Lys Ser Phe Leu Leu Pro Leu Ser Leu Val Val Leu Ser
 1               5                  10                  15

Ala Cys Thr Ser Asn Phe Pro Ala Pro Ile Ser Asp Ala Asp Gly Asn
                20                  25                  30

Leu Ser Pro Ser Val Ile Gln Ser Val Asn Gly Ser Asn Val Gly Gly
            35                  40                  45

Ala Trp Gln Pro Glu Ile Gln Lys Asn Ser Leu Pro Thr Thr Gly Asn
 50                  55                  60

Met Val Thr Pro Gln Pro Asn Phe Gln Pro Ile Asn Gln Gln Pro Thr
 65                  70                  75                  80

Met Pro Thr Ala Pro Ala Gln Pro Ala Phe Gln Pro Ser Pro Lys Thr
                85                  90                  95

Val Val Ser Ala Pro Thr Val Gln Thr Lys Thr Val Thr Lys Thr Val
            100                 105                 110

Ala Asp Cys Val Asp Gly Gln His Ile Asn Ile Pro Arg Asn Pro Asn
            115                 120                 125

Thr Asn Val Pro Asp Tyr Ser Lys Ile Ser Lys Gly Ser Tyr Lys Gly
130                 135                 140

Asn Thr Tyr Lys Val Asn Lys Gly Asp Thr Met Phe Leu Ile Ala Tyr
145                 150                 155                 160

Leu Ala Gly Ile Asp Val Lys Glu Leu Ala Ala Leu Asn Asn Leu Ser
                165                 170                 175

Glu Pro Tyr Asn Leu Ser Leu Gly Gln Val Leu Lys Ile Ser Asn Cys
            180                 185                 190

Ser Thr Lys Thr Val Thr Thr Thr Val Ser Val Lys Gln Pro Ala Val
            195                 200                 205

Thr Thr Ser Thr Ala Thr Pro Val Lys Pro Ala Val Thr Tyr Thr Pro
210                 215                 220

Gly Ala Asn Gly Thr Gln Ile Gly Ser Asp Gly Thr Ile Ile Gly Pro
225                 230                 235                 240

Ile Lys Ser Glu Ala Gly Thr Ser Pro Ser Val Pro Val Ala Thr Ser
                245                 250                 255

Ser Thr Gln Val Thr Ser Ser Val Asn Asn Ala Asn Ser Thr Pro Ile
            260                 265                 270

Asn Ser Asn Val Val Ala Pro Ile Ala Ser His Val Val Trp Gln Trp
        275                 280                 285

Pro Thr Ser Gly Asn Ile Ile Gln Gly Phe Ser Ser Thr Asp Gly Gly
            290                 295                 300

Asn Lys Gly Ile Asp Ile Ser Gly Ser Arg Gly Gln Ala Val Lys Ala
305                 310                 315                 320

Ala Ala Ala Gly Arg Ile Val Tyr Ala Gly Asn Ala Leu Arg Gly Tyr
```

```
                    325                 330                 335
Gly Asn Leu Ile Ile Ile Lys His Asn Asp Asp Phe Leu Ser Ala Tyr
                340                 345                 350

Ala His Asn Asp Lys Ile Leu Val Ala Asp Gln Gln Glu Val Lys Ala
            355                 360                 365

Gly Gln Asp Ile Ala Lys Met Gly Ser Ser Gly Thr Asn Thr Val Lys
        370                 375                 380

Leu His Phe Glu Ile Arg Tyr Lys Gly Lys Ser Val Asp Pro Val Arg
385                 390                 395                 400

Tyr Leu Pro Arg His
                405

<210> SEQ ID NO 6
<211> LENGTH: 96
<212> TYPE: PRT
<213> ORGANISM: Haemophilus influenzae

<400> SEQUENCE: 6

Gly Gly Asn Lys Gly Ile Asp Ile Ser Gly Ser Arg Gly Gln Ala Val
1               5                   10                  15

Lys Ala Ala Ala Gly Arg Ile Val Tyr Ala Gly Asn Ala Leu Arg
            20                  25                  30

Gly Tyr Gly Asn Leu Ile Ile Ile Lys His Asn Asp Asp Phe Leu Ser
        35                  40                  45

Ala Tyr Ala His Asn Asp Lys Ile Leu Val Ala Asp Gln Gln Glu Val
    50                  55                  60

Lys Ala Gly Gln Asp Ile Ala Lys Met Gly Ser Ser Gly Thr Asn Thr
65                  70                  75                  80

Val Lys Leu His Phe Glu Ile Arg Tyr Lys Gly Lys Ser Val Asp Pro
                85                  90                  95

<210> SEQ ID NO 7
<211> LENGTH: 440
<212> TYPE: PRT
<213> ORGANISM: Escherichia coli

<400> SEQUENCE: 7

Met Gln Gln Ile Ala Arg Ser Val Ala Leu Ala Phe Asn Asn Leu Pro
1               5                   10                  15

Arg Pro His Arg Val Met Leu Gly Ser Leu Thr Val Leu Thr Leu Ala
            20                  25                  30

Val Ala Val Trp Arg Pro Tyr Val Tyr His Arg Asp Ala Thr Pro Ile
        35                  40                  45

Val Lys Thr Ile Glu Leu Glu Gln Asn Glu Ile Arg Ser Leu Leu Pro
    50                  55                  60

Glu Ala Ser Glu Pro Ile Asp Gln Ala Gln Glu Asp Glu Ala Ile
65                  70                  75                  80

Pro Gln Asp Glu Leu Asp Asp Lys Ile Ala Gly Glu Ala Gly Val His
                85                  90                  95

Glu Tyr Val Val Ser Thr Gly Asp Thr Leu Ser Ser Ile Leu Asn Gln
            100                 105                 110

Tyr Gly Ile Asp Met Gly Asp Ile Thr Gln Leu Ala Ala Ala Asp Lys
        115                 120                 125

Glu Leu Arg Asn Leu Lys Ile Gly Gln Gln Leu Ser Trp Thr Leu Thr
    130                 135                 140

Ala Asp Gly Glu Leu Gln Arg Leu Thr Trp Glu Val Ser Arg Arg Glu
```

```
              145                 150                 155                 160
        Thr Arg Thr Tyr Asp Arg Thr Ala Ala Asn Gly Phe Lys Met Thr Ser
                            165                 170                 175

Glu Met Gln Gln Gly Glu Trp Val Asn Asn Leu Leu Lys Gly Thr Val
                            180                 185                 190

Gly Gly Ser Phe Val Ala Ser Ala Arg Asn Ala Gly Leu Thr Ser Ala
                            195                 200                 205

Glu Val Ser Ala Val Ile Lys Ala Met Gln Trp Gln Met Asp Phe Arg
                            210                 215                 220

Lys Leu Lys Lys Gly Asp Glu Phe Ala Val Leu Met Ser Arg Glu Met
        225                 230                 235                 240

Leu Asp Gly Lys Arg Glu Gln Ser Gln Leu Leu Gly Val Arg Leu Arg
                            245                 250                 255

Ser Glu Gly Lys Asp Tyr Tyr Ala Ile Arg Ala Glu Asp Gly Lys Phe
                            260                 265                 270

Tyr Asp Arg Asn Gly Thr Gly Leu Ala Lys Gly Phe Leu Arg Phe Pro
                            275                 280                 285

Thr Ala Lys Gln Phe Arg Ile Ser Ser Asn Phe Asn Pro Arg Arg Thr
                            290                 295                 300

Asn Pro Val Thr Gly Arg Val Ala Pro His Arg Gly Val Asp Phe Ala
        305                 310                 315                 320

Met Pro Gln Gly Thr Pro Val Leu Ser Val Gly Asp Gly Glu Val Val
                            325                 330                 335

Val Ala Lys Arg Ser Gly Ala Ala Gly Tyr Tyr Val Ala Ile Arg His
                            340                 345                 350

Gly Arg Ser Tyr Thr Thr Arg Tyr Met His Leu Arg Lys Ile Leu Val
                            355                 360                 365

Lys Pro Gly Gln Lys Val Lys Arg Gly Asp Arg Ile Ala Leu Ser Gly
                            370                 375                 380

Asn Thr Gly Arg Ser Thr Gly Pro His Leu His Tyr Glu Val Trp Ile
        385                 390                 395                 400

Asn Gln Gln Ala Val Asn Pro Leu Thr Ala Lys Leu Pro Arg Thr Glu
                            405                 410                 415

Gly Leu Thr Gly Ser Asp Arg Arg Glu Phe Leu Ala Gln Ala Lys Glu
                            420                 425                 430

Ile Val Pro Gln Leu Arg Phe Asp
                            435                 440

<210> SEQ ID NO 8
<211> LENGTH: 95
<212> TYPE: PRT
<213> ORGANISM: Escherichia coli

<400> SEQUENCE: 8

Pro His Arg Gly Val Asp Phe Ala Met Pro Gln Gly Thr Pro Val Leu
1               5                   10                  15

Ser Val Gly Asp Gly Glu Val Val Ala Lys Arg Ser Gly Ala Ala
                20                  25                  30

Gly Tyr Tyr Val Ala Ile Arg His Gly Arg Ser Tyr Thr Thr Arg Tyr
                35                  40                  45

Met His Leu Arg Lys Ile Leu Val Lys Pro Gly Gln Lys Val Lys Arg
                50                  55                  60

Gly Asp Arg Ile Ala Leu Ser Gly Asn Thr Gly Arg Ser Thr Gly Pro
65                  70                  75                  80
```

His Leu His Tyr Glu Val Trp Ile Asn Gln Gln Ala Val Asn Pro
            85                  90                  95

<210> SEQ ID NO 9
<211> LENGTH: 419
<212> TYPE: PRT
<213> ORGANISM: Escherichia coli

<400> SEQUENCE: 9

Met Thr Arg Ala Val Lys Pro Arg Arg Phe Ala Ile Arg Pro Ile Ile
1               5                   10                  15

Tyr Ala Ser Val Leu Ser Ala Gly Val Leu Leu Cys Ala Phe Ser Ala
            20                  25                  30

His Ala Asp Glu Arg Asp Gln Leu Lys Ser Ile Gln Ala Asp Ile Ala
        35                  40                  45

Ala Lys Glu Arg Ala Val Arg Gln Lys Gln Gln Arg Ala Ser Leu
    50                  55                  60

Leu Ala Gln Leu Lys Lys Gln Glu Ala Ile Ser Glu Ala Thr Arg
65                  70                  75                  80

Lys Leu Arg Glu Thr Gln Asn Thr Leu Asn Gln Leu Asn Lys Gln Ile
                85                  90                  95

Asp Glu Met Asn Ala Ser Ile Ala Lys Leu Glu Gln Gln Lys Ala Ala
            100                 105                 110

Gln Glu Arg Ser Leu Ala Ala Gln Leu Asp Ala Ala Phe Arg Gln Gly
        115                 120                 125

Glu His Thr Gly Ile Gln Leu Ile Leu Ser Gly Glu Glu Ser Gln Arg
    130                 135                 140

Gly Gln Arg Leu Gln Ala Tyr Phe Gly Tyr Leu Asn Gln Ala Arg Gln
145                 150                 155                 160

Glu Thr Ile Ala Gln Leu Lys Gln Thr Arg Glu Glu Val Ala Met Gln
                165                 170                 175

Arg Ala Glu Leu Glu Glu Lys Gln Ser Glu Gln Gln Thr Leu Leu Tyr
            180                 185                 190

Glu Gln Arg Ala Gln Gln Ala Lys Leu Thr Gln Ala Leu Asn Glu Arg
        195                 200                 205

Lys Lys Thr Leu Ala Gly Leu Glu Ser Ser Ile Gln Gln Gly Gln Gln
    210                 215                 220

Gln Leu Ser Glu Leu Arg Ala Asn Glu Ser Arg Leu Arg Asn Ser Ile
225                 230                 235                 240

Ala Arg Ala Glu Ala Ala Lys Ala Arg Ala Glu Arg Glu Ala Arg
                245                 250                 255

Glu Ala Gln Ala Val Arg Asp Arg Gln Lys Glu Ala Thr Arg Lys Gly
            260                 265                 270

Thr Thr Tyr Lys Pro Thr Glu Ser Glu Lys Ser Leu Met Ser Arg Thr
        275                 280                 285

Gly Gly Leu Gly Ala Pro Arg Gly Gln Ala Phe Trp Pro Val Arg Gly
    290                 295                 300

Pro Thr Leu His Arg Tyr Gly Glu Gln Leu Gln Gly Glu Leu Arg Trp
305                 310                 315                 320

Lys Gly Met Val Ile Gly Ala Ser Glu Gly Thr Glu Val Lys Ala Ile
                325                 330                 335

Ala Asp Gly Arg Val Ile Leu Ala Asp Trp Leu Gln Gly Tyr Gly Leu
            340                 345                 350

Val Val Val Val Glu His Gly Lys Gly Asp Met Ser Leu Tyr Gly Tyr
        355                 360                 365

```
Asn Gln Ser Ala Leu Val Ser Val Gly Ser Gln Val Arg Ala Gly Gln
        370                 375                 380

Pro Ile Ala Leu Val Gly Ser Ser Gly Gly Gln Gly Arg Pro Ser Leu
385                 390                 395                 400

Tyr Phe Glu Ile Arg Arg Gln Gly Gln Ala Val Asn Pro Gln Pro Trp
                405                 410                 415

Leu Gly Arg

<210> SEQ ID NO 10
<211> LENGTH: 96
<212> TYPE: PRT
<213> ORGANISM: Escherichia coli

<400> SEQUENCE: 10

Leu Arg Trp Lys Gly Met Val Ile Gly Ala Ser Glu Gly Thr Glu Val
1               5                   10                  15

Lys Ala Ile Ala Asp Gly Arg Val Ile Leu Ala Asp Trp Leu Gln Gly
                20                  25                  30

Tyr Gly Leu Val Val Val Val Glu His Gly Lys Gly Asp Met Ser Leu
            35                  40                  45

Tyr Gly Tyr Asn Gln Ser Ala Leu Val Ser Val Gly Ser Gln Val Arg
50                  55                  60

Ala Gly Gln Pro Ile Ala Leu Val Gly Ser Ser Gly Gly Gln Gly Arg
65                  70                  75                  80

Pro Ser Leu Tyr Phe Glu Ile Arg Arg Gln Gly Gln Ala Val Asn Pro
                85                  90                  95

<210> SEQ ID NO 11
<211> LENGTH: 379
<212> TYPE: PRT
<213> ORGANISM: Escherichia coli

<400> SEQUENCE: 11

Met Ser Ala Gly Ser Pro Lys Phe Thr Val Arg Arg Ile Ala Ala Leu
1               5                   10                  15

Ser Leu Val Ser Leu Trp Leu Ala Gly Cys Ser Asp Thr Ser Asn Pro
                20                  25                  30

Pro Ala Pro Val Ser Ser Val Asn Gly Asn Ala Pro Ala Asn Thr Asn
            35                  40                  45

Ser Gly Met Leu Ile Thr Pro Pro Lys Met Gly Thr Thr Ser Thr
50                  55                  60

Ala Gln Gln Pro Gln Ile Gln Pro Val Gln Gln Pro Gln Ile Gln Ala
65                  70                  75                  80

Thr Gln Gln Pro Gln Ile Gln Pro Val Gln Pro Val Ala Gln Gln Pro
                85                  90                  95

Val Gln Met Glu Asn Gly Arg Ile Val Tyr Asn Arg Gln Tyr Gly Asn
            100                 105                 110

Ile Pro Lys Gly Ser Tyr Ser Gly Ser Thr Tyr Thr Val Lys Lys Gly
        115                 120                 125

Asp Thr Leu Phe Tyr Ile Ala Trp Ile Thr Gly Asn Asp Phe Arg Asp
    130                 135                 140

Leu Ala Gln Arg Asn Asn Ile Gln Ala Pro Tyr Ala Leu Asn Val Gly
145                 150                 155                 160

Gln Thr Leu Gln Val Gly Asn Ala Ser Gly Thr Pro Ile Thr Gly Gly
                165                 170                 175
```

Asn Ala Ile Thr Gln Ala Asp Ala Glu Gln Gly Val Val Ile Lys
            180                 185                 190

Pro Ala Gln Asn Ser Thr Val Ala Val Ala Ser Gln Pro Thr Ile Thr
        195                 200                 205

Tyr Ser Glu Ser Ser Gly Glu Gln Ser Ala Asn Lys Met Leu Pro Asn
    210                 215                 220

Asn Lys Pro Thr Ala Thr Thr Val Thr Ala Pro Val Thr Val Pro Thr
225                 230                 235                 240

Ala Ser Thr Thr Glu Pro Thr Val Ser Ser Thr Ser Thr Ser Thr Pro
                245                 250                 255

Ile Ser Thr Trp Arg Trp Pro Thr Glu Gly Lys Val Ile Glu Thr Phe
        260                 265                 270

Gly Ala Ser Glu Gly Gly Asn Lys Gly Ile Asp Ile Ala Gly Ser Lys
    275                 280                 285

Gly Gln Ala Ile Ile Ala Thr Ala Asp Gly Arg Val Val Tyr Ala Gly
290                 295                 300

Asn Ala Leu Arg Gly Tyr Gly Asn Leu Ile Ile Ile Lys His Asn Asp
305                 310                 315                 320

Asp Tyr Leu Ser Ala Tyr Ala His Asn Asp Thr Met Leu Val Arg Glu
                325                 330                 335

Gln Gln Glu Val Lys Ala Gly Gln Lys Ile Ala Thr Met Gly Ser Thr
            340                 345                 350

Gly Thr Ser Ser Thr Arg Leu His Phe Glu Ile Arg Tyr Lys Gly Lys
        355                 360                 365

Ser Val Asn Pro Leu Arg Tyr Leu Pro Gln Arg
    370                 375

<210> SEQ ID NO 12
<211> LENGTH: 96
<212> TYPE: PRT
<213> ORGANISM: Escherichia coli

<400> SEQUENCE: 12

Gly Gly Asn Lys Gly Ile Asp Ile Ala Gly Ser Lys Gly Gln Ala Ile
1               5                   10                  15

Ile Ala Thr Ala Asp Gly Arg Val Val Tyr Ala Gly Asn Ala Leu Arg
            20                  25                  30

Gly Tyr Gly Asn Leu Ile Ile Ile Lys His Asn Asp Asp Tyr Leu Ser
        35                  40                  45

Ala Tyr Ala His Asn Asp Thr Met Leu Val Arg Glu Gln Gln Glu Val
    50                  55                  60

Lys Ala Gly Gln Lys Ile Ala Thr Met Gly Ser Thr Gly Thr Ser Ser
65                  70                  75                  80

Thr Arg Leu His Phe Glu Ile Arg Tyr Lys Gly Lys Ser Val Asn Pro
                85                  90                  95

<210> SEQ ID NO 13
<211> LENGTH: 5
<212> TYPE: PRT
<213> ORGANISM: Artificial Sequence
<220> FEATURE:
<223> OTHER INFORMATION: LytM domain
<220> FEATURE:
<221> NAME/KEY: misc_feature
<222> LOCATION: 2, 3, 4
<223> OTHER INFORMATION: 'Xaa' is any amino acid

<400> SEQUENCE: 13

```
His Xaa Xaa Xaa Asp
1               5

<210> SEQ ID NO 14
<211> LENGTH: 5
<212> TYPE: PRT
<213> ORGANISM: Artificial Sequence
<220> FEATURE:
<223> OTHER INFORMATION: LytM domain

<400> SEQUENCE: 14

His Lys Gly Val Asp
1               5

<210> SEQ ID NO 15
<211> LENGTH: 5
<212> TYPE: PRT
<213> ORGANISM: Artificial Sequence
<220> FEATURE:
<223> OTHER INFORMATION: LytM domain

<400> SEQUENCE: 15

His Arg Gly Val Asp
1               5

<210> SEQ ID NO 16
<211> LENGTH: 5
<212> TYPE: PRT
<213> ORGANISM: Artificial Sequence
<220> FEATURE:
<223> OTHER INFORMATION: LytM domain

<400> SEQUENCE: 16

His Thr Gly Ile Asp
1               5

<210> SEQ ID NO 17
<211> LENGTH: 5
<212> TYPE: PRT
<213> ORGANISM: Artificial Sequence
<220> FEATURE:
<223> OTHER INFORMATION: LytM motif

<400> SEQUENCE: 17

Asn Lys Gly Val Asp
1               5

<210> SEQ ID NO 18
<211> LENGTH: 5
<212> TYPE: PRT
<213> ORGANISM: Artificial Sequence
<220> FEATURE:
<223> OTHER INFORMATION: LytM motif

<400> SEQUENCE: 18

Thr Lys Gly Ile Asp
1               5

<210> SEQ ID NO 19
<211> LENGTH: 5
<212> TYPE: PRT
<213> ORGANISM: Artificial Sequence
<220> FEATURE:
<223> OTHER INFORMATION: LytM motif

<400> SEQUENCE: 19

Asn Lys Gly Ile Asp
```

```
<210> SEQ ID NO 20
<211> LENGTH: 5
<212> TYPE: PRT
<213> ORGANISM: Artificial Sequence
<220> FEATURE:
<223> OTHER INFORMATION: LytM motif

<400> SEQUENCE: 20

Trp Lys Gly Val Phe
1               5

<210> SEQ ID NO 21
<211> LENGTH: 5
<212> TYPE: PRT
<213> ORGANISM: Artificial Sequence
<220> FEATURE:
<223> OTHER INFORMATION: LytM motif

<400> SEQUENCE: 21

Trp Arg Gly Leu Val
1               5

<210> SEQ ID NO 22
<211> LENGTH: 5
<212> TYPE: PRT
<213> ORGANISM: Artificial Sequence
<220> FEATURE:
<223> OTHER INFORMATION: LytM motif

<400> SEQUENCE: 22

Trp Lys Gly Met Val
1               5

<210> SEQ ID NO 23
<211> LENGTH: 26
<212> TYPE: DNA
<213> ORGANISM: Artificial Sequence
<220> FEATURE:
<223> OTHER INFORMATION: immunostimulatory oligodeoxynucleotide
<220> FEATURE:
<221> NAME/KEY: modified_base
<222> LOCATION: 1, 3, 5, 7, 9, 11, 13, 15, 17, 19, 21, 23, 25
<223> OTHER INFORMATION: 'n' is 'i' (Inosine)

<400> SEQUENCE: 23
ncncncncnc ncncncncnc ncncnc                                   26

<210> SEQ ID NO 24
<211> LENGTH: 11
<212> TYPE: PRT
<213> ORGANISM: Artificial Sequence
<220> FEATURE:
<223> OTHER INFORMATION: antimicrobial peptide

<400> SEQUENCE: 24

Lys Leu Lys Leu Leu Leu Leu Leu Lys Leu Lys
1               5                   10

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
```
ttgcacgcgc caataatacc                                          20

<210> SEQ ID NO 26
<211> LENGTH: 29
<212> TYPE: DNA
<213> ORGANISM: Artificial Sequence
<220> FEATURE:
<223> OTHER INFORMATION: Primer

<400> SEQUENCE: 26
tgcatgcatt tacgtgttgc actggcatc                                29

<210> SEQ ID NO 27
<211> LENGTH: 29
<212> TYPE: DNA
<213> ORGANISM: Artificial Sequence
<220> FEATURE:
<223> OTHER INFORMATION: Primer

<400> SEQUENCE: 27
tgcatgcatt gttcgtgttc gtgaagcag                                29

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
aacgcgattg cgtaatgcag                                          20

<210> SEQ ID NO 29
<211> LENGTH: 21
<212> TYPE: DNA
<213> ORGANISM: Artificial Sequence
<220> FEATURE:
<223> OTHER INFORMATION: Primer

<400> SEQUENCE: 29
tgctggtgca atttgatctt c                                        21

<210> SEQ ID NO 30
<211> LENGTH: 30
<212> TYPE: DNA
<213> ORGANISM: Artificial Sequence
<220> FEATURE:
<223> OTHER INFORMATION: Primer

<400> SEQUENCE: 30
tgcatgcatt gattaacgcc aaaacgcaac                               30

<210> SEQ ID NO 31
<211> LENGTH: 29
<212> TYPE: DNA
<213> ORGANISM: Artificial Sequence
<220> FEATURE:
<223> OTHER INFORMATION: Primer

<400> SEQUENCE: 31
tgcatgcata ttagccgtaa aggaacgcc                                29

<210> SEQ ID NO 32
<211> LENGTH: 20
<212> TYPE: DNA

```
<213> ORGANISM: Artificial Sequence
<220> FEATURE:
<223> OTHER INFORMATION: Primer

<400> SEQUENCE: 32
tggcgatcta atgaacgcac                                              20

<210> SEQ ID NO 33
<211> LENGTH: 21
<212> TYPE: DNA
<213> ORGANISM: Artificial Sequence
<220> FEATURE:
<223> OTHER INFORMATION: Primer

<400> SEQUENCE: 33
aaacattgtg caacaatggg g                                            21

<210> SEQ ID NO 34
<211> LENGTH: 30
<212> TYPE: DNA
<213> ORGANISM: Artificial Sequence
<220> FEATURE:
<223> OTHER INFORMATION: Primer

<400> SEQUENCE: 34
tgcatgcata caagactcaa agggagtaag                                   30

<210> SEQ ID NO 35
<211> LENGTH: 29
<212> TYPE: DNA
<213> ORGANISM: Artificial Sequence
<220> FEATURE:
<223> OTHER INFORMATION: Primer

<400> SEQUENCE: 35
tgcatgcatg gatccagtac gttacctac                                    29

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
gtttctttgt ccgcaggttc                                              20

<210> SEQ ID NO 37
<211> LENGTH: 1248
<212> TYPE: DNA
<213> ORGANISM: Neisseria meningitidis

<400> SEQUENCE: 37
atgttgaaac aaacgacact tttggcagct tgtaccgccg ttgccgctct gttgggcggt      60
tgcgccaccc aacagcctgc tcctgtcatt gcaggcaatt caggtatgca ggacgcgccg     120
tcttcggcag tttacaacaa cccctatgga gcaacgccgt acagcccggc tcctgccggc     180
gatgcgcctt atgtgccgcc ggtgcaaagc gcgccggttt atacgcctcc tgcttatgtt     240
ccgccgtctg cacctgccgt tcgggtaca tacgttcctt cttacgcacc cgtcgacatc     300
aacgcggcga cgcatactat tgtgcgcggg gacacggtgt acaacatttc caaacgctac     360
catatctctc aagacgattt ccgtgcgtgg aacggcatga ccgacaatac gttgagcatc     420
ggtcagattg ttaaagtcaa accggcagga tatgccgcac cgaaagccgc agccgtaaaa     480
```

```
agcaggcccg ccgtaccggc tgccgcgcaa ccgcccgtac agtccgcacc cgtcgacatt    540
aacgcggcga cgcatactat tgtgcgcggc gacacggtgt acaacatttc caaacgctac    600
catatctctc aagacgattt ccgtgcgtgg aacggcatga ccgacaatat gttgagcatc    660
ggtcagattg ttaaagtcaa accggcagga tatgccgcac cgaaaaccgc agccgtagaa    720
agcaggcccg ccgtaccggc tgccgtgcaa acccctgtga aacccgccgc gcaaccgcct    780
gtgcagtccg cgccgcaacc tgccgcgccc gctgcggaaa ataaagcggt tcccgcgccc    840
gccccgcaat ctcctgccgc ttcgccttcc ggcacgcgtt cggtcggcgg cattgtttgg    900
cagcgtccga cgcaaggtaa agtggttgcc gatttcggcg caacaacaa gggtgtcgat    960 attgccggta atgcgggaca gcccgttttg gcggcggctg acggcaaagt ggtttatgcc    1020
ggttcaggtt tgagggggata cggaaacttg gtcatcatcc agcataattc ttctttcctg    1080
accgcatacg ggcacaacca aaaattgctg gtcggcgagg ggcagcaggt caaacgcggt    1140
cagcaggttg ctttgatggg caataccgat gcttccagaa cgcagcttca tttcgaggtg    1200
cgtcaaaacg gcaaaccggt taacccgaac agctatatcg cgttctga                1248
```

<210> SEQ ID NO 38
<211> LENGTH: 1293
<212> TYPE: DNA
<213> ORGANISM: Neisseria meningitidis

<400> SEQUENCE: 38

```
atggctgtct tcccactttc ggcaaaacat cggaaatacg cgctgcgtgc gcttgccgtt     60
tcgattattt tggtgtcggc ggcatacatt gcttcgacag agaggacgga gcgcgtcaga    120
ccgcagcgcg tggaacaaaa tctgccgccg ctgtcttggg gcggcagcgg cgttcagacg    180
gcatattggg tgcaggaggc ggtgcagccg ggcgactcgc tggcggacgt gctggcgcgt    240
tcgggtatgg cgcgggacga gattgcccga atcacggaaa aatatggcgg cgaagccgat    300
ttgcggcatt tgcgtgccga ccagtcggtt catgttttgg tcggcggcga cggcggcgcg    360
cgcgaagtgc agttttttac cgacgaagac ggcgagcgca atctggtcgc tttggaaaag    420
aaaggcggca tatggcggcg gtcggcttct gaggcggata tgaaggtttt gccgacgctg    480
cgttcggtcg tggtcaaaac gtcggcgcgc ggttcgctgg cgcgggcgga agtgcccgtc    540
gaaatccgcg aatccttaag cgggattttc gccggccgct tcagccttga cggtttgaag    600
gaaggcgatg ccgtgcgcct gatgtacgac agcctgtatt ccacgggca gcaggtggcg    660 gcgggcgata ttttggcggc tgaagtcgtt aagggcggca caaggcatca ggcgttctat    720
taccgttcgg acaaggaagg cggaggggc ggcaattatt atgatgaaga cggcaaggtg    780
ttgcaggaaa aaggcggctt caacatcgag ccgctggtct atacgcgcat tcttcgccg    840 ttcggctacc gtatgcaccc catcctgcac acatggcggc tgcacacggg catcgattat    900
gccgcaccgc agggaacgcc ggtcaggcct tccgccgacg gcgtgattac ctttaaaggc    960
cggaagggcg gatacggcaa cgcggtgatg atacgccacg ccaacggtgt ggaaacgctg    1020
tacgcgcact tgagcgcgtt ttcgcaggcg gaaggcaatg tgcgcggcgg cgaggtcatc    1080
ggttttgtcg gttcgaccgg gcgttcgacc gggccgcacc tgcattacga ggcgcgcatc    1140
aacgggcagc ccgtcaatcc tgtttcggtc gcattgccga caccggaatt gacgcaggcg    1200 gacaaggcg cgtttgccgc gcagaaacag aaggcggacg cgctgcttgc gcgcttgcgc    1260
ggcataccgg ttaccgtgtc gcaatcggat tga                                1293
```

<210> SEQ ID NO 39
<211> LENGTH: 1791
<212> TYPE: DNA
<213> ORGANISM: Neisseria meningitidis

<400> SEQUENCE: 39

```
atgcgctaca aaccccttct gcttgccctg atgctcgttt tttccacgcc cgccgttgcc      60
gcccacgacg cggcacacaa ccgttccgcc gaagtgaaaa acagacgaa gaacaaaaaa      120
gaacagcccg aagcggcgga aggcaaaaaa gaaaaaggca aaatggcgc agtgaaagat      180
aaaaaaacag gcggcaaaga ggcggcaaaa gagggcaaag agtccaaaaa aaccgccaaa      240
aaccgcaaag aagcagagaa ggaggcgaca tccaggcagt ctgcgcgcaa aggacgcgaa      300
ggggataaga aatcgaaggc ggaacacaaa aaggcacatg gcaagcccgt gtccggatcc      360
aaagaaaaaa acgcaaaaac acagcctgaa aacaaacaag gcaaaaaaga ggcaaaagga      420
cagggcaatc cgcgcaaggg cggcaaggcg gaaaagaca ctgtttctgc aaataaaaaa       480
gtccgttccg acaagaacgg caaagcagtg aaacaggaca aaaatacag ggaagagaaa      540
aatgccaaaa ccgattccga cgaattgaaa gccgccgttg ccgctgccac caatgatgtc      600
gaaaacaaaa aagcccgct caaacaaagc gaaggaatgc tgcttcatgt cagcaattcc      660
ctcaaacagc ttcaggaaga gcgtatccgc caagagcgta tccgtcaggc gcgcggcaac      720
cttgcttccg tcaaccgcaa acagcgcgag gcttgggaca agttccaaaa actcaatacc      780
gagctgaacc gtttgaaaac ggaagtcgcc gctacgaaag cgcagatttc ccgtttcgta      840
tcggggaact ataaaaacag ccagccgaat gcggttgccc tgttcctgaa aaacgccgaa      900
ccgggtcaga aaaccgcttt ttgcgttat acgcgttatg taaacgcctc caatcgggaa      960
gttgtcaagg atttggaaaa acagcagaag gctttggcgg tacaagagca gaaaatcaac     1020
aatgagcttg cccgttttgaa gaaaattcag gcaaacgtgc aatctctgct gaaaaaacag     1080
ggtgtaaccg atgcggcgga acagacggaa agccgcagac agaatgccaa aatcgccaaa     1140
gatgcccgaa aactgctgga acagaaaggg aacgagcagc agctgaacaa gctcttgagc     1200
aatttggaga gaaaaaggc cgaacaccgc attcaggatg cggaagcaaa aagaaaattg     1260
gctgaagcca gactggcggc agccgaaaaa gccagaaaag aagcggcgca gcagaaggct     1320
gaagcacgac gtgcggaaat gtccaacctg accgccgaag acaggaacat ccaagcgcct     1380
tcggttatgg gtatcggcag tgccgacggt ttcagccgca tgcaaggacg tttgaaaaaa     1440
ccggttgacg gtgtgccgac cggactttc gggcagaacc ggagcggcgg cgatatttgg     1500
aaaggcgtgt ctattccac tgcaccggca acggttgaaa gcattgcgcc gggaacggta     1560
agctatgcgg acgagttgga cggctacggc aaagtggtcg tggtcgatca cggcgagaac     1620
tacatcagca tctatgccgg tttgagcgaa atttccgtcg gcaagggtta tatggtcgcg     1680
gcaggaagca aaatcggctc gagcgggtcg ctgccggacg gggaagaggg gctttacctg     1740
caaatacgtt atcaaggtca ggtattgaac ccttcgagct ggatacgttg a             1791
```

<210> SEQ ID NO 40
<211> LENGTH: 415
<212> TYPE: PRT
<213> ORGANISM: Neisseria meningitidis

<400> SEQUENCE: 40

```
Met Leu Lys Gln Thr Thr Leu Leu Ala Ala Cys Thr Ala Val Ala Ala
1               5                   10                  15
```

-continued

Leu Leu Gly Gly Cys Ala Thr Gln Gln Pro Ala Pro Val Ile Ala Gly
            20                  25                  30

Asn Ser Gly Met Gln Asp Ala Pro Ser Ser Ala Val Tyr Asn Asn Pro
        35                  40                  45

Tyr Gly Ala Thr Pro Tyr Ser Pro Ala Pro Ala Gly Asp Ala Pro Tyr
    50                  55                  60

Val Pro Pro Val Gln Ser Ala Pro Val Tyr Thr Pro Pro Ala Tyr Val
65                  70                  75                  80

Pro Pro Ser Ala Pro Ala Val Ser Gly Thr Tyr Val Pro Ser Tyr Ala
                85                  90                  95

Pro Val Asp Ile Asn Ala Ala Thr His Thr Ile Val Arg Gly Asp Thr
            100                 105                 110

Val Tyr Asn Ile Ser Lys Arg Tyr His Ile Ser Gln Asp Asp Phe Arg
        115                 120                 125

Ala Trp Asn Gly Met Thr Asp Asn Thr Leu Ser Ile Gly Gln Ile Val
    130                 135                 140

Lys Val Lys Pro Ala Gly Tyr Ala Ala Pro Lys Ala Ala Ala Val Lys
145                 150                 155                 160

Ser Arg Pro Ala Val Pro Ala Ala Gln Pro Pro Val Gln Ser Ala
                165                 170                 175

Pro Val Asp Ile Asn Ala Ala Thr His Thr Ile Val Arg Gly Asp Thr
            180                 185                 190

Val Tyr Asn Ile Ser Lys Arg Tyr His Ile Ser Gln Asp Asp Phe Arg
        195                 200                 205

Ala Trp Asn Gly Met Thr Asp Asn Met Leu Ser Ile Gly Gln Ile Val
    210                 215                 220

Lys Val Lys Pro Ala Gly Tyr Ala Ala Pro Lys Thr Ala Ala Val Glu
225                 230                 235                 240

Ser Arg Pro Ala Val Pro Ala Ala Val Gln Thr Pro Val Lys Pro Ala
                245                 250                 255

Ala Gln Pro Pro Val Gln Ser Ala Pro Gln Pro Ala Ala Pro Ala Ala
            260                 265                 270

Glu Asn Lys Ala Val Pro Ala Pro Ala Pro Gln Ser Pro Ala Ala Ser
        275                 280                 285

Pro Ser Gly Thr Arg Ser Val Gly Gly Ile Val Trp Gln Arg Pro Thr
    290                 295                 300

Gln Gly Lys Val Val Ala Asp Phe Gly Gly Asn Lys Gly Val Asp
305                 310                 315                 320

Ile Ala Gly Asn Ala Gly Gln Pro Val Leu Ala Ala Asp Gly Lys
                325                 330                 335

Val Val Tyr Ala Gly Ser Gly Leu Arg Gly Tyr Gly Asn Leu Val Ile
            340                 345                 350

Ile Gln His Asn Ser Ser Phe Leu Thr Ala Tyr Gly His Asn Gln Lys
        355                 360                 365

Leu Leu Val Gly Glu Gly Gln Gln Val Lys Arg Gly Gln Gln Val Ala
    370                 375                 380

Leu Met Gly Asn Thr Asp Ala Ser Arg Thr Gln Leu His Phe Glu Val
385                 390                 395                 400

Arg Gln Asn Gly Lys Pro Val Asn Pro Asn Ser Tyr Ile Ala Phe
                405                 410                 415

<210> SEQ ID NO 41
<211> LENGTH: 430
<212> TYPE: PRT

<213> ORGANISM: Neisseria meningitidis

<400> SEQUENCE: 41

```
Met Ala Val Phe Pro Leu Ser Ala Lys His Arg Lys Tyr Ala Leu Arg
1               5                   10                  15

Ala Leu Ala Val Ser Ile Ile Leu Val Ser Ala Ala Tyr Ile Ala Ser
            20                  25                  30

Thr Glu Arg Thr Glu Arg Val Arg Pro Gln Arg Val Glu Gln Asn Leu
        35                  40                  45

Pro Pro Leu Ser Trp Gly Gly Ser Gly Val Gln Thr Ala Tyr Trp Val
    50                  55                  60

Gln Glu Ala Val Gln Pro Gly Asp Ser Leu Ala Asp Val Leu Ala Arg
65                  70                  75                  80

Ser Gly Met Ala Arg Asp Glu Ile Ala Arg Ile Thr Glu Lys Tyr Gly
                85                  90                  95

Gly Glu Ala Asp Leu Arg His Leu Arg Ala Asp Gln Ser Val His Val
            100                 105                 110

Leu Val Gly Gly Asp Gly Gly Ala Arg Glu Val Gln Phe Phe Thr Asp
        115                 120                 125

Glu Asp Gly Glu Arg Asn Leu Val Ala Leu Glu Lys Lys Gly Gly Ile
130                 135                 140

Trp Arg Arg Ser Ala Ser Glu Ala Asp Met Lys Val Leu Pro Thr Leu
145                 150                 155                 160

Arg Ser Val Val Lys Thr Ser Ala Arg Gly Ser Leu Ala Arg Ala
                165                 170                 175

Glu Val Pro Val Glu Ile Arg Glu Ser Leu Ser Gly Ile Phe Ala Gly
            180                 185                 190

Arg Phe Ser Leu Asp Gly Leu Lys Glu Gly Asp Ala Val Arg Leu Met
        195                 200                 205

Tyr Asp Ser Leu Tyr Phe His Gly Gln Gln Val Ala Ala Gly Asp Ile
210                 215                 220

Leu Ala Ala Glu Val Val Lys Gly Gly Thr Arg His Gln Ala Phe Tyr
225                 230                 235                 240

Tyr Arg Ser Asp Lys Glu Gly Gly Gly Gly Asn Tyr Tyr Asp Glu
                245                 250                 255

Asp Gly Lys Val Leu Gln Glu Lys Gly Gly Phe Asn Ile Glu Pro Leu
            260                 265                 270

Val Tyr Thr Arg Ile Ser Ser Pro Phe Gly Tyr Arg Met His Pro Ile
        275                 280                 285

Leu His Thr Trp Arg Leu His Thr Gly Ile Asp Tyr Ala Ala Pro Gln
290                 295                 300

Gly Thr Pro Val Arg Ala Ser Ala Asp Gly Val Ile Thr Phe Lys Gly
305                 310                 315                 320

Arg Lys Gly Gly Tyr Gly Asn Ala Val Met Ile Arg His Ala Asn Gly
                325                 330                 335

Val Glu Thr Leu Tyr Ala His Leu Ser Ala Phe Ser Gln Ala Glu Gly
            340                 345                 350

Asn Val Arg Gly Gly Glu Val Ile Gly Phe Val Gly Ser Thr Gly Arg
        355                 360                 365

Ser Thr Gly Pro His Leu His Tyr Glu Ala Arg Ile Asn Gly Gln Pro
370                 375                 380

Val Asn Pro Val Ser Val Ala Leu Pro Thr Pro Glu Leu Thr Gln Ala
385                 390                 395                 400
```

```
                Asp Lys Ala Ala Phe Ala Ala Gln Lys Gln Lys Ala Asp Ala Leu Leu
                                405                 410                 415

Ala Arg Leu Arg Gly Ile Pro Val Thr Val Ser Gln Ser Asp
                        420                 425                 430

<210> SEQ ID NO 42
<211> LENGTH: 297
<212> TYPE: PRT
<213> ORGANISM: Neisseria meningitidis

<400> SEQUENCE: 42

Glu Pro Gly Gln Lys Asn Arg Phe Leu Arg Tyr Thr Arg Tyr Val Asn
1               5                   10                  15

Ala Ser Asn Arg Glu Val Val Lys Asp Leu Glu Lys Gln Gln Lys Ala
            20                  25                  30

Leu Ala Val Gln Glu Gln Lys Ile Asn Asn Glu Leu Ala Arg Leu Lys
        35                  40                  45

Lys Ile Gln Ala Asn Val Gln Ser Leu Leu Lys Gln Gly Val Thr
    50                  55                  60

Asp Ala Ala Glu Gln Thr Glu Ser Arg Arg Gln Asn Ala Lys Ile Ala
65                  70                  75                  80

Lys Asp Ala Arg Lys Leu Leu Glu Gln Lys Gly Asn Glu Gln Gln Leu
                85                  90                  95

Asn Lys Leu Leu Ser Asn Leu Glu Lys Lys Ala Glu His Arg Ile
            100                 105                 110

Gln Asp Ala Glu Ala Lys Arg Lys Leu Ala Glu Ala Arg Leu Ala Ala
        115                 120                 125

Ala Glu Lys Ala Arg Lys Glu Ala Gln Gln Lys Ala Glu Ala Arg
    130                 135                 140

Arg Ala Glu Met Ser Asn Leu Thr Ala Glu Asp Arg Asn Ile Gln Ala
145                 150                 155                 160

Pro Ser Val Met Gly Ile Gly Ser Ala Asp Gly Phe Ser Arg Met Gln
                165                 170                 175

Gly Arg Leu Lys Lys Pro Val Asp Gly Val Pro Thr Gly Leu Phe Gly
            180                 185                 190

Gln Asn Arg Ser Gly Gly Asp Ile Trp Lys Gly Val Phe Tyr Ser Thr
        195                 200                 205

Ala Pro Ala Thr Val Glu Ser Ile Ala Pro Gly Thr Val Ser Tyr Ala
    210                 215                 220

Asp Glu Leu Asp Gly Tyr Gly Lys Val Val Val Asp His Gly Glu
225                 230                 235                 240

Asn Tyr Ile Ser Ile Tyr Ala Gly Leu Ser Glu Ile Ser Val Gly Lys
                245                 250                 255

Gly Tyr Met Val Ala Ala Gly Ser Lys Ile Gly Ser Ser Gly Ser Leu
            260                 265                 270

Pro Asp Gly Glu Glu Gly Leu Tyr Leu Gln Ile Arg Tyr Gln Gly Gln
        275                 280                 285

Val Leu Asn Pro Ser Ser Trp Ile Arg
    290                 295

<210> SEQ ID NO 43
<211> LENGTH: 29
<212> TYPE: DNA
<213> ORGANISM: Artificial Sequence
<220> FEATURE:
<223> OTHER INFORMATION: Primer
```

<400> SEQUENCE: 43
gctctagacg ttacagcggc aattattgc                                            29

<210> SEQ ID NO 44
<211> LENGTH: 30
<212> TYPE: DNA
<213> ORGANISM: Artificial Sequence
<220> FEATURE:
<223> OTHER INFORMATION: Primer

<400> SEQUENCE: 44
tcccccgggc gcagacagta cagatagtac                                           30

<210> SEQ ID NO 45
<211> LENGTH: 29
<212> TYPE: DNA
<213> ORGANISM: Artificial Sequence
<220> FEATURE:
<223> OTHER INFORMATION: Primer

<400> SEQUENCE: 45
tcccccggga tgttccgata tatagcctg                                            29

<210> SEQ ID NO 46
<211> LENGTH: 28
<212> TYPE: DNA
<213> ORGANISM: Artificial Sequence
<220> FEATURE:
<223> OTHER INFORMATION: Primer

<400> SEQUENCE: 46
ccgctcgacc cctattttgt ggaacatc                                             28

<210> SEQ ID NO 47
<211> LENGTH: 885
<212> TYPE: DNA
<213> ORGANISM: Bordetella pertussis

<400> SEQUENCE: 47
atgctcaacg ggcagttgca actgaccgaa tcccaatccg tggctggcgc atccgccgcc 60
gccgcttccc gccccgttct ctgggcgggc gtgctggcca tcgccttgct ggccggctgc 120
gcctcgaagg gcccgcgcgc gcctgtggtc gacctcaccg gacagcccgg cgcctccggc 180
ccgaccgacg gcagctatgt cgtcaagcct ggcgatacgc tctacaagat cgcgcgcgcc 240
aacaatgtcg atatcgaaaa cctcaagcgc tggaacaacc tcaccgatcc caaccagatc 300
agtgtcggcc aggtgctgcg cctgtcgagc tcgggcgccg gcggcgcgca gaccacgccg 360
gtgacctcct ccaagccgca acccaagccg ctggaccagg gaagcgccga aacgccggcc 420
ggcggcatgg aagccggcgc cggcggcgaa accggcgggg ccaccacccc gcccgcggca 480
acggtgcccg atcccaagcc cgcgcgcgcg gccgatgccg ccgtcatcaa ctggggctgg 540
ccggccaatg gcgccatcct gcagaccttc aacagcaaca ccaagggcat cgacctggcc 600
ggctcgctgg gcgatccggt gatcgcggcg gccgatggca aggtgatgta cagcggcaat 660
ggcgtgcgcg gcctgggcaa cctgatcatc atcaatcacc agaacggctt catcacggcc 720
tacgcgcaca accgcgcgct gctggtcaag accggccaga acgtcaagcg cggggccaag 780
atcgccgaga tcggcgagac cgacaccacg tcgccgcggc tgcatttcga gatccgccgc 840
cagggcacgc cggtcgaccc gatgcagtat ctgccgccgc gatga 885

<210> SEQ ID NO 48
<211> LENGTH: 1416
<212> TYPE: DNA
<213> ORGANISM: Bordetella pertussis

<400> SEQUENCE: 48

| | | | | | |
|---|---|---|---|---|---|
| atgaatcgtg | gccccaacag | tttggtgcgc | agcttcaaac | gcaaagttgc | cgccctgttc | 60 |
| gcccctcctg | tcgaacctac | ctcgcgtggc | ggcgccctgc | tccgccgcac | cctgacagtc | 120 |
| tccgcgctcg | gcctgttcgc | cggcgccgcc | gcgctgggca | tggttcaaca | gcccgaccgc | 180 |
| tccgaacttc | ccccttgcg | cctgatcgac | agcgtcctgc | cgctcgaggc | gggccagatg | 240 |
| caggtcagcg | acgccagcaa | cgcccctat | atcagcgaaa | cccgcatccg | cgccggcgac | 300 |
| accctggccg | ccgtgctgca | gcgcctggac | atcgacagcc | gcggctgca | gaacttcctg | 360 |
| acccacgacg | ccagcgcgcg | cagcatctac | aagctgtacc | cgggccgctc | ggtacaggcc | 420 |
| gccaccaacg | agaacggcga | cctggtctgg | ctgcgctaca | tccacacccc | cggcaacgaa | 480 |
| tccggcgggc | aggtggtcac | gcggctgctg | cacgtggcgc | ccgacggcgc | caacggctac | 540 |
| aaggccgagg | aagtcaccca | gggcaccgaa | caacagaccc | gcgtcgcggt | cggcaccatc | 600 |
| cgctcctcgc | tgttcggtgc | caccgacgcg | gcgggcatcc | ccgactcggt | caccatgcag | 660 |
| atggccgaca | tcctcagctc | caagatcgac | ttcctgcgcg | acctgcgcca | gggcgaccag | 720 |
| ttccgcgtgg | tgtacgaggt | ccgcacccac | gaaggccgct | atgcgggcgc | cgggcgcgtg | 780 |
| caggcgctgg | aattcatcaa | cggcgacaag | acctacaacg | ccgtctggtt | cagcccggac | 840 |
| ggcaagagcg | gctcctacta | cgacttcgac | ggaaccagcc | tgcgcggcgc | cttcctgcgt | 900 |
| accgccctga | agttcagccg | catcagctcg | accttcggca | tgcgcatgca | tcccatccac | 960 |
| aagacctgga | ccggccacaa | gggcgtcgat | tacgcggccc | ccacgggcac | ccgatccac | 1020 |
| gccacggccg | acgcacggt | ggagttcgcg | ggctggcaga | acggctacgg | caatgtggtc | 1080 |
| atcatcaagc | accacggcaa | gtactcgacg | ctgtacgccc | ccagagccg | catcgcctcc | 1140 |
| ggcctcaaga | aaggccagaa | aatcgcccag | ggcgaactgg | tcggctacgt | cggctcgacc | 1200 |
| ggctgggcca | ccggcccgca | cctgcactac | gagttccgcg | tcaacaacca | gccgatcgac | 1260 |
| ccgctcgcgg | tcgacctgcc | ggtggcgcgc | aagctggaac | ccgccgaact | gcgcgccttc | 1320 |
| acgcaggcgg | tgcagccgta | caagcagcag | atcaagctgc | tgaccgagtt | ccagcagacc | 1380 |
| ctgccggaag | gctcggccac | cgtggccagc | cgctga | | | 1416 |

<210> SEQ ID NO 49
<211> LENGTH: 1566
<212> TYPE: DNA
<213> ORGANISM: Bordetella pertussis

<400> SEQUENCE: 49

| | | | | | |
|---|---|---|---|---|---|
| atgcgggtcg | cggcgggttt | gctggtgtgg | gcggcggtgg | cggtagcgcc | accggcggcc | 60 |
| tgggcggttt | cggacctggc | gggtcgccag | tccgaagccg | aacgacagca | ggccgcgctg | 120 |
| cgcgaccgca | tcgacgcgct | gcagaaagag | atcgacacgc | gcgaggccgc | cgcaaggag | 180 |
| gccgccgacg | cgttgaagga | atccgaatca | gccatttcgc | gcatcaatct | ccggctgcgt | 240 |
| gaattgggcg | aggccagccg | caaggccgaa | gccgaactcg | ccggcctgga | aaagcaggtg | 300 |
| gtggcgcagc | aggcggtgct | gcaaaagcgc | cgcgccgagc | tggccgacca | gctgcgcacc | 360 |
| cagtacacca | gcggcctgtc | gccctggacg | gccctgctgt | cgggcgacga | cccgcagcag | 420 |
| ctgggccgca | acctgggcta | cctggactat | gtatcgcgcg | cccgcgcgca | ggcggtgcat | 480 |

```
gcgttgcgcg aggatatcgc ccggctcgcg gcgctgcagg ggcaggccga tgcccgccgc      540
gacgacatcc agacgctggt ggccgagacg tccagccaga aggccgcgct ggtcgaacag      600
cagaaaaccc gcgccaccct gttggcgaaa ttagagggac agattgcggc gcaacgcgcc      660
gaggccggca agctgggccg tgacgaccag cggctgtcgc acctgatcga cgacctggga      720
agcgccatcg cgcgccaggc ggaggaagat gcccgccggc gcgccgccga ggaggcccgc      780
cgcaaggaag aggaagcccg ccaggccgag gccgcgcgcc gcgccgaggc ggcgcgccag      840
caggaggcgg cccgtcaggc cgccgcggcc cgcgaggccg acgcccggcg ccaggccgag      900
acggcccgcc aggcgcagca ggcgcgcgat gccgaggcgc gcgacgccgc cgccgcgcgc      960
gagcaggccg aggcggcggc ccgccagggg cgcggcccgg tggcgctggc cgaccctgac     1020
gccgctggcc tgcgccaggt cgagggcggc cggctggtcg atccgcaggc cgcgccgccg     1080
cgcgaaaccc gcccggcggc tcgcgccgaa ccggccgagc cggcgccgcg cgaggccgcg     1140
cctgcccgta cggcgtccgc cgccccggtg ggcggcggca atggcctgcg cgcgcgggctg    1200 ccgatgccgg tgcgcgggac gatccagggc cgcttcggcg tcgaccgccc cgatggcggc     1260
gtgtggcgcg ggctggtact gcgcaccgcc gagggcacgc cggtcaaggt ggtggctccc     1320
ggcaccgtgg tctacgccga atggctgagg ggttttggca atctcatcat tgtcgaccat     1380
ggacagcagt acctgacggt atacgcttac aaccagagcc tgctcaaacg ggtgggcgac     1440
cgggtggcgc aggcgatac tattgctacg gtaggcgcga ccggcggcca agtggaatcg      1500
ggcctatact ttgaaattcg ccatcgtggc gcaccggtgg acccggccca gtggctggcc     1560
caataa                                                               1566

<210> SEQ ID NO 50
<211> LENGTH: 744
<212> TYPE: DNA
<213> ORGANISM: Bordetella pertussis

<400> SEQUENCE: 50
gtgccccgaa tcgcgtgttc ccgccagcca tccgagccct cggcggccgg agggcggctg       60
tggcgcccgt tgcgcgcgct gctggcgcg ctggccctgg cgctgctggc cgcgtgcgga      120
tcgacctcgg gcggcagcgg cggcgccttc taccgcgtgc aaagcggcga cacgctgcac      180
agcatcgcgc gcaagcatgg ccagagcgtc ggcgacctgg tgcgctggaa caagctggcc      240
aacgccaacc gcatcgagaa ggggcagttg ctgcgcgtca agccgccggg cacgggcggc      300
agcgccagcc cgccgccgcg cgcggccagc ggcaagagcg ccggcggggc gcccgccaag      360
ccggccgcgc cgatacgcgg cattacgctg atatggccgg ccgacggcaa ggtcacgcgc      420
caattcaacg gctccagcgt cctgggcatc accatcgcca acagcgccgg cgcgtcggtg      480
gtggcggccg cgggcggcac ggtcgcctac gccagcaatg gcttgcgcgg ctacggcaac      540
ctggtcatcg tgccgcacga cggcagcttc ctgaccatct acgcgcacaa ccgcaaactg      600
ctggtcaagc agggccagcg cgtgtcgcaa ggccagcgga tcgccgagat gggcgacacc      660
gacagcagcc aggtcaacct gtatttcgaa ttgcgccgcg acggcaaggc cgtcaacccc      720
gccggcgcct tgccccgccg ctga                                            744

<210> SEQ ID NO 51
<211> LENGTH: 930
<212> TYPE: DNA
<213> ORGANISM: Bordetella pertussis

<400> SEQUENCE: 51
```

```
ttgctggtgg cgcgccacctt gctgaccgcc gccatcgtgg gcgcggccgt gcaacgctat      60
atgtccccgt cggctccggc cgcgtacgcg gtcgattggc ctgcctacgc ccaggccgtc     120
agccccgacc gggatacggc gttcgtgcgt gagaacgtta ccatgcttgc caccaaggtc     180
ggcacgctgc aggccaagct ggccagtatc gacgggctgg ggcggcgcgt ggcccaggtg     240
gccggggtcg cctataccga cccggaactg ccacccagc tgcagggcat gcccgaggaa      300
gccacccacg tgatggatga cctgttcacc gaccggcagc gccgtcgcc ggccacggcc      360 gccgacctgg cgcagcagct cgacgagatc caggtacgca tggcgcagca ggccgacaac     420
ctgcggctgc tggatgcagc cctgacgcgc cgttccgcgg acaaggcgct gctgccttcg     480
gccatgccca tcactgaata cccctacctc agttcatcgt atggctggcg ccgcaacccg     540
gtgacgggcc gctacgccat gcacgaaggg ctcgatttct cggcgcccag cggcacgccc     600
atcctggcgg cgtcgggggg cgtggtgctg gtggccaaat accagagcgg ctacggcaac     660
agcgtggaaa tcgaccacgg caacggcctg atcacacgtt acgcccacgc tcgcgcctg      720 ctggtcaagc cgggcgacgt ggtcgagcgc ggccaggaga tcgcccgcgt gggctcgtcg     780
ggccgttcca ccgggccgca cctgcatttc gaggtgcggc tggccggcca gccgctggat     840
ccgcgcctgt tcctggggcc ccagcagacg gcgccgccca ccgtggccca ggcgccagcc     900
acggcgcccg cggcttcggc gacccgctga                                       930

<210> SEQ ID NO 52
<211> LENGTH: 861
<212> TYPE: DNA
<213> ORGANISM: Bordetella pertussis

<400> SEQUENCE: 52
gtgagcgcgg ccgcccgcct gtggcgcggc gcctggctgg cgctggccct gctggccgcc      60
cagggcgcgc aggcacaggg ctacatcagc cgcaagctga gcgcgccggt gcccggcggg     120
gtggccgtgg tggacctggg gcaggccgcc caggcgccgg aggtcacgta ccgcggccgt     180
cccgtcatgg tgctgcgcga agccgacggc ccgtggatcg ccgtggtcgg cattccgctg     240
gcggccaggc ccgcagcga ggcgatctcg gtgcggggtt ccgcggcgc ggtgcgcagc       300 attgcattcg atatcggcgc caaaaagtac acggcccagc acatcaagct gaagaaccag     360
cggcaggtca cgcccaatcc ggacgacctc aagcgcatcg agcgcgaact ggccgagcag     420
acggacgcct atcgcatctt ccgggccggc gtcacgccca gcaacgtgct gctggaccgc     480
ccggtgccgg gccggctgtc cagcccgttc ggcctgcgcg gcttttttcaa cggccaggag     540 cgcaacccgc attccgggct ggatttcgcc gccgccgcgg gcacgccgat caaggcgccg     600
gcggccgggc gcgtcgtgct ggtggcgat tacttcttca acggcaggac ggtgttcgtc      660
gaccacgggc agggcttcat cagcatgttc tgccacatgt cggagatcga cgtgaaggtg     720
ggcgacgaag tgccgcgcgg cggggtggtg gcaaggtgg cgccaccgg gcgcgccacc       780 gggccgcatc tgcactggaa catcagcctg aacgacgcgc gcgtcgatcc ggccatcttc     840
atcggggcgt tcaagcccta g                                               861

<210> SEQ ID NO 53
<211> LENGTH: 294
<212> TYPE: PRT
<213> ORGANISM: Bordetella pertussis

<400> SEQUENCE: 53
```

```
Met Leu Asn Gly Gln Leu Gln Leu Thr Glu Ser Gln Ser Val Ala Gly
1               5                   10                  15

Ala Ser Ala Ala Ala Ala Ser Arg Pro Val Leu Trp Ala Gly Val Leu
            20                  25                  30

Ala Ile Ala Leu Leu Ala Gly Cys Ala Ser Lys Gly Pro Arg Ala Pro
        35                  40                  45

Val Val Asp Leu Thr Gly Gln Pro Gly Ala Ser Gly Pro Thr Asp Gly
    50                  55                  60

Ser Tyr Val Val Lys Pro Gly Asp Thr Leu Tyr Lys Ile Ala Arg Ala
65                  70                  75                  80

Asn Asn Val Asp Ile Glu Asn Leu Lys Arg Trp Asn Asn Leu Thr Asp
                85                  90                  95

Pro Asn Gln Ile Ser Val Gly Gln Val Leu Arg Leu Ser Ser Ser Gly
            100                 105                 110

Ala Gly Gly Ala Gln Thr Thr Pro Val Thr Ser Ser Lys Pro Gln Pro
        115                 120                 125

Lys Pro Leu Asp Gln Gly Ser Ala Glu Thr Pro Ala Gly Gly Met Glu
    130                 135                 140

Ala Gly Ala Gly Gly Glu Thr Gly Gly Ala Thr Thr Pro Pro Ala Ala
145                 150                 155                 160

Thr Val Pro Asp Pro Lys Pro Ala Arg Ala Ala Asp Ala Ala Val Ile
                165                 170                 175

Asn Trp Gly Trp Pro Ala Asn Gly Ala Ile Leu Gln Thr Phe Asn Ser
            180                 185                 190

Asn Thr Lys Gly Ile Asp Leu Ala Gly Ser Leu Gly Asp Pro Val Ile
        195                 200                 205

Ala Ala Ala Asp Gly Lys Val Met Tyr Ser Gly Asn Gly Val Arg Gly
    210                 215                 220

Leu Gly Asn Leu Ile Ile Ile Asn His Gln Asn Gly Phe Ile Thr Ala
225                 230                 235                 240

Tyr Ala His Asn Arg Ala Leu Leu Val Lys Thr Gly Gln Asn Val Lys
                245                 250                 255

Arg Gly Ala Lys Ile Ala Glu Ile Gly Glu Thr Asp Thr Thr Ser Pro
            260                 265                 270

Arg Leu His Phe Glu Ile Arg Arg Gln Gly Thr Pro Val Asp Pro Met
        275                 280                 285

Gln Tyr Leu Pro Pro Arg
    290

<210> SEQ ID NO 54
<211> LENGTH: 471
<212> TYPE: PRT
<213> ORGANISM: Bordetella pertussis

<400> SEQUENCE: 54

Met Asn Arg Gly Pro Asn Ser Leu Val Arg Ser Phe Lys Arg Lys Val
1               5                   10                  15

Ala Ala Leu Phe Ala Pro Pro Val Glu Pro Thr Ser Arg Gly Gly Ala
            20                  25                  30

Leu Leu Arg Arg Thr Leu Thr Val Ser Ala Leu Gly Leu Phe Ala Gly
        35                  40                  45

Ala Ala Ala Leu Gly Met Val Gln Gln Pro Asp Arg Ser Glu Leu Pro
    50                  55                  60

Pro Leu Arg Leu Ile Asp Ser Val Leu Pro Leu Glu Ala Gly Gln Met
65                  70                  75                  80
```

Gln Val Ser Asp Ala Ser Asn Ala Pro Tyr Ile Ser Glu Thr Arg Ile
                    85                  90                  95

Arg Ala Gly Asp Thr Leu Ala Ala Val Leu Gln Arg Leu Asp Ile Asp
                100                 105                 110

Ser Pro Arg Leu Gln Asn Phe Leu Thr His Asp Ala Ser Ala Arg Ser
                115                 120                 125

Ile Tyr Lys Leu Tyr Pro Gly Arg Ser Val Gln Ala Ala Thr Asn Glu
                130                 135                 140

Asn Gly Asp Leu Val Trp Leu Arg Tyr Ile His Thr Pro Gly Asn Glu
145                 150                 155                 160

Ser Gly Gly Gln Val Val Thr Arg Leu Leu His Val Ala Pro Asp Gly
                165                 170                 175

Ala Asn Gly Tyr Lys Ala Glu Glu Val Thr Gln Gly Thr Glu Gln Gln
                180                 185                 190

Thr Arg Val Ala Val Gly Thr Ile Arg Ser Ser Leu Phe Gly Ala Thr
                195                 200                 205

Asp Ala Ala Gly Ile Pro Asp Ser Val Thr Met Gln Met Ala Asp Ile
                210                 215                 220

Leu Ser Ser Lys Ile Asp Phe Leu Arg Asp Leu Arg Gln Gly Asp Gln
225                 230                 235                 240

Phe Arg Val Val Tyr Glu Val Arg Thr His Glu Gly Arg Tyr Ala Gly
                245                 250                 255

Ala Gly Arg Val Gln Ala Leu Glu Phe Ile Asn Gly Asp Lys Thr Tyr
                260                 265                 270

Asn Ala Val Trp Phe Ser Pro Asp Gly Lys Ser Gly Ser Tyr Tyr Asp
                275                 280                 285

Phe Asp Gly Thr Ser Leu Arg Gly Ala Phe Leu Arg Thr Ala Leu Lys
                290                 295                 300

Phe Ser Arg Ile Ser Ser Thr Phe Gly Met Arg Met His Pro Ile His
305                 310                 315                 320

Lys Thr Trp Thr Gly His Lys Gly Val Asp Tyr Ala Ala Pro Thr Gly
                325                 330                 335

Thr Pro Ile His Ala Thr Ala Asp Gly Thr Val Glu Phe Ala Gly Trp
                340                 345                 350

Gln Asn Gly Tyr Gly Asn Val Val Ile Ile Lys His His Gly Lys Tyr
                355                 360                 365

Ser Thr Leu Tyr Ala His Gln Ser Arg Ile Ala Ser Gly Leu Lys Lys
                370                 375                 380

Gly Gln Lys Ile Ala Gln Gly Glu Leu Val Gly Tyr Val Gly Ser Thr
385                 390                 395                 400

Gly Trp Ala Thr Gly Pro His Leu His Tyr Glu Phe Arg Val Asn Asn
                405                 410                 415

Gln Pro Ile Asp Pro Leu Ala Val Asp Leu Pro Val Ala Arg Lys Leu
                420                 425                 430

Glu Pro Ala Glu Leu Arg Ala Phe Thr Gln Ala Val Gln Pro Tyr Lys
                435                 440                 445

Gln Gln Ile Lys Leu Leu Thr Glu Phe Gln Gln Thr Leu Pro Glu Gly
                450                 455                 460

Ser Ala Thr Val Ala Ser Arg
465                 470

<210> SEQ ID NO 55
<211> LENGTH: 521

<212> TYPE: PRT
<213> ORGANISM: Bordetella pertussis

<400> SEQUENCE: 55

```
Met Arg Val Ala Ala Gly Leu Leu Val Trp Ala Ala Val Ala Val Ala
1               5                   10                  15

Pro Pro Ala Ala Trp Ala Val Ser Asp Leu Ala Gly Arg Gln Ser Glu
            20                  25                  30

Ala Glu Arg Gln Gln Ala Ala Leu Arg Asp Arg Ile Asp Ala Leu Gln
        35                  40                  45

Lys Glu Ile Asp Thr Arg Glu Ala Ala Arg Lys Glu Ala Ala Asp Ala
    50                  55                  60

Leu Lys Glu Ser Glu Ser Ala Ile Ser Arg Ile Asn Leu Arg Leu Arg
65                  70                  75                  80

Glu Leu Gly Glu Ala Ser Arg Lys Ala Glu Ala Glu Leu Ala Gly Leu
                85                  90                  95

Glu Lys Gln Val Val Ala Gln Gln Ala Val Leu Gln Lys Arg Arg Ala
            100                 105                 110

Glu Leu Ala Asp Gln Leu Arg Thr Gln Tyr Thr Ser Gly Leu Ser Pro
        115                 120                 125

Trp Thr Ala Leu Leu Ser Gly Asp Asp Pro Gln Gln Leu Gly Arg Asn
    130                 135                 140

Leu Gly Tyr Leu Asp Tyr Val Ser Arg Ala Arg Ala Gln Ala Val His
145                 150                 155                 160

Ala Leu Arg Glu Asp Ile Ala Arg Leu Ala Ala Leu Gln Gly Gln Ala
                165                 170                 175

Asp Ala Arg Arg Asp Asp Ile Gln Thr Leu Val Ala Glu Thr Ser Ser
            180                 185                 190

Gln Lys Ala Ala Leu Val Glu Gln Gln Lys Thr Arg Ala Thr Leu Leu
        195                 200                 205

Ala Lys Leu Glu Gly Gln Ile Ala Ala Gln Arg Ala Glu Ala Gly Lys
    210                 215                 220

Leu Gly Arg Asp Asp Gln Arg Leu Ser His Leu Ile Asp Asp Leu Gly
225                 230                 235                 240

Ser Ala Ile Ala Arg Gln Ala Glu Glu Asp Ala Arg Arg Arg Ala Ala
                245                 250                 255

Glu Glu Ala Arg Arg Lys Glu Glu Glu Ala Arg Gln Ala Glu Ala Ala
            260                 265                 270

Arg Arg Ala Glu Ala Ala Arg Gln Gln Glu Ala Ala Arg Gln Ala Ala
        275                 280                 285

Ala Ala Arg Glu Ala Asp Ala Arg Arg Gln Ala Glu Thr Ala Arg Gln
    290                 295                 300

Ala Gln Gln Ala Arg Asp Ala Glu Ala Arg Asp Ala Ala Ala Ala Arg
305                 310                 315                 320

Glu Gln Ala Glu Ala Ala Ala Arg Gln Gly Arg Gly Pro Val Ala Leu
                325                 330                 335

Ala Asp Pro Asp Ala Ala Gly Leu Arg Gln Val Glu Gly Gly Arg Leu
            340                 345                 350

Val Asp Pro Gln Ala Ala Pro Pro Arg Glu Thr Arg Pro Ala Ala Arg
        355                 360                 365

Ala Glu Pro Ala Glu Pro Ala Pro Arg Glu Ala Ala Pro Ala Arg Thr
    370                 375                 380

Ala Ser Ala Ala Pro Val Gly Gly Gly Asn Gly Leu Arg Arg Gly Leu
385                 390                 395                 400
```

```
Pro Met Pro Val Arg Gly Thr Ile Gln Gly Arg Phe Gly Val Asp Arg
            405                 410                 415

Pro Asp Gly Gly Val Trp Arg Gly Leu Val Leu Arg Thr Ala Glu Gly
        420                 425                 430

Thr Pro Val Lys Val Val Ala Pro Gly Thr Val Val Tyr Ala Glu Trp
            435                 440                 445

Leu Arg Gly Phe Gly Asn Leu Ile Ile Val Asp His Gly Gln Gln Tyr
        450                 455                 460

Leu Thr Val Tyr Ala Tyr Asn Gln Ser Leu Leu Lys Arg Val Gly Asp
465                 470                 475                 480

Arg Val Ala Ala Gly Asp Thr Ile Ala Thr Val Gly Ala Thr Gly Gly
                485                 490                 495

Gln Val Glu Ser Gly Leu Tyr Phe Glu Ile Arg His Arg Gly Ala Pro
            500                 505                 510

Val Asp Pro Ala Gln Trp Leu Ala Gln
            515                 520

<210> SEQ ID NO 56
<211> LENGTH: 247
<212> TYPE: PRT
<213> ORGANISM: Bordetella pertussis

<400> SEQUENCE: 56

Met Pro Arg Ile Ala Cys Ser Arg Gln Pro Ser Glu Pro Ser Ala Ala
1               5                   10                  15

Gly Gly Arg Leu Trp Arg Pro Leu Arg Ala Leu Leu Ala Ala Leu Ala
            20                  25                  30

Leu Ala Leu Leu Ala Ala Cys Gly Ser Thr Ser Gly Gly Ser Gly Gly
        35                  40                  45

Ala Phe Tyr Arg Val Gln Ser Gly Asp Thr Leu His Ser Ile Ala Arg
    50                  55                  60

Lys His Gly Gln Ser Val Gly Asp Leu Val Arg Trp Asn Lys Leu Ala
65                  70                  75                  80

Asn Ala Asn Arg Ile Glu Lys Gly Gln Leu Leu Arg Val Lys Pro Pro
                85                  90                  95

Gly Thr Gly Gly Ser Ala Ser Pro Pro Arg Ala Ala Ser Gly Lys
            100                 105                 110

Ser Ala Gly Gly Ala Pro Ala Lys Pro Ala Ala Pro Ile Arg Gly Ile
        115                 120                 125

Thr Leu Ile Trp Pro Ala Asp Gly Lys Val Thr Arg Gln Phe Asn Gly
    130                 135                 140

Ser Ser Val Leu Gly Ile Thr Ile Ala Asn Ser Ala Gly Ala Ser Val
145                 150                 155                 160

Val Ala Ala Ala Gly Gly Thr Val Ala Tyr Ala Ser Asn Gly Leu Arg
                165                 170                 175

Gly Tyr Gly Asn Leu Val Ile Val Arg His Asp Gly Ser Phe Leu Thr
            180                 185                 190

Ile Tyr Ala His Asn Arg Lys Leu Leu Val Lys Gln Gly Gln Arg Val
        195                 200                 205

Ser Gln Gly Gln Arg Ile Ala Glu Met Gly Asp Thr Asp Ser Ser Gln
    210                 215                 220

Val Asn Leu Tyr Phe Glu Leu Arg Arg Asp Gly Lys Ala Val Asn Pro
225                 230                 235                 240

Ala Gly Ala Leu Pro Arg Arg
```

<210> SEQ ID NO 57
<211> LENGTH: 309
<212> TYPE: PRT
<213> ORGANISM: Bordetella pertussis

<400> SEQUENCE: 57

Met Leu Val Gly Ala Thr Leu Leu Thr Ala Ala Ile Val Gly Ala Ala
1 5 10 15

Val Gln Arg Tyr Met Ser Pro Ser Ala Pro Ala Ala Tyr Ala Val Asp
20 25 30

Trp Pro Ala Tyr Ala Gln Ala Val Ser Pro Asp Arg Asp Thr Ala Phe
35 40 45

Val Arg Glu Asn Val Thr Met Leu Ala Thr Lys Val Gly Thr Leu Gln
50 55 60

Ala Lys Leu Ala Ser Ile Asp Gly Leu Gly Arg Arg Val Ala Gln Val
65 70 75 80

Ala Gly Val Ala Tyr Thr Asp Pro Glu Leu Ala Thr Gln Leu Gln Gly
85 90 95

Met Pro Glu Glu Ala Thr His Val Met Asp Asp Leu Phe Thr Asp Arg
100 105 110

Gln Pro Pro Ser Pro Ala Thr Ala Ala Asp Leu Ala Gln Gln Leu Asp
115 120 125

Glu Ile Gln Val Arg Met Ala Gln Gln Ala Asp Asn Leu Arg Leu Leu
130 135 140

Asp Ala Ala Leu Thr Arg Arg Ser Ala Asp Lys Ala Leu Leu Pro Ser
145 150 155 160

Ala Met Pro Ile Thr Glu Tyr Pro Tyr Leu Ser Ser Ser Tyr Gly Trp
165 170 175

Arg Arg Asn Pro Val Thr Gly Arg Tyr Ala Met His Glu Gly Leu Asp
180 185 190

Phe Ser Ala Pro Ser Gly Thr Pro Ile Leu Ala Ala Ser Gly Gly Val
195 200 205

Val Leu Val Ala Lys Tyr Gln Ser Gly Tyr Gly Asn Ser Val Glu Ile
210 215 220

Asp His Gly Asn Gly Leu Ile Thr Arg Tyr Ala His Ala Ser Arg Leu
225 230 235 240

Leu Val Lys Pro Gly Asp Val Val Glu Arg Gly Gln Glu Ile Ala Arg
245 250 255

Val Gly Ser Ser Gly Arg Ser Thr Gly Pro His Leu His Phe Glu Val
260 265 270

Arg Leu Ala Gly Gln Pro Leu Asp Pro Arg Leu Phe Leu Gly Pro Gln
275 280 285

Gln Thr Ala Pro Pro Thr Val Ala Gln Ala Pro Ala Thr Ala Pro Ala
290 295 300

Ala Ser Ala Thr Arg
305

<210> SEQ ID NO 58
<211> LENGTH: 286
<212> TYPE: PRT
<213> ORGANISM: Bordetella pertussis

<400> SEQUENCE: 58

Met Ser Ala Ala Ala Arg Leu Trp Arg Gly Ala Trp Leu Ala Leu Ala

```
            1               5                  10                 15
          Leu Leu Ala Ala Gln Gly Ala Gln Ala Gln Gly Tyr Ile Ser Arg Lys
                          20                  25                 30

Leu Ser Ala Pro Val Pro Gly Gly Val Ala Val Val Asp Leu Gly Gln
                          35                  40                 45

Ala Ala Gln Ala Pro Glu Val Thr Tyr Arg Gly Arg Pro Val Met Val
                          50                  55                 60

Leu Arg Glu Ala Asp Gly Pro Trp Ile Ala Val Val Gly Ile Pro Leu
          65                              70                 75              80

Ala Ala Arg Pro Gly Ser Glu Ala Ile Ser Val Arg Gly Ser Gly Gly
                          85                  90                 95

Ala Val Arg Ser Ile Ala Phe Asp Ile Gly Ala Lys Lys Tyr Thr Ala
                          100                 105                110

Gln His Ile Lys Leu Lys Asn Gln Arg Gln Val Thr Pro Asn Pro Asp
                          115                 120                125

Asp Leu Lys Arg Ile Glu Arg Glu Leu Ala Glu Gln Thr Asp Ala Tyr
                          130                 135                140

Arg Ile Phe Arg Ala Gly Val Thr Pro Ser Asn Val Leu Leu Asp Arg
          145                             150                155             160

Pro Val Pro Gly Arg Leu Ser Ser Pro Phe Gly Leu Arg Arg Phe Phe
                          165                 170                175

Asn Gly Gln Glu Arg Asn Pro His Ser Gly Leu Asp Phe Ala Ala Ala
                          180                 185                190

Ala Gly Thr Pro Ile Lys Ala Pro Ala Gly Arg Val Val Leu Val
                          195                 200                205

Gly Asp Tyr Phe Phe Asn Gly Arg Thr Val Phe Val Asp His Gly Gln
          210                             215                220

Gly Phe Ile Ser Met Phe Cys His Met Ser Glu Ile Asp Val Lys Val
          225                             230                235             240

Gly Asp Glu Val Pro Arg Gly Val Val Lys Val Gly Ala Thr
                          245                 250                255

Gly Arg Ala Thr Gly Pro His Leu His Trp Asn Ile Ser Leu Asn Asp
                          260                 265                270

Ala Arg Val Asp Pro Ala Ile Phe Ile Gly Ala Phe Lys Pro
                          275                 280                285

<210> SEQ ID NO 59
<211> LENGTH: 30
<212> TYPE: DNA
<213> ORGANISM: Artificial Sequence
<220> FEATURE:
<223> OTHER INFORMATION: Primer

<400> SEQUENCE: 59
ccggaattcg cggttgcgcg cgcagggcat                                  30

<210> SEQ ID NO 60
<211> LENGTH: 30
<212> TYPE: DNA
<213> ORGANISM: Artificial Sequence
<220> FEATURE:
<223> OTHER INFORMATION: Primer

<400> SEQUENCE: 60
ggaggatcca cgattctcct gtttgctcaa                                  30

<210> SEQ ID NO 61
```

```
<211> LENGTH: 30
<212> TYPE: DNA
<213> ORGANISM: Artificial Sequence
<220> FEATURE:
<223> OTHER INFORMATION: Primer

<400> SEQUENCE: 61
ggaggatccc gcccacgctc gttttcgacc                                  30

<210> SEQ ID NO 62
<211> LENGTH: 30
<212> TYPE: DNA
<213> ORGANISM: Artificial Sequence
<220> FEATURE:
<223> OTHER INFORMATION: Primer

<400> SEQUENCE: 62
cccaagcttc cacgtcggtc tcgcagtacg                                  30

<210> SEQ ID NO 63
<211> LENGTH: 18
<212> TYPE: DNA
<213> ORGANISM: Artificial Sequence
<220> FEATURE:
<223> OTHER INFORMATION: Primer

<400> SEQUENCE: 63
aacctgggct tgaactcc                                               18

<210> SEQ ID NO 64
<211> LENGTH: 18
<212> TYPE: DNA
<213> ORGANISM: Artificial Sequence
<220> FEATURE:
<223> OTHER INFORMATION: Primer

<400> SEQUENCE: 64
acaccagcca ggtattga                                               18

<210> SEQ ID NO 65
<211> LENGTH: 27
<212> TYPE: DNA
<213> ORGANISM: Artificial Sequence
<220> FEATURE:
<223> OTHER INFORMATION: Primer

<400> SEQUENCE: 65
ccggaattca tcaagaagct gggacgt                                     27

<210> SEQ ID NO 66
<211> LENGTH: 27
<212> TYPE: DNA
<213> ORGANISM: Artificial Sequence
<220> FEATURE:
<223> OTHER INFORMATION: Primer

<400> SEQUENCE: 66
ggaggatcca actttgcgtt tgaagct                                     27

<210> SEQ ID NO 67
<211> LENGTH: 27
<212> TYPE: DNA
<213> ORGANISM: Artificial Sequence
<220> FEATURE:
<223> OTHER INFORMATION: Primer

<400> SEQUENCE: 67
```
ggaggatccc aagcagcaga tcaagct                                              27

<210> SEQ ID NO 68
<211> LENGTH: 27
<212> TYPE: DNA
<213> ORGANISM: Artificial Sequence
<220> FEATURE:
<223> OTHER INFORMATION: Primer

<400> SEQUENCE: 68
cccaagcttg tcggcgtcgt aaggctg                                              27

<210> SEQ ID NO 69
<211> LENGTH: 27
<212> TYPE: DNA
<213> ORGANISM: Artificial Sequence
<220> FEATURE:
<223> OTHER INFORMATION: Primer

<400> SEQUENCE: 69
ccggaattct ggaaaaccgt ttcacgg                                              27

<210> SEQ ID NO 70
<211> LENGTH: 27
<212> TYPE: DNA
<213> ORGANISM: Artificial Sequence
<220> FEATURE:
<223> OTHER INFORMATION: Primer

<400> SEQUENCE: 70
ggaggatccg aatcagtcct ttttcgc                                              27

<210> SEQ ID NO 71
<211> LENGTH: 27
<212> TYPE: DNA
<213> ORGANISM: Artificial Sequence
<220> FEATURE:
<223> OTHER INFORMATION: Primer

<400> SEQUENCE: 71
ggaggatcca taaatatcgg gaagtgt                                              27

<210> SEQ ID NO 72
<211> LENGTH: 27
<212> TYPE: DNA
<213> ORGANISM: Artificial Sequence
<220> FEATURE:
<223> OTHER INFORMATION: Primer

<400> SEQUENCE: 72
cccaagcttc cgagttcctt cagatgg                                              27

<210> SEQ ID NO 73
<211> LENGTH: 27
<212> TYPE: DNA
<213> ORGANISM: Artificial Sequence
<220> FEATURE:
<223> OTHER INFORMATION: Primer

<400> SEQUENCE: 73
ccggaattcc atgatgccga cttgcat                                              27

<210> SEQ ID NO 74
<211> LENGTH: 27
<212> TYPE: DNA

```
<213> ORGANISM: Artificial Sequence
<220> FEATURE:
<223> OTHER INFORMATION: Primer

<400> SEQUENCE: 74
ggaggatcct gaaagaggca gcaaaac                                              27

<210> SEQ ID NO 75
<211> LENGTH: 27
<212> TYPE: DNA
<213> ORGANISM: Artificial Sequence
<220> FEATURE:
<223> OTHER INFORMATION: Primer

<400> SEQUENCE: 75
ggaggatccc cggcgaaaca gcacgta                                              27

<210> SEQ ID NO 76
<211> LENGTH: 27
<212> TYPE: DNA
<213> ORGANISM: Artificial Sequence
<220> FEATURE:
<223> OTHER INFORMATION: Primer

<400> SEQUENCE: 76
cccaagctta gttcgaagct ggcattg                                              27

<210> SEQ ID NO 77
<211> LENGTH: 27
<212> TYPE: DNA
<213> ORGANISM: Artificial Sequence
<220> FEATURE:
<223> OTHER INFORMATION: Primer

<400> SEQUENCE: 77
ccggaattct tgccgatatc ggttttc                                              27

<210> SEQ ID NO 78
<211> LENGTH: 27
<212> TYPE: DNA
<213> ORGANISM: Artificial Sequence
<220> FEATURE:
<223> OTHER INFORMATION: Primer

<400> SEQUENCE: 78
ggaggatcct tgcatcctgt tatttga                                              27

<210> SEQ ID NO 79
<211> LENGTH: 27
<212> TYPE: DNA
<213> ORGANISM: Artificial Sequence
<220> FEATURE:
<223> OTHER INFORMATION: Primer

<400> SEQUENCE: 79
ggaggatccg ttaaactgga tcgtttc                                              27

<210> SEQ ID NO 80
<211> LENGTH: 27
<212> TYPE: DNA
<213> ORGANISM: Artificial Sequence
<220> FEATURE:
<223> OTHER INFORMATION: Primer

<400> SEQUENCE: 80
cccaagcttt cgaagccgaa ttcgtta                                              27
```

<210> SEQ ID NO 81
<211> LENGTH: 27
<212> TYPE: DNA
<213> ORGANISM: Artificial Sequence
<220> FEATURE:
<223> OTHER INFORMATION: Primer

<400> SEQUENCE: 81
ccggaattca gcagatgcgc cagatca                                27

<210> SEQ ID NO 82
<211> LENGTH: 27
<212> TYPE: DNA
<213> ORGANISM: Artificial Sequence
<220> FEATURE:
<223> OTHER INFORMATION: Primer

<400> SEQUENCE: 82
ggaggatcct tgcgtcggtc ttgccct                                27

<210> SEQ ID NO 83
<211> LENGTH: 27
<212> TYPE: DNA
<213> ORGANISM: Artificial Sequence
<220> FEATURE:
<223> OTHER INFORMATION: Primer

<400> SEQUENCE: 83
ggaggatcct tcggcgtatt gcagttc                                27

<210> SEQ ID NO 84
<211> LENGTH: 27
<212> TYPE: DNA
<213> ORGANISM: Artificial Sequence
<220> FEATURE:
<223> OTHER INFORMATION: Primer

<400> SEQUENCE: 84
cccaagcttt gagtacctgc ctatcgt                                27

<210> SEQ ID NO 85
<211> LENGTH: 433
<212> TYPE: PRT
<213> ORGANISM: Haemophilus influenzae

<400> SEQUENCE: 85

Ser Glu Glu Asn Pro Ile Phe Ser Thr Ser Asp Ser Gly Glu Tyr His
1               5                   10                  15

Glu Leu Asn Thr Ser Pro Asn Lys Asn Ser Thr Ala Leu Gln Pro Asp
            20                  25                  30

Glu Asp Ala Thr Ser Tyr Asp Asp Glu Leu Gln Ala Lys Asp Asp Glu
        35                  40                  45

Val Asp Glu Val Lys Leu Ser Ser Asp Asp Leu Gly Thr Leu Pro Gln
    50                  55                  60

His Ala Gln Asp Ala Leu Asn Gly Leu Leu Asp Ala Ala Asp Gln Ala
65                  70                  75                  80

Ile Arg Ile Thr Asp Gln Phe Ser Tyr Thr Val Thr Glu Gly Asp Thr
                85                  90                  95

Leu Lys Asp Val Leu Val Leu Ser Gly Leu Asp Asp Ser Ser Val Gln
            100                 105                 110

Pro Leu Ile Lys Leu Asp Pro Glu Leu Ala His Leu Lys Ala Gly Gln

```
            115                 120                 125
Gln Phe Tyr Trp Ile Leu Asn Lys Asn Asp Asn Leu Glu Tyr Leu Asn
            130                 135                 140

Trp Leu Val Ser Glu Lys Glu Arg Ile Tyr Glu Arg Leu Glu Asp
145                 150                 155                 160

Gly Lys Phe Lys Arg Gln Val Ile Glu Lys Ser Ile Trp Arg Lys
                    165                 170                 175

Glu Val Leu Lys Gly Glu Ile Gln Asn Ser Leu Asn Ser Ser Leu Arg
                    180                 185                 190

Glu Gln Gly Leu Asp Thr Arg Gln Ile Ser Gln Leu Ser Asn Ala Leu
                    195                 200                 205

Gln Trp Gln Val Ser Leu Arg Lys Leu Lys Lys Gly Thr Gln Phe Ala
            210                 215                 220

Ile Leu Val Ser Arg Glu Tyr Leu Gly Asp Lys Leu Thr Gly Gln Gly
225                 230                 235                 240

Asn Val Glu Ala Leu Arg Ile Ser Ser Gly Gly Lys Asn Tyr Tyr Ala
                    245                 250                 255

Val Gln Ala Ala Asn Gly Arg Tyr Tyr Asn Gln Gln Gly Glu Thr Leu
            260                 265                 270

Gly Lys Gly Phe Ala Arg Tyr Pro Leu Gln Arg Gln Ala Arg Val Ser
                    275                 280                 285

Ser Pro Phe Asn Pro Asn Arg Arg His Pro Val Thr Gly Arg Val Arg
290                 295                 300

Pro His Lys Gly Val Asp Phe Ser Val Ser Gln Gly Thr Pro Val Ile
305                 310                 315                 320

Ala Pro Ala Asp Gly Thr Val Glu Lys Val Ala Tyr Gln Ala Gly Gly
                    325                 330                 335

Ala Gly Arg Tyr Val Met Leu Arg His Gly Arg Glu Tyr Gln Thr Val
                    340                 345                 350

Tyr Met His Leu Ser Lys Ser Leu Val Lys Ala Gly Gln Thr Val Lys
            355                 360                 365

Lys Gly Glu Arg Ile Ala Leu Ser Gly Asn Thr Gly Ile Ser Thr Gly
370                 375                 380

Pro His Leu His Tyr Glu Phe Arg Ile Asn Gly Arg Ala Val Asn Pro
385                 390                 395                 400

Leu Thr Val Lys Leu Pro Gly Thr Ser Ser Gly Met Thr Ser Ala Glu
                    405                 410                 415

Arg Lys Gln Phe Leu Val Arg Val Arg Glu Ala Glu Lys Met Leu Lys
                    420                 425                 430

Pro

<210> SEQ ID NO 86
<211> LENGTH: 390
<212> TYPE: PRT
<213> ORGANISM: Haemophilus influenzae

<400> SEQUENCE: 86

Gly Leu Leu Ile Phe Ser Pro Val Ser Gln Ser Ser Asp Leu Asn Gln
1               5                   10                  15

Ile Gln Lys Gln Ile Lys Gln Glu Ser Lys Ile Glu Lys Gln Lys
                20                  25                  30

Arg Glu Gln Ala Lys Leu Gln Ala Asn Leu Lys Lys His Glu Ser Lys
            35                  40                  45

Ile Asn Thr Val Glu Gly Glu Leu Leu Glu Thr Glu Ile Ser Leu Lys
```

```
                    50                  55                  60
Glu Ile Arg Lys Gln Ile Ala Asp Ala Asp Lys Gln Phe Lys Gln Leu
 65                  70                  75                  80

Glu Lys Gln Glu Arg Glu Gln Lys Ala Arg Leu Ala Lys Gln Met Asp
                     85                  90                  95

Ile Ile Tyr Arg Ser Gly Ile Asn Pro Ser Leu Ile Glu Arg Met Phe
                100                 105                 110

Ala Gln Asp Pro Thr Lys Ala Glu Arg Met Lys Val Tyr Tyr Gln His
                115                 120                 125

Leu Asn Gln Val Arg Ile Glu Met Ile Asp Asn Leu Lys Ala Thr Gln
130                 135                 140

Ala Gln Ile Ala Val Gln Lys Glu Ala Ile Leu Ala Gln Gln Lys Asn
145                 150                 155                 160

His Arg Asn Gln Leu Ser Thr Gln Lys Gln Gln Gln Ala Leu Gln
                165                 170                 175

Lys Ala Gln Gln Glu His Gln Ser Thr Leu Asn Glu Leu Asn Lys Asn
                180                 185                 190

Leu Ala Leu Asp Gln Asp Lys Leu Asn Ala Leu Lys Ala Asn Glu Gln
                195                 200                 205

Ala Leu Arg Gln Glu Ile Gln Arg Ala Glu Gln Ala Ala Arg Glu Gln
210                 215                 220

Glu Lys Arg Glu Arg Glu Ala Leu Ala Gln Arg Gln Lys Ala Glu Glu
225                 230                 235                 240

Lys Arg Thr Ser Lys Pro Tyr Gln Pro Thr Val Gln Glu Arg Gln Leu
                245                 250                 255

Ile Asn Ser Thr Ser Gly Leu Gly Ala Ala Lys Lys Gln Tyr Ser Leu
                260                 265                 270

Pro Val Ser Gly Ser Ile Leu His Thr Phe Gly Ser Ile Gln Ala Gly
                275                 280                 285

Glu Val Arg Trp Lys Gly Met Val Ile Gly Ala Ser Ala Gly Thr Pro
                290                 295                 300

Val Lys Ala Ile Ala Ala Gly Arg Val Ile Leu Ala Gly Tyr Leu Asn
305                 310                 315                 320

Gly Tyr Gly Tyr Met Val Ile Val Lys His Gly Glu Thr Asp Leu Ser
                325                 330                 335

Leu Tyr Gly Phe Asn Gln Ala Val Ser Val Lys Val Gly Gln Leu Val
                340                 345                 350

Ser Ala Gly Gln Val Ile Ala Gln Val Gly Asn Thr Gly Glu Ile Ser
                355                 360                 365

Arg Ser Ala Leu Tyr Phe Gly Ile Ser Arg Lys Gly Thr Pro Val Asn
                370                 375                 380

Pro Ala Gly Trp Val Arg
385                 390

<210> SEQ ID NO 87
<211> LENGTH: 387
<212> TYPE: PRT
<213> ORGANISM: Haemophilus influenzae

<400> SEQUENCE: 87

Thr Ser Asn Phe Pro Ala Pro Ile Ser Asp Ala Asp Gly Asn Leu Ser
 1               5                  10                  15

Pro Ser Val Ile Gln Ser Val Asn Gly Ser Asn Val Gly Gly Ala Trp
                20                  25                  30
```

-continued

```
Gln Pro Glu Ile Gln Lys Asn Ser Leu Pro Thr Thr Gly Asn Met Val
        35                  40                  45

Thr Pro Gln Pro Asn Phe Gln Pro Ile Asn Gln Pro Thr Met Pro
 50                  55                  60

Thr Ala Pro Ala Gln Pro Ala Phe Gln Pro Ser Pro Lys Thr Val Val
 65                  70                  75                  80

Ser Ala Pro Thr Val Gln Thr Lys Thr Val Thr Lys Thr Val Ala Asp
             85                  90                  95

Cys Val Asp Gly Gln His Ile Asn Ile Pro Arg Asn Pro Asn Thr Asn
            100                 105                 110

Val Pro Asp Tyr Ser Lys Ile Ser Lys Gly Ser Tyr Lys Gly Asn Thr
            115                 120                 125

Tyr Lys Val Asn Lys Gly Asp Thr Met Phe Leu Ile Ala Tyr Leu Ala
        130                 135                 140

Gly Ile Asp Val Lys Glu Leu Ala Ala Leu Asn Asn Leu Ser Glu Pro
145                 150                 155                 160

Tyr Asn Leu Ser Leu Gly Gln Val Leu Lys Ile Ser Asn Cys Ser Thr
                165                 170                 175

Lys Thr Val Thr Thr Val Ser Val Lys Gln Pro Ala Val Thr Thr
            180                 185                 190

Ser Thr Ala Thr Pro Val Lys Pro Ala Val Thr Tyr Thr Pro Gly Ala
        195                 200                 205

Asn Gly Thr Gln Ile Gly Ser Asp Gly Thr Ile Ile Gly Pro Ile Lys
        210                 215                 220

Ser Glu Ala Gly Thr Ser Pro Ser Val Pro Val Ala Thr Ser Ser Thr
225                 230                 235                 240

Gln Val Thr Ser Ser Val Asn Asn Ala Asn Ser Thr Pro Ile Asn Ser
                245                 250                 255

Asn Val Val Ala Pro Ile Ala Ser His Val Val Trp Gln Trp Pro Thr
            260                 265                 270

Ser Gly Asn Ile Ile Gln Gly Phe Ser Ser Thr Asp Gly Gly Asn Lys
        275                 280                 285

Gly Ile Asp Ile Ser Gly Ser Arg Gly Gln Ala Val Lys Ala Ala Ala
        290                 295                 300

Ala Gly Arg Ile Val Tyr Ala Gly Asn Ala Leu Arg Gly Tyr Gly Asn
305                 310                 315                 320

Leu Ile Ile Ile Lys His Asn Asp Asp Phe Leu Ser Ala Tyr Ala His
                325                 330                 335

Asn Asp Lys Ile Leu Val Ala Asp Gln Gln Glu Val Lys Ala Gly Gln
            340                 345                 350

Asp Ile Ala Lys Met Gly Ser Ser Gly Thr Asn Thr Val Lys Leu His
            355                 360                 365

Phe Glu Ile Arg Tyr Lys Gly Lys Ser Val Asp Pro Val Arg Tyr Leu
    370                 375                 380

Pro Arg His
385
```

MUTANT BACTERIA FOR PRODUCTION OF GENERALIZED MODULES FOR MEMBRANE ANTIGENS

CROSS-REFERENCE TO RELATED APPLICATIONS

This application is filed pursuant to 35 U.S.C. § 371 as a U.S. National Phase Application of International Patent Application No. PCT/EP2014/0583% filed Apr. 24, 2014, which is a Continuation-in-part of U.S. application Ser. No. 14/396,881, which was filed pursuant to 35 U.S.C. § 371 as a U.S. National Phase Application of International Patent Application No. PCT/EP2013/058459 filed Apr. 24, 2013, the complete contents of each of the above identified applications are hereby incorporated herein by reference for all purposes.

SEQUENCE LISTING

The present application contains a Sequence Listing, which was submitted in ASCII format with International Patent Application No. PCT/EP2014/058396 and is hereby incorporated by reference in its entirety. The ASCII copy is named eolf-seql.txt and is 89,378 bytes in size.

TECHNICAL FIELD

This invention is in the field of vesicles from Gram-negative bacteria, particularly for use in immunogenic compositions, e.g. vaccines.

BACKGROUND ART

Gram-negative bacteria can spontaneously release vesicles from their outer membranes during growth due to the turgour pressure of the cell envelope. The formation of such vesicles can be facilitated by disruption of certain bacterial components e.g. references 1 and 2 disrupted the *E. coli* Tol-Pal system to provide strains which release vesicles into the culture medium during growth. Vesicles can also be produced by disruption of whole bacteria. Known vesicle production methods include methods which use detergent treatment (e.g. with deoxycholate) [3 & 4], detergent-free methods [5], or sonication [6], etc.

These vesicles (which may typically be called blebs and outer membrane vesicles (OMVs)) are rich in immunogenic cell surface-associated, periplasmic and secreted antigens and have been used as vaccines, e.g. against *Neisseria meningitidis* serogroup B [7]. They are particularly suited for this use because the vesicles contain compounds that act as adjuvants, eliciting strong immune responses against the antigens. In this way, the vesicles are a closer mimic of the native bacterium for the immune system than purified antigenic proteins or other bacterial components. However, as the vesicles are derived from bacteria, they typically require treatment to remove reactogenic bacterial components like endotoxin. This may be achieved by detergent treatment etc. [8].

It is an object of the invention to provide further and improved components for preparing these vesicles, and in particular vesicles that can be used as vaccines. One specific object of the invention is to provide a Gram-negative bacterium that is adapted for the production of the vesicles. For example, the bacterium may be adapted to provide a high yield of vesicles, vesicles with altered protein content and/or composition, and vesicles with improved crossprotective efficacy.

In particular in relation to *Haemophilus influenza*, there remains a need for providing a vaccine that protects against a broad spectrum of *Haemophilus influenzae* strains. *H. influenzae* is a versatile microorganism with an improved ability to adapt to new niches and to cause a broad spectrum of disease. Fitness, virulence and colonization factors can change in order to allow the microorganism to adapt to different tissues and hosts. Therefore, potential antigens are subject to high selective pressure and, as a result, may have sequence variability among different strains.

DISCLOSURE OF THE INVENTION

Gram-negative bacteria are separated from the external medium by two successive layers of membrane structures. These structures, referred to as the cytoplasmic membrane and the outer membrane (OM), differ both structurally and functionally. The outer membrane plays an important role in the interaction of pathogenic bacteria with their respective hosts. Consequently, the surface exposed bacterial molecules represent important targets for the host immune response, making outer-membrane components attractive candidates in providing vaccine, diagnostic and therapeutics reagents.

The present invention describes that the mutation or deletion of one or more genes encoding for polypeptides having in common the LytM catalytic domain results in a drastic change in the bacterial cell division and bacterial phenotype. Inventors have also shown that said mutation or deletion results in the release of vesicles known as OMVs or outer membrane vesicles, whereas the same wild type NTHi strains do not normally release OMVs.

The inventors have generated Gram negative bacteria in which the normal expression of proteins containing a LytM catalytic domain is disrupted (i.e. the protein is inactivated) and have observed that these bacteria have properties which can be advantageous in the preparation of vesicles. These properties include an increased tendency to form vesicles and changes in the nature and/or amount of proteins present in the resulting vesicles. It was known in *E. coli* that two components of the division machinery with LytM domains (EnvC and NlpD) are direct regulators of the cell wall hydrolases (amidass) responsible for cell separation (AmiA, AmiB and AmiC) [9]. It is also known that LytM metalloproteases in *E. coli* are absolutely required for daughter cell separation.

In one particularly preferred embodiment it is described that by deleting NT013 and/or NT022 not only the bacterial cell division is affected, but there is also a surprising production and release of outer membrane vesicles (OMVs) in NTHI strains, that normally do not release OMVs.

In particular, it has been shown in non-typeable *Haemophilus influenzae*(NTHi) that deletion of NT013 causes an increase in the release of vesicles, and changes in the protein content and/or composition of the resulting vesicles, e.g. when compared to NHTi without the deletion, as shown in more detail below.

Deletion of NT017 in NTHi causes changes in the protein content and/or composition of the resulting vesicles, e.g. when compared to NHTi without the deletion, as shown in more detail below.

Deletion of NT022 in NTHi causes an increase in the release of vesicles, and changes in the protein content and/or composition of the resulting vesicles, e.g. when compared to NHTi without the deletion, as shown in more detail below.

The growth rate of the mutated bacteria may be comparable to the wild type rate of growth, unlike the growth rate of the known TolR mutant.

The invention therefore provides Gram negative bacteria in which at least one LytM catalytic domain containing protein is inactivated, and methods for preparing vesicles from the bacterium. The invention also provides the vesicles obtained or obtainable from this bacterium and immunogenic compositions comprising these vesicles. The immunogenic compositions may in particular be used as vaccines.

Thus the invention provides a Gram negative bacterium in which at least one LytM catalytic domain containing protein is inactivated. In one embodiment this results in a bacterium which, during growth in culture medium, releases greater quantities of vesicles into the medium and/or vesicles having a different protein composition to the same bacterium in which the LytM catalytic domain containing protein is active. Optionally the at least one LytM catalytic domain containing protein is not expressed.

The invention also provides a Gram negative bacterium in which one or more LytM catalytic domain containing proteins has a modification such that, during growth in culture medium, the bacterium releases greater quantities of vesicles into the medium than the same bacterium lacking the modification and/or vesicles having a different protein content and/or composition to the same bacterium lacking the modification.

In particular, the present invention, also provides a NTHi bacterium in which one or more of the antigens of the invention (e.g. NT013, NT017 and NT022) has/have been knocked out [10]. Techniques for producing knockout bacteria are well known, and knockout of genes from NTHi strains have been reported i.e. in Ref. 11.

The invention also provides a NTHI bacterium in which one or more of the antigens of the invention (e.g. NT013, NT017 and NT022) has a mutation which inhibits its activity. The gene encoding the antigen will have a mutation that changes the encoded amino acid sequence or abolishes its expression. Mutation may involve deletion, substitution, and/or insertion, any of which may be involve one or more amino acids.

One embodiment provides deletions of one or more genes coding for antigens of the invention (e.g. NT013, NT017 and NT022).

In one embodiment, the present invention provides NTHI genes codifying for polypeptides that have the LytM catalytic domain. Generally metalloproteases are identified as containing HxH and HxxxD aminoacid domains in their catalytic domains. Preferably, these one or more genes are codifying for any one of NT013, NT022 or NT017.

Preferred embodiments provide NTHI strains wherein the deletions of one or more genes coding for anyone of NT013 or NT022 or NT017. For instance, the genes deleted can be substituted with an antibiotic resistance cassette, such as the erythromycin resistance cassette. It has been found that all the above mentioned polypeptides have in common a LytM catalytic domain and are all metalloproteases.

It has been also found that the LytM domain in NT013 and NT022 is conserved. NT013 catalytic active site is represented by the following aminoacid motifs -HKGD- and -HLH- at the C-terminal portion. of NT022 catalytic active site is represented by the following aminoacid motifs -NKGID- and -KLH- at the C-terminal.

The invention also provides a method of preparing a Gram negative bacterium, comprising a step of modifying gene(s) encoding one or more LytM catalytic domain containing protein such that the modification causes the bacterium, when grown in culture medium, to release greater quantities of vescicles into the medium than the starting bacterium and/or vesicles having a different protein content and/or composition to the starting bacterium. The mutating step may inactivate (e.g. mutate or delete) the gene.

Mutant bacteria of the invention are particularly useful for preparing bacterial outer membrane vesicles which include NTHi antigens (e.g. antigens of the invention (e.g. NT013, NT017 and NT022)), and which can be used as immunogens.

A method for producing a NTHi bacterium overproducing OMVs of the invention is also provided, which method comprises genetically modifying a Gram-negative bacterial strain by one or more of the following processes: (a) engineering the strain to downregulate expression of one or more Tol genes; and (b) mutating one or more gene(s) encoding a protein comprising a peptidoglycan-associated site to attenuate the peptidoglycan-binding activity of the protein(s); (c) by mutation or deletion of one or more genes encoding for polypeptides having in common the LytM catalytic domain. In one particularly preferred embodiment, the NTHi might not express active NT013, NT022 genes and/or any of Tol genes [11], [10]. In one embodiment the modification is mutation or deletion of one or more genes encoding for polypeptides having in common the LytM catalytic domain.

The invention also provides a vesicle isolated or obtainable from a bacterium of the invention, e.g. using any methods referred to herein. These vesicles are useful as components of vaccines.

The invention also provides a process for preparing a Gram negative bacterial, e.g. NTHi vesicle, comprising a step of treating a Gram negative, e.g NTHi bacterium of the invention such that its outer membrane forms vesicles.

The invention also provides a process for preparing a Gram negative bacterial, e.g NTHi vesicle, comprising a step of culturing a Gram negative, e.g NTHi bacterium of the invention under conditions in which its outer membrane spontaneously sheds vesicles.

The invention also provides a process for preparing vesicles, comprising a step of separating the vesicles from a culture medium comprising bacteria of the invention which have been grown under conditions which permit the release of vesicles into the medium by the bacteria. Vesicles prepared by this process can be used as components of pharmaceutical compositions including vaccines.

The invention also provides a culture medium comprising bacteria of the invention which have been grown under conditions which permit the release of vesicles into the medium by the bacteria. Vesicles may be purified from this culture medium.

The invention also provides a composition comprising vesicles that, during culture of bacteria of the invention, are released into the culture medium. This composition does not comprise any living and/or whole bacteria. This composition and/or its components can be used for vaccine preparation.

Pharmaceutical compositions comprising vesicles of the invention can be used in medicine, e.g. in methods of treating or preventing infection and in methods for raising an antibody response.

The invention also provides a composition comprising vesicles, wherein the vesicles are present in the filtrate obtainable after filtration through a 0.22 μm filter of a culture medium in which a bacterium of the invention has been grown. This composition and/or its components can be used for vaccine preparation.

LytM Domain Containing Proteins

According to the invention, one or more LytM domain containing protein is modified in a Gram negative bacterium. Typically this is inactivation (e.g. by mutation or deletion). This may cause the bacterium to release during growth in culture medium (i) greater quantities of vesicles, and/or (ii) vesicles having a different protein content and/or composition, than the same bacterium in which the LytM catalytic domain containing protein is active. Various modifications can be made.

Metalloproteases of the lysostaphin-type (LytM) of peptidases are widely distributed, occurring in bacteriophages, in Gram-positive and in Gram-negative bacteria. Metalloproteases containing the catalytic LytM domain belong to the M23 peptidase family [12], this domain was identified for the first time in a secreted autolysin from *Staphylococcus aureus* [13].

LytM domains, and hence LytM domain containing protein can in general be identified on the basis of sequence identity with LytM domains from known LytM domain containing proteins such as EnvC, NlpD and YebA of *E. coli* NT013 NT017 or NT022 of non-capsulated (non-typeable) *Haemophila influenza*.

A LytM domain thus typically has at least 30, 40, 50, 55, 60, 65, 70, 75, 80, 85, 90, 95, 96, 97, 98, 99% sequence identity with the sequence of any of the LytM domains referred to herein. A LytM domain containing protein contains a LytM domain. Exemplary sequences for LytM domains and LytM domain containing proteins are provided below.

| LytM catalytic domain containing Protein | Sequence and SEQ ID NO for protein | Sequence and SEQ ID NO for LytM catalytic domain |
|---|---|---|
| *H. influenzae* NT013 (annotated as NTHI0532 in genome 86-208NP) | MPVQHVKLARDRRKKRTYIKVGVFFVAILLILTGIL LTIKDKSEENPIFSTSDSGEYHELNTSPNKNSTALQ PDEDATSYDDELQAKDDEVDEVKLSSDDLGTLPQHA QDALNGLLDAADQAIRITDQFSYTVTEGDTLKDVLV LSGLDDSSVQPLIKLDPELAHLKAGQQFYWILNKND NLEYLNWLVSEKEERIYERLEDGKFKRQVIEKKSIW RKEVLKGEIQNSLNSSLREQGLDTRQISQLSNALQW QVSLRKLKKGTQFAILVSREYLGDKLTGQGNVEALR ISSGGKNYYAVQAANGRYYNQQGETLGKGFARYPLQ RQARVSSPFNPNRRHPVTGRVRPHKGVDFSVSQGTP VIAPADGTVEKVAYQAGGAGRYVMLRHGREYQTVYM HLSKSLVKAGQTVKKGERIALSGNTGISTGPHLHYE FRINGRAVNPLTVKLPGTSSGMTSAERKQFLVRVRE AEKMLKP (SEQ ID NO: 1) | RPHKGVDFSVSQGTPVIAPADG TVEKVAYQAGGAGRYVMLRHGR EYQTVYMHLSKSLVKAGQTVKK GERIALSGNTGISTGPHLHYEF RINGRAVNP (SEQ ID NO: 2) |
| *H. influenzae* NT017 (annotated as NTHI0915 in genome 86-028NP) and | MLRFGVNQKTSLLLTALLSCGLLIFSPVSQSSDLNQ IQKQIKQQESKIEKQKREQAKLQANLKKHESKINTV EGELLETEISLKEIRKQIADADKQFKQLEKQEREQK ARLAKQMDIIYRSGINPSLIERMFAQDPTKAERMKV YYQHLNQVRIEMIDNLKATQAQIAVQKEAILAQQKN HRNQLSTQKKQQQALQKAQQEHQSTLNELNKNLALD QDKLNALKANEQALRQEIQRAEQAAREQEKREREAL AQRQKAEEKRTSKPYQPTVQERQLINSTSGLGAAKK QYSLPVSGSILHTFGSIQAGEVRWKGMVIGASAGTP VKAIAAGRVILAGYLNGYGYMVIVKHGETDLSLYGF NQAVSVKVGQLVSAGQVIAQVGNTGEISRSALYFGI SRKGTPVNPAGWVR (SEQ ID NO: 3) | VRWKGMVIGASAGTPVKAIAAG RVILAGYLNGYGYMVIVKAGET DLSLYGFNQAVSVKVGQLVSAG QVIAQVGNTGEISRSALYFGIS RKGTPVNP (SEQ ID NO: 4) |
| *H. influenzae* NT022 (annotated as NTHI0830 in genome 86-028NP) | MKKSFLLLPLSLVVLSACTSNFPAPISDADGNLSPS VIQSVNGSNVGGAWQPEIQKNSLPTTGNMVTPQPNF QPINQQPTMPTAPAQPAFQPSPKTVVSQPTVQTKTV TKTVADCVDGQHINIPRNPNTNVPDYSKISKGSYKG NTYKVNKGDTMFLIAYLAGIDVKELAALNNLSEPYN LSLGQVLKISNCSTKTVTTTVSVKQPAVTTSTATPV KPAVTYTPGANGTQIGSDGTIIGPIKSEAGTSPSVP VATSSTQVTSSVNNANSTPINSNVVAPIASHVVWQW PTSGNIIQGFSSTDGGNKGIDISGSRGQAVKAAAAG RIVYAGNALRGYGNLIIIKHNDDFLSAYAHNDKILV ADQQEVKAGQDIAKMGSSGTNTVKLHFEIRYKGKSV DPVRYLPRH (SEQ ID NO: 5) | GGNKGIDISGSRGQAVKAAAAG RIVYAGNALRGYGNLIIIKHND DFLSAYAHNDKILVADQQEVKA GQDIAKMGSSGTNTVKLHFEIR YKGKSVDP (SEQ ID NO: 6) |
| *E. coli* YebA | MQQIARSVALAFNNLPRPHRVMLGSLTVLTLAVAVWRPYV YHPDATPIVKTIELEQNEIRSLLPEASEPIDQAAQEDEAI PQDELDDKIAGEAGVHEYVVSTGDTLSSILNQYGIDMGDI TQLAAADRELRNLKIGQQLSWTLTADGELQRLTWEVSRRE TRTYDRTAANGFKMTSEMQQGEWVNNLLKGTVGGSFVASA RNAGLTSAEVSAVIKAMQWQMDFRKLKKGDEFAVLMSREM LDGKREQSQLLGVRLRSEGKDYYAIRAEDGKPYDRNGTGL AKGFLRFPTAKQFRISSNFNPRRTNPVTGRVAPHRGVDFA MPQGTPVLSVGDGEVVVAKRSGAAGYYVAIRHGRSYTTRY | PHRGVDFAMPQGTPVLSVGDGEVV VAKRSGAAGYYVAIRHGRSYTTRY MHLRKILVKPGQKVKRGDRIALSG NTGRSTGPHLHYEVWINQQAVNP (SEQ ID NO: 8) |

| LytM catalytic domain containing Protein | Sequence and SEQ ID NO for protein | Sequence and SEQ ID NO for LytM catalytic domain |
|---|---|---|
| | MHLRKILVKPGQKVKRGDRIALSGNTGRSTGPHLHYEVWI NQQAVNPLTAKLPRTEGLTGSDRREFLAQAKEIVPQLRFD (SEQ ID NO: 7) | |
| E. coli EnvC | MTRAVKPRRFAIRPIIYASVLSAGVLLCAFSAHADERDQL KSIQADIAAKERAVRQKQQQRASLLAQLKKQEEAISEATR KLRETQNTLNQLNKQIDEMNASIAKLEQQKAAQERSLAAQ LDAAFRQGEHTGIQLILSGEESQRGQRLQAYFGYLNQARQ ETIAQLKQTREEVAMQRAELEEKQSEQQTLLYEQRAQQAK LTQALNERKKTLAGLESSIQQGQQQLSELRANESRLRNSI ARAEAAAKARAEREAREAQAVRDRQKEATRKGTTYKPTES EKSLMSRTGGLGAPRGQAFWPVRGPTLHRYGEQLQGELRW KGMVIGASEGTEVKAIADGRVILADWLQGYGLVVVVENGK GDMSLYGYNQSALVSVGSQVRAGQPIALVGSSGGQGRPSL YFEIRRQGQAVNPQPWLGR (SEQ ID NO: 9) | LRWKGMVIGASEGTEVKAIADGRV ILADWLQGYGLVVVVEHGKGDMSL YGYNQSALVSVGSQVRAGQPIALV GSSGGQGRPSLYFEIRRQGQAVNP (SEQ ID NO: 10) |
| E. coli NlpD | MSAGSPKFTVRRIAALSLVSLWLAGCSDTSNPPAPVSSVN GNAPANTNSGMLITPPPKMGTTSTAQQPQIQPVQQPQIQA TQQPQIQPVQPVAQQPVQMENGRIVYNRQYGNIPKGSYSG STYTVKKGDTLFYIAWITGNDFRDLAQPNNIQAPYALNVG QTLQVGNASGTPITGGNAITQADAAEQGVVIKPAQNSTVA VASQPTITYSESSGEQSANKMLPNNKPTATTVTAPVTVPT ASTTEPTVSSTSTSTPISTNRWPTEGKVIETFGASEGGNK GIDIAGSKGQAIIATADGRVVYAGNALRGYGNLIIIKHND DYLSAYAHNDTMLVREQQEVKAGQKIATMGSTGTSSTRLH FEIRYKGKSVNPLRYLPQR (SEQ ID NO 11) | GGNKGIDIAGSKGQAIIATADGRV VYAGNALRGYGNLIIIKHNDDYLS AYAHNDTMLVREQQEVKAGQKIAT MGSTGTSSTRLHFEIRYKGKSVNP (SEQ ID NO: 12) |

The antigen NT013 is annotated as TPR repeat-containing protein and also as cytochrome c maturation heme lyase subunit CcmH2. It has been released as NTHI0532 in the strain 86-028NP. NT013 has been annotated as belonging to the metalloprotease protein family and it has a LytM catalytic domain.

The NT013 antigen has a native 42 N-terminal amino acid sequence (amino acids 1 to 42 of SEQ ID NO: 1). The NT013 antigen without the native 42 N-terminal amino acid sequence is represented by SEQ ID NO: 85.

The antigen NT017 has been annotated as survival protein SurA-like protein NTHI0915 in 86-026NP strain.

The NT017 antigen has a native 20 N-terminal amino acid sequence (amino acids 1 to 20 of SEQ ID NO: 3). The NT017 antigen without the native 42 N-terminal amino acid sequence is represented by SEQ ID NO:86.

The antigen NT022 has been annotated as NTHI0830 from strain NP86-028 and identified to be a possible outer membrane antigenic lipoprotein B. It has been cloned and expressed from Fi176 strain. It has been also found to contain a LytM catalytic domain and to be surface exposed and secreted.

The NT022 antigen has a native 18 N-terminal amino acid sequence (amino acids 1 to 18 of SEQ ID NO: 5). The NT022 antigen without the native 18 N-terminal amino acid sequence is represented by SEQ ID NO:87.

Homologues of LytM domain containing proteins are found in various Gram negative bacteria and examples are set out in the table below:

| | NT013 | NT017 | NT022 |
|---|---|---|---|
| Bordetella pertussis | BP2956 | BP0608 | BP1721 |
| Campylobacter jejuni | BN867_12080 | | |
| Escherichia coli | YebA | EnvC | NlpD |
| Helicobacter pylori | HP0506 | | |
| Hemophilus influenzae | NTHI0532 | NTHI0915 | NTHI0830 |
| Klebsiella pneumoniae | CDK77985 | CDK80041 | CDK79716 |
| Legionella pneumophila | lpp0627 | lpp0562 | NlpD |
| Neisseria meningitidis | NMB0315 | NMB1333 | NMB1483 |
| Neisseria gonorrhoeae | NGO1686 | NGO0571 | NGO1056 |
| Proteus mirabilis | PMI1153 | PMI3180 | NlpD |
| Pseudomonas aeruginosa | PA0667 | PA5133 | PA3623 |
| Salmonella typhi | STY2098 | STY4090 | NlpD |
| Serratia marcescens | YebA | SMWW4_v1c47520 | NlpD |
| Shigella flexneri | YebA | YibP | NlpD |
| Vibrio cholerae | EET91248 | EMP89515 | NlpD |
| Yersinia pestis | YPZ3_1762 | nlpD1 | NlpD |

LytM domains may contain the motif HxxxD (SEQ ID NO:13) and/or HxH, e.g. HKGVD (SEQ ID NO: 14), HRGVD (SEQ ID NO: 15), HTGID (SEQ ID NO: 16), HLH. Other specific motifs include NKGVD (SEQ ID NO: 17), TKGID (SEQ ID NO: 18), NKGID (SEQ ID NO: 19), QLH, RLH, KLH, WKGVF (SEQ ID NO: 20), WRGLV (SEQ ID NO: 21), WKGMV (SEQ ID NO: 22), GLY, SLY, ALY.

NTHi antigens i.e. proteins are defined above by reference to naming conventions from the literature e.g. the "NTHI" numbering (from the genome of strain 86-028NP). Such conventions are explained in more detail in reference 14 (particularly Table 1). Thus an exemplary amino acid and nucleotide sequence for any of the antigens i.e. proteins referred to herein can easily be found in public sequence databases for the indicated strains (together with additional information, such as functional annotations), but the invention is not limited to sequences from the 86-028NP strain.

Genome sequences of several other NTHI strains are available (again, see Table 1 of reference 14). Standard search and alignment techniques can be used to identify in any of these (or other) further genome sequences the homolog of any particular sequence given herein. Moreover, the available sequences can be used to design primers for amplification of homologous sequences from other species and strains. Thus the invention is not limited to these specific species and strains or the strains in which the exemplified sequences are found, but rather encompasses such variants and homologs from other Gram negative e.g. NTHI strains and the use of species and strains in which such variants and homologs are found, as well as non-natural variants. In general, suitable variants of a particular SEQ ID NO include its allelic variants, its polymorphic forms, its homologs, its orthologs, its paralogs, its mutants, etc. In embodiments of the invention, a LytM domain containing protein is a homolog, ortholog or paralog of NT013, NT022 or NT017 of NTHi.

Thus, for instance, polypeptides or proteins used with the invention i.e. modified in the course of making the invention may, compared to the SEQ ID NO herein, include one or more (e.g. 1, 2, 3, 4, 5, 6, 7, 8, 9, etc.) amino acid substitutions, such as conservative substitutions (i.e. substitutions of one amino acid with another which has a related side chain). Genetically-encoded amino acids are generally divided into four families: (1) acidic i.e. aspartate, glutamate; (2) basic i.e. lysine, arginine, histidine; (3) non-polar i.e. alanine, valine, leucine, isoleucine, proline, phenylalanine, methionine, tryptophan; and (4) uncharged polar i.e. glycine, asparagine, glutamine, cysteine, serine, threonine, tyrosine. Phenylalanine, tryptophan, and tyrosine are sometimes classified jointly as aromatic amino acids. In general, substitution of single amino acids within these families does not have a major effect on the biological activity. The polypeptides i.e. proteins may also include one or more (e.g. 1, 2, 3, 4, 5, 6, 7, 8, 9, etc.) single amino acid deletions relative to the SEQ ID NO sequences. The polypeptides may also include one or more (e.g. 1, 2, 3, 4, 5, 6, 7, 8, 9, etc.) insertions (e.g. each of 1, 2, 3, 4 or 5 amino acids) relative to the SEQ ID NO sequences.

Similarly, a polypeptide used with the invention i.e. modified in the course of making the invention may comprise an amino acid sequence that:
(a) is identical (i.e. 100% identical) to a sequence disclosed in the sequence listing;
(b) shares sequence identity (e.g. 30%, 40%, 50%, 60%, 70%, 80%, 85%, 90%, 91%, 92%, 93%, 94%, 95%, 96%, 97%, 98%, 99%, 99.5% or more) with a sequence disclosed in the sequence listing;
(c) has 1, 2, 3, 4, 5, 6, 7, 8, 9 or 10 (or more) single amino acid alterations (deletions, insertions, substitutions), which may be at separate locations or may be contiguous, as compared to the sequences of (a) or (b): and/or
(d) when aligned with a particular sequence from the sequence listing using a pairwise alignment algorithm, each moving window of x amino acids from N-terminus to C-terminus (such that for an alignment that extends to p amino acids, where p>x, there are p−x+1 such windows) has at least x·y identical aligned amino acids, where: x is selected from 20, 25, 30, 35, 40, 45, 50, 60, 70, 80, 90, 100, 150, 200; y is selected from 0.50, 0.60, 0.70, 0.75, 0.80, 0.85, 0.90, 0.91, 0.92, 0.93, 0.94, 0.95, 0.96, 0.97, 0.98, 0.99; and if x·y is not an integer then it is rounded up to the nearest integer. The preferred pairwise alignment algorithm is the Needleman-Wunsch global alignment algorithm [15], using default parameters (e.g. with Gap opening penalty=10.0, and with Gap extension penalty=0.5, using the EBLOSUM62 scoring matrix). This algorithm is conveniently implemented in the needle tool in the EMBOSS package [16].

Within group (c), deletions or substitutions may be at the N-terminus and/or C-terminus, or may be between the two termini. Thus a truncation is an example of a deletion. Truncations may involve deletion of up to 40 (or more) amino acids at the N-terminus and/or C-terminus. N-terminus truncation can remove leader peptides e.g. to facilitate recombinant expression in a heterologous host. C-terminus truncation can remove anchor sequences e.g. to facilitate recombinant expression in a heterologous host.

In general, when an antigen comprises a sequence that is not identical to a sequence from the sequence listing such as a NTHI sequence (e.g. when it comprises a sequence listing with <100% sequence identity thereto, or when it comprises a fragment thereof) it is preferred in each individual instance that the antigen can elicit an antibody which recognises the respective NTHI sequence from the sequence listing.

In some embodiments the LytM containing protein is selected from NT013 and NT022 of NTHi or a homolog, ortholog or paralog thereof.

In some embodiments the LytM containing protein is NT017 of NTHi or a homolog, ortholog or paralog thereof.

The Bacterium

The Gram-negative bacterium of the invention is typically a non-capsulated (non-typeable) *Haemophilus influenzae* strain (NTHi). However, it may be a different Gram-negative bacterium, including *Neisseria meningitidis* (especially serogroup B) and *B. pertussis*. In some embodiments the Gram-negative bacterium of the invention is not a non-capsulated (non-typeable) *Haemophilus influenzae* strain.

Exemplary species for use in the invention include species in any of genera *Escherichia*, *Shigella*, *Neissena*, *Moraxella*, *Bordetella*, *Borrelia*, *Brucella*, *Chlamydia*, *Haemophilus*, *Legionella*, *Pseudomonas*, *Yersinia*, *Helicobacter*, *Salmonella*, *Vibrio*, *Campylobacter*, *Klebsiella*, etc. In particular, the bacterium may be a *Shigella* species (such as *S.dysenteriae*, *S.flexneri*, *S.boydii* or *S.sonnei*). Alternatively, it may be a *Neisseria* species, e.g. a non-pathogenic species such as *N.bacilliformis*, *N.cinerea*, *N.elongata*, *N.lavescens*, *N.lactamica*, *N.macacae*, *N.mucosa*, *N.polysaccharea*, *N.sicca* or *N.subflava*, and in particular *N.lactamica*. Alternatively, a pathogenic species of *Neisseria* may be used, e.g. *N.gonorrhoeae* or *N.meningitidis*. In other examples, the bacterium may be *Bordetella pertussis*, *Borrelia burgdorferi*, *Brucella meltensis*, *Brucella ovis*, *Chlamydia psittaci*, *Chlamydia trachomatis*, *Moraxella catarrhalis*, *Haemophilus influenzae* (including non-typeable stains), *Legionella pneumophila*, *Pseudomonas aeruginosa*, *Yersinia enterocolitica*, *Helicobacter pylori*, *Salmonella enterica* (including serovars *typhi* and *typhimurium*, as well as serovars *paratyphi* and *enteritidis*), *Vibrio cholerae*, *Campylobacter jejuni* *Klebsiella pneumoniae*, *Proteus* (e.g. *Proteus mirabilis*), *Citrobacter*, *Serratia* (e.g. *Serratia marcescens*), *Erwinia*, *Pasteurella*, *Yersinia pesti*, *E. coli* etc. Photosynthetic Gram-negative bacteria may also be used. Typically, the bacterium is a competent strain. This feature facilitates genetic modification of the bacterium.

Gram-negative bacteria may be defined on the basis of their shape, as cocci, bacilli or coccobacilli and the bacterium may thus be a Gram-negative coccus, bacillus or coccobacillus.

The Gram-negative bacterium is optionally a proteobacterium, e.g. belonging to a class selected from Alphaproteobacteria, Betaproteobacteria, Gammaproteobacteria, Deltaproteobacteria, Epsilonproteobacteria, or Acidithiobacillia. The Gram-negative bacterium is optionally not belonging to a class selected from Alphaproteobacteria, Betaproteobacteria, Gammaproteobacteria, Deltaproteobacteria, Epsilonproteobacteria, or Acidithiobacillia.

In some embodiments the bacterium colonises humans. In some embodiments the bacterium is pathogenic in humans.

In some embodiments, the bacterium produces vesicles when grown under normal culture conditions.

In other embodiments, the bacterium does not produce vesicles when grown under normal culture conditions.

In some embodiments the bacterium is not of genus *Caulobacter*, e.g. not *Caulobacter crescentus*. In some embodiments the bacterium is not of genus *Escherichia*, e.g. not *E. coli*. In some embodiments the bacterium is not of genus *Helicobacter*, e.g. not *H. pylori*. In some embodiments the bacterium is not of genus *Neisseria* e.g. not *N.gonorrhoeae* or not *N.meningitidis*. In some embodiments the bacterium is not of genus *Yersinia* e.g. not *Yersinia pestis*. In some embodiments the bacterium is not of genus *Yersinia* e.g. not *Yersinia pestis*. In some embodiments the bacterium is not *H somni*.

In some embodiments the bacterium is in class Betaproteobacteria and the LytM containing protein is selected from NT013, NT017 and NT022, optionally selected from NT017 and NT022 of NTNi, or a homolog, ortholog or paralog thereof.

In some embodiments the bacterium is a Gram-negative coccobacillus and the LytM containing protein is selected from NT013, NT017 and NT022, optionally selected from NT013 and NT017 of NTNi, or a homolog, ortholog or paralog thereof.

In some embodiments the bacterium is a Gram-negative coccus and the LytM containing protein is selected from NT013, NT017 and NT022, optionally selected from NT017 and NT022 of NTNi, or a homolog, ortholog or paralog thereof.

When the bacterium is *Neisseria meningitidis* the LytM containing protein may for example be selected from NMB1483, NMB0315 and NMB1333.

When the bacterium is *B. pertussis* the LytM containing protein may for example be selected from BP1721, BP2956, BP0608, BP2919, BP3015 and BP1017.

Other Mutations

In addition to having a disrupted LytM catalytic domain containing protein, a Gram-negative bacterium of the invention can advantageously include one or more further changes relative to a wild-type strain.

These changes can be used e.g. to remove components from the bacterium which would be toxic or undesirable in a human vaccine.

The bacterium may also contain other adaptations for the production of vesicles. In particular, the bacterium typically comprises a genome wherein one or more sequences are present such that, compared to the same bacterium without said sequences(s), the bacterium produces greater quantities of vesicles. Sequences that increase vesicle production may be identified by adding or deleting the sequence to a vesicle-producing strain and determining the effect on vesicle production. Examples include the inactivation or deletion of any of Tol genes [10,11].

For example there may be additional modifications, e.g. knockouts in one or more of lpxL1, lgtB, porA, frpB, synX, lgtA, mltA and/or lst.

In some embodiments a bacterium may include one or more of the knockout and/or hyper-expression mutations disclosed in references 17 and 18-20. Suitable genes for modification include: (a) Cps, CtrA, CtrB, CtrC, CtrD, FrpB, GalE, HtrB/MsbB, LbpA, LbpB, LpxK, Opa, Opc, PilC, PorB, SiaA, SiaB, SiaC, SiaD, TbpA, and/or TbpB [18](b) CtrA, CtrB, CtrC, CtrD, FrpB, GalE, HtrB/MsbB, LbpA, LbpB, LpxK, Opa, Opc, PhoP, PilC, PmrE, PmrF, SiaA, SiaB, SiaC, SiaD, TbpA, and/or TbpB; (c) ExbB, ExbD, rmpM, CtrA, CtrB, CtrD, GalE, LbpA, LpbB, Opa, Opc, PilC, PorB, SiaA, SiaB, SiaC, SiaD, TbpA, and/or TbpB: and (d) CtrA, CtrB, CtrD, FrpB, OpA, OpC, PilC, PorB, SiaD, SynA, SynB, and/or SynC.

A bacterium may have one or more, or all, of the following characteristics: (i) down-regulated or knocked-out LgtB and/or GalE to truncate the LOS; (ii) up-regulated TbpA; (iii) up-regulated NhhA; (iv) up-regulated Omp85; (v) up-regulated LbpA; (vi) up-regulated NspA; (vii) knocked-out PorA; (viii) down-regulated or knocked-out FrpB; (ix) down-regulated or knocked-out Opa; (x) down-regulated or knocked-out Opc; (xii) deleted cps gene complex. A truncated LOS can be one that does not include a sialyl-lacto-N-neotetraose epitope e.g. it might be a galactose-deficient LOS. The LOS may have no α chain.

Such mutations have particularly been described in *Neisseria meningitidis*.

Additional Antigens

Optionally, the bacterium comprises a genome wherein one or more sequences are present such that, compared to the same bacterium without said sequences, the bacterium produces vesicles that comprise one or more additional antigens. These additional antigens are typically not found in the bacterium in its corresponding wild type strain. For example, the additional antigen(s) may be one or more protein antigens from a bacterium selected from *Neisseria meningitidis* (especially serogroup B), pathogenic *E.coli*, *Vibrio cholera*, *Staphylococcus aureus*, *Streptococcus pyogenes* and *Streptococcus agalactiae*. Other suitable bacteria include *Bacillus anthracis*, *Shigella*, *Chlamydia*, *Mycobacterium tuberculosis*, *Mycobacterium leprae*, *Mycobacterium ulcerans*, *Streptococcus*, *Pseudomonas*, *Shigella*, *Campylobacter*, *Salmonella* (e.g. *Salmonella typhimurium*), *Yersinia* (e.g. *Yersinia pestis*), *Rickettsia prowazekii*, *Neisseria*, *Clostridium botulinum* and *Helicobacter*. Similarly, the additional antigen(s) may be one or more viral protein antigens, such as an antigen from a virus of the Adenoviridae, Picornaviridae, Herpesviridae, Hepadnaviridae, Flaviviridae, Retroviridae, Orthomyxoviridae, Paramyxoviridae, Papovaviridae, Rhabdoviridae or Togaviridae family, for example, an antigen from HIV or influenza. The additional antigen(s) may be one or more protein antigens from any pathogen. The additional antigen(s) may also be one or more antigens from cancer cells, e.g. one or more oncoproteins. The vesicles from the bacterium can therefore be used as a delivery system for presenting the additional antigens to the immune system. The one or more sequence(s) present in the genome are therefore capable of directing expression of the additional antigen(s) in the vesicles. The sequence(s) may be integrated into the bacterial chromosome or they may be present in non-integrated genomic element(s), e.g. plasmid (s). For example, it is efficient to include the sequence(s) within one or more expression vector(s) so that it is possible to control expression in the bacterium. For example, each sequence may be in a suitable expression cassette. Typically, the sequences will include genes that encode the additional antigens, together with any regulatory sequences required for effective expression in the vesicles (i.e. promoters, signal sequences, chaperones, secretion pathway machinery etc.). The skilled person is aware of methods for such heterologous gene expression in Gram-negative bacteria, particularly *E. coli*, and also how to direct this expression so that the heterologous proteins are present in the vesicles (see e.g. refs. 21, 22, 23 etc.). For example, the proteins may be fused to appropriate leader peptides for periplasmic compartmentalization. When a protein is targeted to the periplasm in this way, it may be useful to disrupt the vesicles, e.g. using sonication and/or detergent, prior to administration as a vaccine. This helps to release the protein from the vesicle, while retaining the adjuvanticity of the other vesicle components. Similarly, the proteins may be fused to leader sequences followed by a "lipidation box" for compartmentalization in the inner and/or outer membrane as lipoproteins. When a protein is targeted to a membrane in this way, it will typically be orientated either inside or outside the vesicle. This orientation may be changed by the action of endogenous "flip/flop" mechanisms, e.g. in species of *Neisseria*. The proteins may also be fused to transmembrane regions and/or fused to endogenous membrane proteins, e.g. porins, for antigen compartmentalization in the outer membrane. Expression efficiency may also be optimised by modifying codon usage in the sequences to match the preferences of the Gram-negative bacterium (ref. 24).

Preparation of Mutants

Gram-negative bacteria of the invention can be prepared conveniently from wild-type or other starting strains using conventional techniques of mutagenesis. Modification (e.g. inactivation) of the LytM domain containing protein or gene can be achieved in various ways e.g. by deletion or mutation in its promoter, by deletion or mutation of its start codon, by introduction of a premature stop codon, by deletion of the complete or part (e.g. at least 20, 30, 40, 50, 60, 70, 80, 90, 95%) of the coding region, by knockout, etc. Isogenic knockout mutants are preferred. A knockout mutation may be situated in the coding region of the gene or may lie within its transcriptional control regions (e.g. within its promoter). A knockout mutation will reduce the level of mRNA encoding the antigen to <1% of that produced by the wild-type bacterium, preferably <0.5%, more preferably <0.1%, and most preferably to 0%. In the resulting Gram negative bacterium mRNA encoding the desired gene is absent and/or its translation is inhibited (e.g. typically to less than 1% of wild-type levels, preferably <0.5%, more preferably <0.1%, and most preferably to 0%).

A Gram-negative bacterium of the invention may contain a marker gene in the or in place of the inactivated gene e.g. an antibiotic e.g. erythromycin resistance marker. This can be achieved using homologous recombination. Unmarked deletions (i.e. deletion without introduction of a marker gene) may also be used.

In some embodiments, at least one LytM domain containing protein is inactivated, e.g. such that it does not carry out its normal function, or does so at a reduced level. This may arise through reduction in the amount of protein that is expressed and/or by a reduction in the activity of the expressed protein. There may thus be inactivation (e.g. by mutation or a deletion) in the gene encoding the protein. In one embodiment the LytM domain containing protein is expressed at a level of less than 90, 80, 70, 60, 50, 40, 30, 20, 10, 5, 2, 1% of the level at which the unmodified protein is expressed. The LytM domain containing protein may be not expressed. In one embodiment the activity of the expressed LytM domain containing protein is less than 90, 80, 70, 60, 50, 40, 30, 20, 10, 5, 2, 1% of the activity of the unmodified protein). The LytM domain containing protein may be non functional.

In some embodiments, mutations and/or deletion may be made in the LytM domain. Mutations and/or deletions may be chosen which render the LytM domain and/or the LytM domain containing protein non functional, or with a reduced function, as defined above.

Alternatively, the deletion or mutation may reduce the activity or function of the LytM domain containing protein. The deletion or mutation may be in the LytM domain or elsewhere in the protein. For example the deletion or mutation may result in an expressed protein which lacks one or more than one domain (e.g. which lacks the LytM domain). The process of preparing a Gram negative strain, e.g. suitable for vesicle preparation can be followed by a step of culturing the modified bacteria obtained to provide a bacterial culture.

Culture conditions for growing Gram-negative bacteria are well known in the art. For example, they may be grown using an organic nitrogen source (such as amino acid mixtures e.g. containing Ala, Arg, Asn, Asp; casamino acids may be used), glycerol as a carbon source, etc. Inclusion of L-aspartic acid in the medium is particularly useful and may function as both a nitrogen and carbon source.

Methods for Producing the Vesicles

The invention also provides methods for preparing vesicles of the invention, and vesicles obtained or obtainable by these methods. The method comprises a step of obtaining vesicles from a culture of bacteria. The vesicles can be obtained by disruption of or blebbing from the outer membrane of the bacterium to form vesicles therefrom Thus the term "vesicles" typically means OMVs, blebs, microvesicles (MVs [25]) and 'native OMVs' ('NOMVs' [26]). It can typically also mean detergent-extracted OMV (DOMVs) and mutant-derived OMVs (m-OMV). The term "generalized module for membrane antigens" may be used for vesicles obtained from mutant bacteria.

Thus vesicles may be obtained by culturing an appropriate bacterium e.g. the bacterium of the invention under conditions which permit the release of vesicles, and a method of preparing vesicles from the bacterium of the invention thus may comprise or additionally comprise culturing an appropriate bacterium e.g. the bacterium of the invention under conditions which permit the release of vesicles.

Blebs (including MVs) are naturally-occurring membrane vesicles that form spontaneously during bacterial growth and are released into culture medium. Preferably, the vesicles of the invention are blebs because separation of spontaneously-released blebs from the culture medium is more convenient than methods which involve deliberate disruption of the outer membrane (e.g. by detergent treatment or sonication). Moreover, they are substantially free from inner membrane and cytoplasmic contamination. These vesicles typically have a diameter of 35-120 nm or 20-100 nm by electron microscopy e.g. 50 nm diameter and can be purified from the culture medium. The purification ideally involves separating the vesicles from living and/or intact bacteria e.g. by size-based filtration using a filter, such as a 0.22 µm filter, which allows the vesicles to pass through but which does not allow intact bacteria to pass through, or by using low speed centrifugation to pellet cells while leaving the vesicles in suspension. A preferred method involving a two stage size filtration process is described in ref. 27.

Thus, unlike the culture medium, vesicles-containing compositions of the invention will generally be substantially free from whole bacteria, whether living or dead. The size of the vesicles means that they can readily be separated from whole bacteria by filtration e.g. as typically used for filter sterilisation. Although vesicles will pass through a standard 0.22 µm filters, these can rapidly become clogged by other material, and so it may be useful to perform sequential steps of filter sterilisation through a series of filters of decreasing pore size before using a 0.22 µm filter. Examples of preceding filters would be those with pore size of 0.8 µm, 0.45 µm, etc.

In some embodiments OMVs may be prepared artificially from bacteria, and may be prepared using detergent treatment (e.g. with deoxycholate or sarkosyl), or by non-detergent means (e.g. see reference 28). Techniques for forming vesicles include treating bacteria with a bile acid salt detergent (e.g. salts of lithocholic acid, chenodeoxycholic acid, ursodeoxycholic acid, deoxycholic acid, cholic acid, ursocholic acid, etc., with sodium deoxycholate [29 & 30] being preferred for treating Neisseria) at a pH sufficiently high not to precipitate the detergent [31]. Other techniques may be performed substantially in the absence of detergent [28] using techniques such as sonication, homogenisation, microfluidisation, cavitation, osmotic shock, grinding, French press, blending, etc. Methods using no or low detergent can retain useful antigens such as NspA [28]. Thus a method may use an OMV extraction buffer with about 0.5% deoxycholate or lower e.g. about 0.2%, about 0.1%, <0.05% or zero.

A useful process for vesicles preparation is described in reference 32 and involves ultrafiltration on crude OMVs, rather than instead of high speed centrifugation. The process may involve a step of ultracentrifugation after the ultrafiltration takes place.

Thus vesicles may be obtained by treating an appropriate Gram negative bacterium e.g. a bacterium of the invention such that its outer membrane forms vesicles and a method of preparing vesicles from the bacterium of the invention thus may comprise or additionally comprise treating an appropriate Gram negative bacterium e.g. a bacterium of the invention such that its outer membrane forms vesicles.

Release of Greater Quantities of Vesicles

NHTi mutants in which NT013 or NT022 are inactivated have been shown to release greater quantities of vesicles than wild type NTHi.

The bacterium of the invention in one embodiment may release greater quantities of vesicles into the culture medium, compared to the same bacterium in which the LytM catalytic domain containing protein is active. This may be an increase of at least 10, 20, 50, 100, 150, 200, 250, 500, 600, 700, 800, 900, 1000% compared to the same bacterium in which the LytM catalytic domain containing protein is active.

Alternatively stated the invention provides a method of increasing vesicle production from a Gram negative bacterium, e.g. compared to the same bacterium in which the LytM catalytic domain containing protein is active, comprising modifying, e.g. inactivating at least one LytM catalytic domain containing protein in the bacterium. Optionally the bacterium is cultured.

Production of Outer Membrane Vesicles with a Different Protein Composition

NHTi mutants in which at least one LytM catalytic domain containing protein is inactivated have been shown to generate vesicles which have different protein compositions to wild type NTHi.

Specifically, compared to vesicles from wild type NTHi, vesicles from the NT013 mutant may have an increase in the amount of lipoprotein, an increase in the amount of periplasmic protein, a decrease in the amount of outer membrane protein.

Compared to vesicles from wild type NHTi, vesicles from the NT017 mutant may have an increase in the amount of cytoplasmic protein, and a decrease in the amount of outer membrane protein.

Compared to vesicles from wild type NHTi, vesicles from the NT022 mutant may have an increase in the amount of lipoprotein, an increase in the amount of periplasmic protein, a decrease in the amount of outer membrane protein.

Lipoproteins NT069 (annotated as NTHI1957) and NTHI0353 may be found at increased levels in NTHi NT013 and NT022 mutant vesicles, compared to vesicles from wild type NHTi.

The periplasmic serine protease HhoA may be found at increased levels in NTHi NT013 mutant vesicles and/or at decreased levels in NTHi NT017 and NT022 mutant vesicles, compared to vesicles from wild type NHTi.

The outer membrane protein NTHI1668 may be found at increased levels in NTHi NT013, NT017 and NT022 mutant vesicles, compared to vesicles from wild type NHTi. The outer membrane protein P2, which is an abundant and variable protein, is found at decreased levels in NTHi NT013, NT017 and NT022 mutant vesicles, and the level of outer membrane protein P5 also changes compared to vesicles from wild type NHTi. The presence of P2 and P5, which are highly abundant in vesicles is believed to contribute to the lack of crossreactivity in sera generated against haemophilus OMVs and as such the reduction in P2 and/or total P2+P5 may be advantageous. e.g. in producing vesicles with improved crossreactivity.

Thus the vesicles of the invention may contain differences (e.g. increases or decreases. e.g. of at least 10, 20, 50, 100, 150, 200, 250, 500, 600, 700, 800, 900, 1000%) in the total amount of protein, the amount of lipoprotein, the amount of periplasmic protein, the amount of outer membrane protein, and/or the amount of cytoplasmic protein compared to the same bacterium in which the LytM catalytic domain containing protein is active.

Thus the vesicles of the invention may contain differences (e.g. increases or decreases, e.g. of at least 10, 20, 50, 100, 150, 200, 250, 500, 600, 700, 800, 900, 1000% in the amount of one or more proteins e.g. outer membrane proteins selected from (i) NHTi P2, (ii) NHTi P5, and (iii) total NHTi P2+NHTi P5, compared to vesicles from the same bacterium in which the LytM catalytic domain containing protein is active. NTHi P2 and P5 are referred to but if the vesicles are from a different Gram negative bacterium, the P2 or P5 homolog, ortholog or paralog in that bacterium may be increased or decreased.

The invention thus provides a method of altering the total amount of protein, the amount of lipoprotein, the amount of periplasmic protein, the amount of outer membrane protein, and/or the amount of cytoplasmic protein in a vesicle from a Gram negative bacterium, e.g. compared to the same bacterium in which the LytM catalytic domain containing protein is active, comprising modifying, e.g. inactivating at least one LytM catalytic domain containing protein in the bacterium. Optionally the bacterium is cultured. Optionally the outer membrane protein is P2 and/or P5. The alteration may be as defined above.

Immunogenic Compositions and Medicaments

Immunogenic compositions of the invention may be useful as vaccines. Vaccines according to the invention may either be prophylactic (i.e. to prevent infection) or therapeutic (i.e. to treat infection), but will typically be prophylactic.

Compositions may thus be pharmaceutically acceptable. They will usually include components in addition to the antigens e.g. they typically include one or more pharmaceutical carrier(s) and/or excipient(s). A thorough discussion of such components is available in reference 33.

The invention therefore provides a pharmaceutical composition comprising (a) vesicles of the invention and (b) a pharmaceutically acceptable carrier. The composition is suitable for pharmaceutical use. The invention also provides a process for preparing such a composition, comprising the step of admixing vesicles of the invention with a pharmaceutically acceptable carrier. The pharmaceutical composition is preferably an immunogenic composition.

Pharmaceutically acceptable carriers can be any substance that does not itself induce the production of antibodies harmful to the patient receiving the composition, and which can be administered without undue toxicity. Pharmaceutically acceptable carriers can include liquids such as water, saline, glycerol and ethanol. Auxiliary substances, such as wetting or emulsifying agents, pH buffering substances, and the like (e.g. stabilisers, preservatives), can also be present in such vehicles. A thorough discussion of suitable carriers is available in ref. 33.

Compositions will generally be administered to a mammal in aqueous form. Prior to administration, however, the composition may have been in a non-aqueous form. For instance, although some vaccines are manufactured in aqueous form, then filled and distributed and administered also in aqueous form, other vaccines are lyophilised during manufacture and are reconstituted into an aqueous form at the time of use. Thus a composition of the invention may be dried, such as a lyophilised formulation.

The composition may include preservatives such as thiomersal or 2-phenoxyethanol. It is preferred, however, that the vaccine should be substantially free from (i.e. less than 5 μg/ml) mercurial material e.g. thiomersal-free. Vaccines containing no mercury are more preferred. Preservative-free vaccines are particularly preferred.

To improve thermal stability, a composition may include a temperature protective agent. Further details of such agents are provided below.

To control tonicity, it is preferred to include a physiological salt, such as a sodium salt. Sodium chloride (NaCl) is preferred, which may be present at between 1 and 20 mg/ml e.g. about 10±2 mg/ml NaCl.

Other salts that may be present include potassium chloride, potassium dihydrogen phosphate, disodium phosphate dehydrate, magnesium chloride, calcium chloride, etc.

Compositions will generally have an osmolality of between 200 mOsm/kg and 400 mOsm/kg, preferably between 240-360 mOsm/kg, and will more preferably fall within the range of 290-310 mOsm/kg.

Compositions may include one or more buffers. Typical buffers include: a phosphate buffer; a Tris buffer; a borate buffer; a succinate buffer; a histidine buffer (particularly with an aluminum hydroxide adjuvant); or a citrate buffer. Buffers will typically be included in the 5-20 mM range.

The pH of a composition will generally be between 5.0 and 8.1, and more typically between 6.0 and 8.0 e.g. 6.5 and 7.5, or between 7.0 and 7.8.

The composition is preferably sterile. The composition is preferably non-pyrogenic e.g. containing <1 EU (endotoxin unit, a standard measure) per dose, and preferably <0.1 EU per dose. The composition is preferably gluten free.

The composition may include material for a single immunisation, or may include material for multiple immunisations (i.e. a 'multidose' kit). The inclusion of a preservative is preferred in multidose arrangements. As an alternative (or in addition) to including a preservative in multidose compositions, the compositions may be contained in a container having an aseptic adaptor for removal of material.

Human vaccines are typically administered in a dosage volume of about 0.5 ml, although a half dose (i.e. about 0.25 ml) may be administered to children.

Immunogenic compositions of the invention can also comprise one or more immunoregulatory agents. Preferably, one or more of the immunoregulatory agents include one or more adjuvants. The adjuvants may include a TH1 adjuvant and/or a TH2 adjuvant, further discussed below.

Adjuvants which may be used in compositions of the invention include, but are not limited to:

mineral salts, such as aluminium salts and calcium salts, including hydroxides (e.g. oxyhydroxides), phosphates (e.g. hydroxyphosphates, orthophosphates) and sulphates, etc. [e.g. see chapters 8 & 9 of ref. 34];

oil-in-water emulsions, such as squalene-water emulsions, including MF59 (5% Squalene, 0.5% Tween 80, and 0.5% Span 85, formulated into submicron particles using a microfluidizer) (Chapter 10 of ref. 34: see also refs. 35-37, and chapter 12 of ref. 38], complete Freund's adjuvant (CFA) and incomplete Freund's adjuvant (IFA);

saponin formulations [chapter 22 of ref. 34], such as QS21 [39] and ISCOMs [chapter 23 of ref. 34];

virosomes and virus-like particles (VLPs) [40-46];

bacterial or microbial derivatives, such as non-toxic derivatives of enterobacterial lipopolysaccharide (LPS), Lipid A derivatives [47, 48], immunostimulatory oligonucleotides [49-54], such as IC-31™ [55] (deoxynucleotide comprising 26-mer sequence 5'-(IC)$_{13}$-3'(SEQ ID NO: 23) and polycationic polymer peptide comprising 11-mer amino acid sequence KLKLLLLLKLK (SEQ ID NO: 24) and ADP-ribosylating toxins and detoxified derivatives thereof [56-65];

human immunomodulators, including cytokines, such as interleukins (e.g. IL-1,IL-2, IL-4, IL-5, IL-6, IL-7, IL-12 [66, 67], interferons (e.g. interferon-γ), macrophage colony stimulating factor, and tumor necrosis factor;

bioadhesives and mucoadhesives, such as chitosan and derivatives thereof, esterified hyaluronic acid microspheres [68] or mucoadhesives, such as cross-linked derivatives of poly(acrylic acid), polyvinyl alcohol, polyvinyl pyrollidone, polysaccharides and carboxymethylcellulose[69];

microparticles (i.e. a particle of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(α-hydroxy acid), a poyhydroxybutyric acid, a polyorthoester, a polyanhydride, a polycaprolactone, etc.);

liposomes [Chapters 13 & 14 of ref. 34, ref. 70-72];

polyoxyethylene ethers and polyoxyethylene esters [73];

PCPP formulations [74 and 75];

muramyl peptides, including N-acetyl-muramyl-L-threonyl-D-isoglutamine (thr-MDP), N-acetyl-normuramyl-1-alanyl-d-isoglutamine (nor-MDP), and N-acetylmuramyl-1-alanyl-d-isoglutaminyl-1-alanine-2-(1'-2'-dipalmitoyl-sn-glycero-3-hydroxyphosphoryloxy)-ethylamine MTP-PE): and imidazoquinolone compounds, including Imiquamod and its homologues (e.g. "Resiquimod 3M") [76 and 77].

Immunogenic compositions and vaccines of the invention may also comprise combinations of aspects of one or more of the adjuvants identified above. For example, the following adjuvant compositions may be used in the invention: (1) a saponin and an oil-in-water emulsion [78]: (2) a saponin (e.g. QS21)+a non-toxic LPS derivative (e.g. 3dMPL) [79] (3) a saponin (e.g. QS21)+a non-toxic LPS derivative (e.g. 3dMPL)+a cholesterol; (4) a saponin (e.g. QS21)+3dMPL+ IL-12 (optionally+a sterol) [80]; (5) combinations of 3dMPL with, for example, QS21 and/or oil-in-water emulsions [81]; (6) SAF, containing 10% squalne, 0.4% Tween 80™, 5% pluronic-block polymer L121, and thr-MDP, either microfluidized into a submicron emulsion or vortexed to generate a larger particle size emulsion. (7) Ribi™ adjuvant system (RAS), (Ribi Immunochem) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); and (8) one or more mineral salts (such as an aluminum salt)+a non-toxic derivative of LPS (such as 3dMPL).

Other substances that act as immunostimulating agents are disclosed in chapter 7 of ref. 34.

The use of an aluminium hydroxide and/or aluminium phosphate adjuvant is particularly preferred, and antigens are generally adsorbed to these salts. Calcium phosphate is another preferred adjuvant.

Other preferred adjuvant combinations include combinations of Th1 and Th2 adjuvants such as CpG & alum or resiquimod & alum. A combination of aluminium phosphate and 3dMPL may be used (this has been reported as effective in pneumococcal immunisation [82]). The use of an MF59 adjuvant is preferred, in particular in case of IM (intramuscular) or IP (Intraperitoncal) immunization.

The compositions of the invention may elicit both a cell mediated immune response as well as a humoral immune response. This immune response will preferably induce long lasting (e.g. neutralising) antibodies and a cell mediated immunity that can quickly respond upon exposure to NTHI.

Two types of T cells, CD4 and CD8 cells, are generally thought necessary to initiate and/or enhance cell mediated immunity and humoral immunity. CD8 T cells can express a CD8 co-receptor and are commonly referred to as Cytotoxic T lymphocytes (CTLs). CD8 T cells are able to recognized or interact with antigens displayed on MHC Class I molecules.

CD4 T cells can express a CD4 co-receptor and are commonly referred to as T helper cells. CD4 T cells are able to recognize antigenic peptides bound to MHC class I molecules. Upon interaction with a MHC class II molecule, the CD4 cells can secrete factors such as cytokines. These secreted cytokines can activate B cells, cytotoxic T cells, macrophages, and other cells that participate in an immune response. Helper T cells or CD4+ cells can be further divided into two functionally distinct subsets: TH1 phenotype and TH2 phenotypes which differ in their cytokine and effector function.

Activated TH1 cells enhance cellular immunity (including an increase in antigen-specific CTL production) and are therefore of particular value in responding to intracellular infections. Activated TH1 cells may secrete one or more of IL-2, IFN-γ, and TNF-β. A TH1 immune response may result in local inflammatory reactions by activating macrophages, NK (natural killer) cells, and CD8 cytotoxic T cells (CTLs). A TH1 immune response may also act to expand the immune response by stimulating growth of B and T cells with IL-12. TH1 stimulated B cells may secrete IgG2a.

Activated TH2 cells enhance antibody production and are therefore of value in responding to extracellular infections. Activated TH2 cells may secrete one or more of IL-4, IL-5, IL-6, and IL-10. A TH2 immune response may result in the production of IgG1, IgE, IgA and memory B cells for future protection.

An enhanced immune response may include one or more of an enhanced TH1 immune response and a TH2 immune response.

A TH1 immune response may include one or more of an increase in CTLs, an increase in one or more of the cytokines associated with a TH1 immune response (such as IL-2, IFN-γ, and TNF-β), an increase in activated macrophages, an increase in NK activity, or an increase in the production of IgG2a. Preferably, the enhanced TH1 immune response will include an increase in IgG2a production.

A TH1 immune response may be elicited using a TH1 adjuvant. A TH1 adjuvant will generally elicit increased levels of IgG2a production relative to immunization of the antigen without adjuvant. TH1 adjuvants suitable for use in the invention may include for example saponin formulations, virosomes and virus like particles, non-toxic derivatives of enterobacterial lipopolysaccharide (LPS), immunostimulatory oligonucleotides. Immunostimulatory oligonucleotides, such as oligonucleotides containing a CpG motif, are preferred TH1 adjuvants for use in the invention.

A TH2 immune response may include one or more of an increase in one or more of the cytokines associated with a TH2 immune response (such as IL-4, IL-5, IL-6 and IL-10), or an increase in the production of IgG1. IgE, IgA and memory B cells. Preferably, the enhanced TH2 immune response will include an increase in IgG1 production.

A TH2 immune response may be elicited using a TH2 adjuvant. A TH2 adjuvant will generally elicit increased levels of IgG1 production relative to immunization of the antigen without adjuvant. TH2 adjuvants suitable for use in the invention include, for example, mineral containing compositions, oil-emulsions, and ADP-ribosylating toxins and detoxified derivatives thereof. Mineral containing compositions, such as aluminium salts are preferred TH2 adjuvants for use in the invention.

Preferably, the invention includes a composition comprising a combination of a TH1 adjuvant and a TH2 adjuvant. Preferably, such a composition elicits an enhanced TH1 and an enhanced TH2 response, i.e., an increase in the production of both IgG1 and IgG2a production relative to immunization without an adjuvant. Still more preferably, the composition comprising a combination of a TH1 and a TH2 adjuvant elicits an increased TH1 and/or an increased TH2 immune response relative to immunization with a single adjuvant (i.e., relative to immunization with a TH1 adjuvant alone or immunization with a TH2 adjuvant alone).

The immune response may be one or both of a TH1 immune response and a TH2 response. Preferably, immune response provides for one or both of an enhanced TH1 response and an enhanced TH2 response.

The enhanced immune response may be one or both of a systemic and a mucosal immune response. Preferably, the immune response provides for one or both of an enhanced systemic and an enhanced mucosal immune response. Preferably the mucosal immune response is a TH2 immune response. Preferably, the mucosal immune response includes an increase in the production of IgA.

Bacterial infections can affect various areas of the body and so the compositions of the invention may be prepared in various forms. For example, the compositions may be prepared as injectables, either as liquid solutions or suspensions. Solid forms suitable for solution in, or suspension in, liquid vehicles prior to injection can also be prepared (e.g. a lyophilised composition or a spray-freeze dried composition). The composition may be prepared for topical administration e.g. as an ointment, cream or powder. The composition may be prepared for oral administration e.g. as a tablet or capsule, as a spray, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops. The composition may be in kit form, designed such that a combined composition is reconstituted just prior to administration to a patient. Such kits may comprise one or more antigens in liquid form and one or more lyophilised antigens.

Where a composition is to be prepared extemporaneously prior to use (e.g. where a component is presented in lyophilised form) and is presented as a kit, the kit may comprise two vials, or it may comprise one ready-filled syringe and one vial, with the contents of the syringe being used to reactivate the contents of the vial prior to injection.

Immunogenic compositions used as vaccines comprise an immunologically effective amount of antigen(s), as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. Where more than one antigen is included in a composition then two antigens may be present at the same dose as each other or at different doses.

As mentioned above, a composition may include a temperature protective agent, and this component may be particularly useful in adjuvanted compositions (particularly those containing a mineral adjuvant, such as an aluminium salt). As described in reference 83, a liquid temperature protective agent may be added to an aqueous vaccine composition to lower its freezing point e.g. to reduce the freezing point to below 0° C. Thus the composition can be stored below 0° C., but above its freezing point, to inhibit thermal breakdown. The temperature protective agent also permits freezing of the composition while protecting mineral salt adjuvants against agglomeration or sedimentation after freezing and thawing, and may also protect the composition at elevated temperatures e.g. above 40° C. A starting aqueous vaccine and the liquid temperature protective agent may be mixed such that the liquid temperature protective agent forms from 1-80% by volume of the final mixture. Suitable temperature protective agents should be safe for human administration, readily miscible/soluble in water, and should not damage other components (e.g. antigen and adjuvant) in the composition. Examples include glycerin, propylene glycol, and/or polyethylene glycol (PEG). Suitable PEGs may have an average molecular weight ranging from 200-20,000 Da. In a preferred embodiment, the polyethylene glycol can have an average molecular weight of about 300 Da ('PEG-300').

Due to the particulate nature of vesicles a final vaccine product may be a suspension with a cloudy appearance. This appearance means that microbial contamination is not readily visible, and so the vaccine may contain an antimicrobial agent. This is particularly important when the vaccine is packaged in multidose containers. Preferred antimicrobials for inclusion are 2-phenoxyethanol and thimerosal. It is preferred, however, not to use mercurial preservatives (e.g. thimerosal), and it is preferred that the composition contains less than about 25 ng/ml mercury. More preferably, the composition is mercury-free.

Previous work with vesicle vaccines (e.g. for meningococcus) offers pharmaceutical, posological and formulation guidance for administering vesicles. The concentration of vesicles in compositions of the invention will generally be between 10 and 500 µg/ml, preferably between 25 and 200 µg/ml, and more preferably about 50 µg/ml or about 100 µg/ml (expressed in terms of total protein in the vesicles). Lower doses can be effective for seroconversion. Thus the concentration of vesicles in compositions of the invention can be in the range of 1 ng/ml to 10 g/ml, or 1 ng/ml to 1 µg/ml, or 0.5 µg/ml to 50 µg/ml. A dosage volume of 0.5 ml is typical for injection.

The composition may be administered in conjunction with other immunoregulatory agents.

Immunisation

The invention also provides a method for raising an immune response in a mammal comprising the step of administering an effective amount of a composition of the invention. The immune response is preferably protective and preferably involves antibodies and/or cell-mediated immunity. The method may raise a booster response.

The invention also provides compositions of the invention for use in medicine or as a medicament e.g. for use in raising an immune response in a mammal (e.g. as immunogenic compositions or as vaccines).

The immune response may be against Gram negative bacteria.

The invention also provides compositions of the invention in the manufacture of a medicament for raising an immune response in a mammal or for preventing disease in a mammal and the use of vesicles of the invention in the manufacture of a medicament for raising an immune response in a mammal or for preventing disease in a mammal.

By raising an immune response in the mammal by these uses and methods, the mammal can be protected against bacterial, e.g. Gram negative bacteria such as *H. influenzae* infection.

The invention is effective against *H. influenzae* of various different serotypes, but can be particularly useful in protecting against disease resulting from infection by non-typeable *H. influenza* (NTH). In accordance with the invention, an infection may be associated with a disease or condition selected from, for instance, otitis media (including acute otitis media), bronchitis, conjunctivitis, sinusitis, a urinary tract infection, pneumonia, bacteremia, septic arthritis, epiglottitis, pneumonia, empyema, pericarditis, cellulitis, osteomyelitis, lower respiratory tract infection or meningitis. The invention is particularly useful for treating or preventing inflammation of the middle ear or for treating or preventing COPD diseases, by eliciting an immune response that prevents bacteria from moving from the throat to the middle ear via the eustachian tube, where the middle ear is then colonised.

The invention also provides a kit comprising a first component and a second component wherein neither the first component nor the second component is a composition of the invention as described above, but wherein the first component and the second component can be combined to provide a composition of the invention as described above. The kit may further include a third component comprising one or more of the following: instructions, syringe or other delivery device, adjuvant, or pharmaceutically acceptable formulating solution.

The invention also provides a delivery device pre-filled with an immunogenic composition of the invention.

The mammal is preferably a human, e.g. human patient. Where the vaccine is for prophylactic use, the human is preferably a child (e.g. a toddler or infant) or a teenager; where the vaccine is for therapeutic use, the human is preferably a teenager or an adult. A vaccine intended for children may also be administered to adults e.g. to assess safety, dosage, immunogenicity, etc. A mammal (e.g. human, e.g. a patient) may either be at risk from the disease themselves or may be a pregnant female, e.g. woman ('maternal immunisation').

One way of checking efficacy of therapeutic treatment involves monitoring bacterial, e.g. *H. infuenzae* infection after administration of the compositions of the invention. One way of checking efficacy of prophylactic treatment involves monitoring immune responses, systemically (such as monitoring the level of IgG1 and IgG2a production) and/or mucosally (such as monitoring the level of IgA production), against the antigens in the compositions of the invention after administration of the composition. Immunogenicity of compositions of the invention can be determined by administering them to test subjects (e.g. children 12-16 months age, or animal models such as a chinchilla model [84]) and then determining standard parameters including ELISA titres (GMT) of IgG. These immune responses will generally be determined around 4 weeks after administration of the composition, and compared to values determined before administration of the composition. Where more than one dose of the composition is administered, more than one post-administration determination may be made. Typically, antigen-specific serum antibody responses are determined post-immunisation but pre-challenge whereas antigen-specific mucosal antibody responses are determined post-immunisation and post-challenge.

The efficacy of vaccine compositions can also be determined in vivo by immunization studies in animal models of bacterial e.g. *H. influenzae* infection. e.g., guinea pigs Chinchillas, or mice, with the vaccine compositions. One such model is described in reference 85.

Other useful animal model to be used to determine in vivo the efficacy of vaccine compositions of the invention is described in reference 86.

Compositions of the invention will generally be administered directly to a patient. Direct delivery may be accomplished by parenteral injection (e.g. subcutaneously, intraperitoneally, intravenously, intramuscularly, or to the interstitial space of a tissue), or mucosal, such as by rectal, oral, (e.g. tablet, spray), vaginal, topical, transdermal or transcutaneous, intranasal, ocular, aural, pulmonary or other mucosal administration.

The invention may be used to elicit systemic and/or mucosal immunity, preferably to elicit an enhanced systemic and/or mucosal immunity.

Preferably the enhanced systemic and/or mucosal immunity is reflected in an enhanced TH1 and/or TH2 immune response. Preferably, the enhanced immune response includes an increase in the production of IgG1 and/or IgG2a and/or IgA.

Dosage can be by a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc. Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.).

Vaccines prepared according to the invention may be used to treat both children and adults. Thus a human patient may be less than 1 year old, 1-5 years old, 5-15 years old, 15-55 years old, or at least 55 years old. Preferred patients for receiving the vaccines are the elderly (e.g. ≥50 years old, ≥60 years old, and preferably ≥65 years), the young (e.g. ≤5 years old), hospitalised patients, healthcare workers, armed service and military personnel, pregnant women, the chronically ill, or immunodeficient patients. The vaccines are not suitable solely for these groups, however, and may be used more generally in a population.

Vaccines produced by the invention may be administered to patients at substantially the same time as (e.g. during the same medical consultation or visit to a healthcare professional or vaccination centre) other vaccines e.g. at substantially the same time as a measles vaccine, a mumps vaccine, a rubella vaccine, a MMR vaccine, a varicella vaccine, a MMRV vaccine, a diphtheria vaccine, a tetanus vaccine, a pertussis vaccine, a DTP vaccine, a conjugated *H.influenzae* type b vaccine, an inactivated poliovirus vaccine, a hepatitis B virus vaccine, a meningococcal conjugate vaccine (such as a tetravalent A-C-W135-Y vaccine), a respiratory syncytial virus vaccine, etc.

Mucosal Immunisation

The invention provides the compositions of the invention for mucosal immunisation. The invention also provides a method for raising an immune response in a mammal comprising the step of administering an effective amount of such an immunogenic composition to the mammal. The composition is preferably administered via mucosa (to a mucosal surface) e.g. it may be administered intranasal.

A bacterial ADP-ribosylating toxin and or detoxified derivative thereof may be present which may be, for example, derived from *E. coli* heat labile enterotoxin ("LT"). The derivative may have a detoxifying mutation in its A subunit e.g. it may be LT-K63 or LT-R72. In particular it may be LT-K63. In other embodiments, it is not LT-K63.

Intranasal administration of compositions of the invention and a LT-K63 adjuvant is preferred. This may decrease the *H. influenzae* bacterial load in the nasopharynx, lungs and blood, and increase survival rate of infected mammals.

Further Antigenic Components of Compositions of the Invention

The invention also provides compositions further comprising at least one non-typeable *H. infuenzae* antigen or at least one further non-typeable *H. influenzae* antigen.

The invention also provides compositions further comprising at least one antigen that is not a non-typeable *H. influenzae* antigen.

In particular, the invention also provides a composition comprising one or more polypeptides of the invention and one or more of the following further antigens:

an antigen from *N.meningitidis* serogroup A, B, C, W135 and/or Y.

a saccharide or polypeptide antigen from *Streptococcus pneumoniae* [e.g. 87, 88, 89].

an antigen from hepatitis A virus, such as inactivated virus [e.g. 90, 91].

an antigen from hepatitis B virus, such as the surface and/or core antigens [e.g. 91, 92].

a diphtheria antigen, such as a diphtheria toxoid [e.g. chapter 3 of ref. 93] or the $CRM_{197}$ mutant [e.g. 94].

a tetanus antigen, such as a tetanus toxoid [e.g. chapter 4 of ref. 93].

an antigen from *Bordetella pertussis*, such as pertussis holotoxin (PT) and filamentous haemagglutinin (FHA) from *B.pertussis*, optionally also in combination with pertactin and/or agglutinogens 2 and 3 [e.g. refs. 95 & 96].

a whole cellular pertussis antigen a saccharide antigen from *Haemophilus influenzae* B [e.g. 97].

polio antigen(s) [e.g. 98, 99] such as IPV.

measles, mumps and/or rubella antigens [e.g. chapters 9, 10 & 11 of ref. 93].

influenza antigen(s) [e.g. chapter 19 of ref. 93], such as the haemagglutinin and/or neuraminidase surface proteins.

an antigen from *Moraxella catarrhalis* [e.g. 100].

an protein antigen from *Streptococcus agalactiae* (group B streptococcus) [e.g. 101, 102].

a saccharide antigen from *Streptococcus agalactiae* (group B streptococcus).

an antigen from *Streptococcus pyogenes* (group A streptococcus) [e.g. 102, 103, 104].

an antigen from *Staphylococcus aureus* [e.g. 105].

an antigen from Respiratory Syncytial Virus, e.g. a recombinant protein F a vaccine composition comprising diphtheria (D), tetanus (T), pertussis (acellular, component) (Pa), hepatitis B (rDNA)(HBV), poliomyelitis (inactivated)(IPV) and *Haemophilus influenzae* type b (Hib) conjugate vaccine (adsorbed), e.g. Infanrix-hexa The composition may comprise one or more of these further antigens. Combinations with a RSV vaccine and/or with a DTPa-containing vaccine are of particular interest.

Toxic protein antigens may be detoxified where necessary (e.g. detoxification of pertussis toxin by chemical and/or genetic means [96]).

Where a diphtheria antigen is included in the composition it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens. DTP combinations are thus preferred.

Saccharide antigens are preferably in the form of conjugates. Carrier proteins for the conjugates include diphtheria toxin, tetanus toxin, the *N. meningitidis* outer membrane protein [106], synthetic peptides [107,108], heat shock proteins [109,110] pertussis proteins [111,112], protein D from *H.influenzae* [113], cytokines [114], lymphokines [114], streptococcal proteins, hormones [114], growth factors [114], toxin A or B from *C.difficile* [115], iron-uptake proteins [116], etc. A preferred carrier protein is the CRM197 mutant of diphtheria toxin [117].

Antigens in the composition will typically be present at a concentration of at least 1 µg/ml each. In general, the concentration of any given antigen will be sufficient to elicit an immune response against that antigen.

As an alternative to using proteins antigens in the immunogenic compositions of the invention, nucleic acid (preferably DNA e.g. in the form of a plasmid) encoding the antigen may be used.

Antigens are preferably adsorbed to an aluminium salt.

General

The term "comprising" encompasses "including" as well as "consisting" e.g. a composition "comprising" X may consist exclusively of X or may include something additional e.g. X+Y.

The term "about" in relation to a numerical value x is optional and means, for example, x±10%.

The word "substantially" does not exclude "completely" e.g. a composition which is "substantially free" from Y may be completely free from Y. Where necessary, the word "substantially" may be omitted from the definition of the invention.

References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of reference 118. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is well known and is disclosed in reference 119.

BRIEF DESCRIPTION OF DRAWINGS

FIG. 6: Analysis of OMVs. Coomassie stained SDS page gel of OMVs prepared from the wild type, 176ΔNT013 and 176ΔNT022 strains (A). Mass spectrometry identification was performed on selected bands (B). Luciferase assay using HEK293 cells stably expressing NF-iB-luciferase reporter cassette and TLR2 (C) or TLR4/MD2/CD14 (D). The stimulation of TLR receptors is assessed by measuring the NF-xB-induced luciferase activity after 6 hours incubation with serially diluted OMVs. IL-6 and TNFα levels were measured in hPBMCs stimulated (O.N.) with different dilutions of OMVs purified from wt and mutant strains (E-F).

FIG. 16: Multiple alignment for the NlpD homologues.

FIG. 17: Multiple alignment for the YebA homologues.

FIG. 18: Multiple alignment for the EnvC homologues.

MODES FOR CARRYING OUT THE INVENTION

Figure 1:
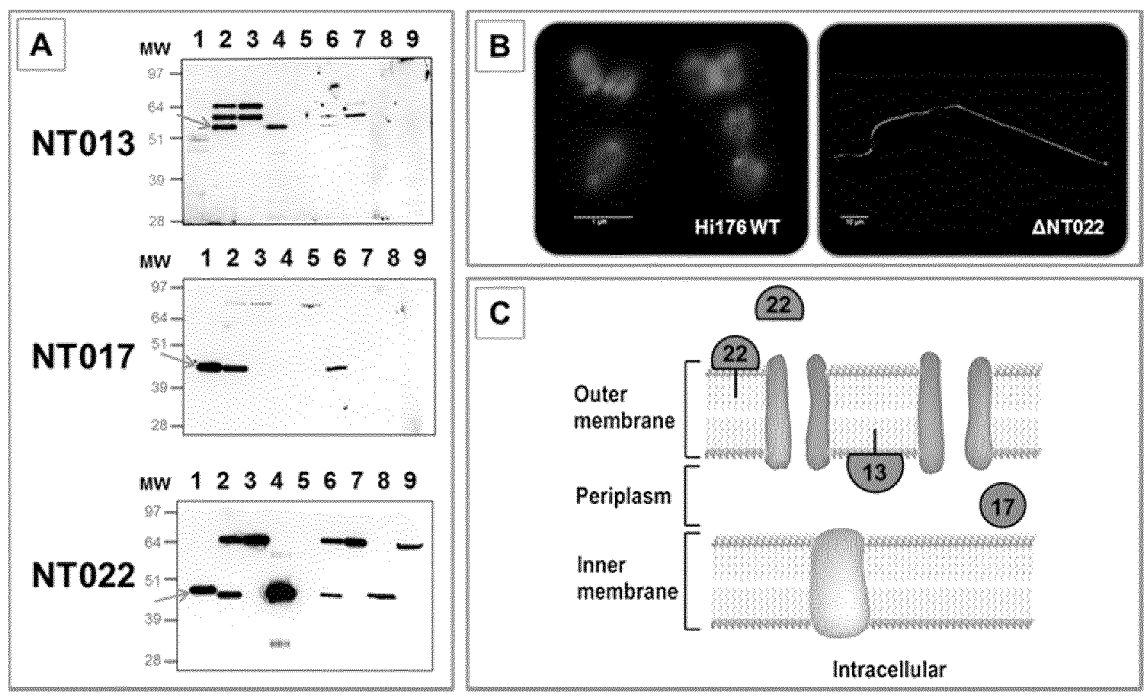
FIG. 1: Expression and subcellular localization of NTHi LytM factors. (A) Western blot analysis on different cell compartments extracts were performed using specific antisera raised against NT013, NT017 and NT022. 1—Recombinant protein, 2—total extract WT, 3 total extract KO, 4—outer membrane proteins WT, 5—outer membrane proteins KO, 6—periplasmic fraction WT, 7—periplasmic fraction KO, 8—supernatant, WT 9—supernatant KO. Red arrows indicate the specific signals. As expected, no specific reactivity is observed with the mutant strains; however the antisera cross-react with other not specific bands present also in the knockout strains which were not characterized. (B) Immunofluorescence microscopy analysis on Hi176 wild type strain and 176ANT022 mutant confirming the surface localization of protein NT022. Bacteria are red and LytM factors in green. (C) Model of LytM proteins localization in NTHi.

Single knock-out non-typeable *Haemophilus influenzae* (NTHi) mutants were generated for three LytM metalloproteases: NTHI0532 (NT013), NTHI10915 (NT017) and NTHI0830 (NT022). These mutants displayed cell surface defects which caused an increase in the release of Outer Membrane Vesicles (OMVs). Furthermore, these proteins were shown to be involved in bacterial cell division and pathogenesis. In particular, NT013 and NT022 are fundamental for peptidoglycan cleavage and cell splitting. NT017 has a strong influence on NTHi colonization and host immunity evasion.

Methods

Bacterial Strains and Growth Conditions

NTHi Strain 176 was used for this study. It was part of a Finnish otitis media cohort study, as isolate obtained from the middle ear. NTHi was cultivated on chocolate agar polivitex (BioMerieux) incubated at 37° C. with 5% $CO_2$. Brain-heart infusion (BHI) broth (Difco Laboratories) supplemented with 10 μg/mL each of haemin (Fluka Biochemika) and nicotinamide adenine dinucleotide (NAD, Sigma) was used as fluid growth medium. *Escherichia coli* strains DH5a, HK100 and BL21 (DE3) (Invitrogen) were used for cloning and expression of LytM proteins. They were cultured at 37° C. in Luria Bertani (LB) medium and, when required, supplemented with 100 μg/mL ampicillin.

Cell Cultures

Tissue culture cells used in this study are Chang epithelial cells (Wong-Kilbourne derivative, clone 1-5c-4, human conjunctiva, ATCC® CCL-20.2™) and HEK293 (human kidney, ATCC® CRL1573™). Chang cells were maintained in Dulbecco's Modified Eagle's Medium (D-MEM; Gibco) supplemented with 25 mM Hepes, 15 mM L-glutamine, antibiotics and 10% (vol/vol) heat-inactivated fetal calf serum (FCS, Invitrogen Corporation). They were grown at 37° C. with 5% $CO_2$.

HEK293 cells stably expressing TLR2 or TLR4/MD2/CD14 and the NF-κB-luciferase reporter cassette, were cultured in DMEM containing 4.5 g/ml glucose, supplemented with 10% heat inactivated FBS, 100 U/ml pelicillin, 100 μg/ml streptomycin, 2 mM glutamine, 5 μg/ml puromycin 250 μg/ml hygromycin (and plus 10 μg/ml Blasticidin for HEK293-TLR4 cells).

Cloning of Genes Coding Fr LyM Proteins

LytM genes were cloned into the pET15b+ vector (Novagen) by the polymerase incomplete primer extension (PIPE) method (119). In brief, sequences coding for each protein were amplified by PCR from the HI176 genomic DNA, removing the signal peptide. PCRs generated mixtures of incomplete extension products, by primer design, short overlapping sequences were introduced at the ends of these incomplete extension mixtures, which allowed complementary strands to anneal and produce hybrid vector-insert combinations. *Escherichia coli* HK100 cells [120] were then transformed with vector-insert hybrids. Single ampicillin-resistant colonies were selected and checked for the presence of the recombinant plasmid by PCR. Plasmids from positive clones were isolated and subcloned into competent *E. coli* BL21(DE3) cells.

Expression and Purification of Recombinant Proteins

For protein purification, one single colony of *E. coli* BL21(DE3) strain expressing NTHI0532, NTHI0915 and NTHI0830 were inoculated in LB+ampicillin and grown overnight at 37° C., diluted in fresh LB medium and grown at 30° C. to an OD of 0.6-0.8. The protein over-expression was induced by the addition of 1 mM isopropyl-1-thio-β-D-galactopyranoside (IPTG; Sigma) for 4 hours. Recombinant 6×His-fusion proteins was purified by affinity chromatography on $Ni^{2+}$-conjugated chelating fast-flow Sepharose 4B resin (Pharmacia). The purity was checked by SDS-PAGE electrophoresis staining with Coomassie blue. Protein concentration was determined using the bicinchoninic acid (BCA) assay (Thermo Scientific).

Construction of the Knockout Mutants

Deleted mutants of NTHI0532, NTHI0915 and NTHI0830 were constructed by allelic replacement of each whole gene with an erythromycin resistance cassette. Upstream and downstream regions of the three genes were amplified by PCR using the primers listed below and cloned in Stratagene pSC-A TOPO vector. Erythromycin resistance cassette was purified from pIM13 plasmid. The constructs containing upstream regions, resistance cassette and downstream regions were assembled. Plasmids obtained were linearized and used to transform 176 NTHi strain using MIV protocol [121]. Knockout strains obtained were confirmed by PCR western blot and locus sequencing.

| NT013 | NT013 5'FOR | TTGCACGCGCCAAAATACC | SEQ ID NO: 25 |
|---|---|---|---|
|  | NT013 5'REV | TGCATGCATTTACGTGTTGCACTGGCATC | SEQ ID NO: 26 |
|  | NT013 3'FOR | TGCATGCATTGTTCGTGTTCGTGAAGCAG | SEQ ID NO: 26 |
|  | NT013 3'REV | AACGCGATTGCGTAATGCAG | SEQ ID NO: 28 |
| NT017 | NT017 5'FOR | TGCTGGTGCAATTTGATCTTC | SEQ ID NO: 29 |
|  | NT017 5'REV | TGCATGCATTGATTAACGCCAAAACGCAAC | SEQ ID NO: 30 |
|  | NT017 3'FOR | TGCATGCATATTAGCCGTAAAGGAACGCC | SEQ ID NO: 31 |
|  | NT017 3'REV | TGGCGATCTAATGAACGCAC | SEQ ID NO: 32 |
| NT022 | NT022 5'FOR | AAACATTGTGCAACAATGGGG | SEQ ID NO: 33 |
|  | NT022 5'REV | TGCATGCATACAAGACTCAAAGGGAGTAAG | SEQ ID NO: 34 |
|  | NT022 3'FOR | TGCATGCATGGATCCAGTACGTTACCTAC | SEQ ID NO: 35 |
|  | NT022 3'REV | GTTTCTTTGTCCGCAGGTTC | SEQ ID NO: 36 |

Preparation of Polyclonal Antisera

Groups of four CD1 mice were immunized to produce polyclonal antisera; 10 μg of purified protein was used for each mouse. The recombinant protein was given intraperitoneally in the presence of aluminum. A second (day 21) and a third (day 35) booster doses were administered. Blood sample was taken on day 49.

The treatments were performed in accordance with internal animal ethical committee and institutional guidelines.

Cell Fractionation and Western Blot Analysis

*Haemophilus* strains were grown in BHI until mid-log phase at 37° C. with 5% $CO_2$.

Whole cell lysates and periplasmic fractions were purified using PeriPreps Periplasting kit from Epicentre. Outer membrane proteins (OMPs) were recovered on the basis of Sarkosyl-insolubility following the rapid procedure as described by Carlone et al. [122].

To prepare culture supernatants, bacteria were harvested at 13000 g for 10 min at 4° C. 1 ml of culture supernatant was filtered through a 0.22 mm filter and precipitated with vol of 50% TCA for 1 h at 4° C.

After centrifugation at 13000 g for 30 min, the achieved pellet was washed once with 70% ethanol and resuspended in IX sample loading buffer.

Proteins of each cell fraction were separated by SDS-PAGE electrophoresis using NuPAGE Gel System, according to the manufacturer's instructions (Invitrogen), and revealed by Coomassie-blue staining or transferred onto nitrocellulose membranes for Western blot analysis.

Western blots were performed according to standard procedures. The different LytM proteins were identified with a polyclonal mouse antiserum raised against recombinant NTHI0532, NTHI0915 and NTHI0830 (diluted 1:1000) and an anti-mouse antiserum conjugated to horseradish peroxidase (DAKO), as secondary antibody. Bands were visualized with Super Signal Chemiluminescent Substrate (Pierce) and with Opti 4CN Substrate Kit (Bio-Rad) following the manufacturer's instructions.

Confocal Microscopy

The presence of LytM proteins on NTHi surface was checked using confocal imaging. Knockout mutants were used as negative controls. Bacteria were grown until exponential phase, and fixed in 4% paraformaldehyde (Sigma). After multiple washings, bacteria were spread on polylisine-coated slides and blocked with PBS+3% bovine serum albumin (BSA) (Sigma) for 30 min at room temperature. Samples were washed and incubated with specific antisera (1:1000) for 15 min at room temperature. LytM antisera were preadsorbed with intact KO bacteria to minimize cross-reactivity. Bacteria were washed several time with PBS and incubated with Alexa Fluor 488 goat anti-mouse IgG (1:400) (Molecular Probes). Labelled samples were mounted with ProLong® Gold antifade reagent with DAPI (Molecular Probes) and analysed with ZeissLSM710 confocal microscope.

Scanning and Transmission Electron Microscopy

Electron microscopy was performed on 176 wt and knockout strains to observe defects in bacterial morphology. Bacteria were grown until exponential phase, washed with PBS and fixed overnight in cacodylate sucrose buffer containing 2.5% glutaraldehyde and 2.5% paraformaldehyde. Samples were then postfixed in 1% OsO4 and 0.15% ruthenium red in cacodylate buffer, blocked with 1% uranyl acetate and dehydrated with serial dilution of acetone.

For SEM, samples were then dried by the critical point method using $CO_2$ in a Balzers Union CPD 020, sputter-coated with gold in a Balzers MED 010 unit, and observed with a JEOL JSM 5200 electron microscope. For TEM, samples were fixed and dehydrated as described above then embedded in Epon-based resin. Thin sections were cut with a Reichert Ultracut ultramicrotome by use of a diamond knife, collected on collodion copper grids, stained with uranyl acetate and lead citrate, and observed with a JEOL 1200 EX II electron microscope.

Preparation of Outer Membrane Vesicles

Native Outer membrane vesicles (OMVs) were isolated from WT and mutant strains, growing the bacteria until exponential phase in 200 ml BHI cultures. Bacteria were then centrifuged and supernatant were filtered and left at 4° C. overnight adding proteases inhibitor and EDTA. Supernatant were ultracentrifuged for 3 hours at maximum 200000×g and final pellet containing OMVs was resuspended in PBS.

Mass Spectrometry

SDS-PAGE Coomassie stained bands were excised and destained in 50 mM $NH_4HCO_3$ 50% acetonitrile. After a drying step, bands were in-gel digested with 12.5 ng/ml Trypsin in 5 mM $NH_4HCO_3$ overnight at 37° C. The reaction was stopped by the addition of 0.1% final concentration Trifluoroacetic acid (TFA) and the samples were subjected to MALDI-TOF Mass Spectrometry analysis. 1 µl of digestion solution was spotted on a PAC target (Prespotted AnchorChip 96, set for Proteomics, Bruker Daltonics) and air-dried at room temperature. Spots were washed with 0.6 µl a solution of 70% (vol/vol) ethanol, 0.1% (vol/vol) TFA. Peptide mass spectra were externally calibrated using the standards pre-spotted on the target. Peptide molecular masses determination was performed using a MALDI-TOF/ TOF mass spectrometer UltraFlex (Bruker Daltonics, Bremen, GmbH). Ions generated by laser desorption at 337 nm (N2 laser) were recorded at an acceleration voltage of 25 kV in the reflector mode. In general, approximately 200 single spectra were accumulated for improving the signal/ noise ration and analyzed by FlexAnalysis (version 2.4, Bruker Daltonics) Peptide mass fingerprints were performed using MASCOT searches against *Haemophilus influenzae* 86-028NP database using the following parameters: (i) 1 as number of allowed missed cleavages, (ii) methionine oxidation as variable modification, (iii) 75 ppm as peptide tolerance. Only significant hits were considered, as defined by the MASCOT scoring and probability system.

Reactogenicity Assays

For luciferase assay HEK293-TLR2 and HEK293-TLR4 cells were seeded into microclear 96-well bottom plates in 90 µl of complete medium in absence of selection antibiotics. After overnight incubation, cells were stimulated in duplicates with different concentration of OMVs (10 µl/well) starting from 1 mg/ml diluted 1:2 in PBS, for 6 h. Then the medium were discarded and cells were lysed with 20 µl of Passive Lysis Buffer (Promega) for 20 min at room temperature. Luciferase levels were measured by addition of 100 µl/well Luciferase Assay Substrate (Promega) using LMax II384 microplate reader (Molecular Devices). Raw light units (RLU) from each sample were divided by the RLU of the control sample (PBS) and expressed as Fold Induction (FI).

PBMCs (Pheripheral Blood Mononuclear Cells) were isolated from buffy coats of healthy donors using Ficoll (Amersham Biosciences) density gradient centrifugation. Cells were seeded into microclear %-well bottom plates in 180 µl of RPMI (GIBCO) supplemented with 10% of heat-inactivated FBS, 100 U/ml pelicillin, 100 µg/ml streptomycin, 2 mM glutamine. Cells were stimulated with different concentration of OMVs (20 µl/well) starting from 1 mg/ml diluted 1:2 in PBS, for overnight. Mesoscale Assay Human-Proinflammatory 7-spot (MSD Technology) is used for detection of inflammatory cytokines following manufacturer's instructions.

Results

NT013, NT017 and NT022 of NTHi show a significant homology with a number of previously characterized LytM-proteins expressed by other Gram-negative bacteria. In particular, *E. coli* proteins known to be involved in the cell division process such as YebA, EnvC and NlpD show an amino acid identity of 49% with NT013, 40% with NT017 and 43% with NT022, respectively. LytM catalytic domains are the most conserved regions between NTHi and *E. coli* proteins, in fact, the homology percentage grows up to 79% for this specific domain.

LytM Proteins are Differently Distributed on NTHi Compartments

In order to verify expression and the subcellular localization of LytM proteins NT013, NT017 and NT022, single deletion mutants of the genes codifying for the three LytM proteins were generated in NTHi176 strain. Immunoblotting with specific antisera raised against each of the LytM recombinant proteins was performed to determine the level of expression in periplasmic, outer membrane and supernatant fractions.

As shown in FIG. 1A, NT013 was detected in the outer membrane protein extracts, NT017 in the periplasmic fraction, while NT022 was found in all fractions. As a control, none of the antisera recognized specific bands at 53 kDa, 46 kDa and 42.5 kDa corresponding to NT013. NT017 and NT022 in cell preparations from the respective knockout mutant strains (FIG. 1A).

Surprisingly, confocal immunofluorescence microscopy of bacteria stained for NT013 revealed no specific signal of the protein on the bacterial surface, indicating that NT013 could be associated to the inner layer of the outer membrane as it was found to be present in the outer membrane fraction by western blot analysis. As expected, NT017, which was found in the periplasmatic fraction, was negative by confocal microscopy analysis and NT022 was confirmed to be exposed on the bacterial surface (FIG. 1B). Of interest, it appears that the antigen is translocated on the bacterial surface at specific foci close to the division septum (FIG. 1B). A model of the protein localisation is illustrated in FIG. 1C.

Figure 2:
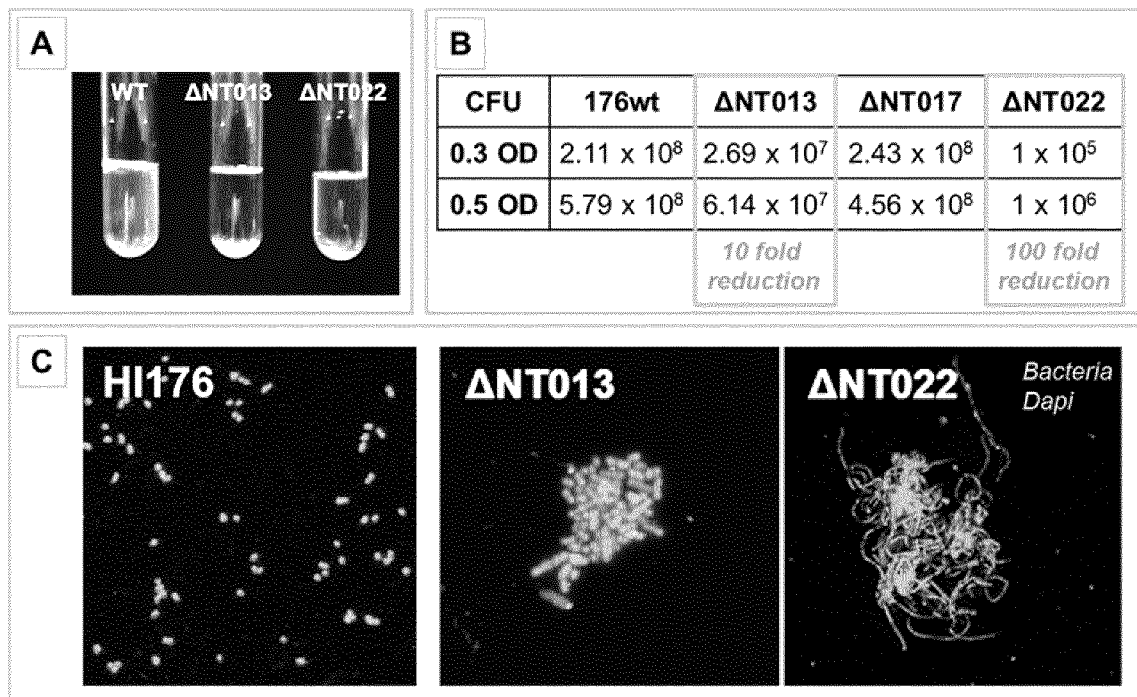
FIG. 2: Phenotypic characterization of NTHi Hi176 wild type and LytM mutants. Aggregation phenotype in liquid static cultures growth for 16 h at 37° C. (A) and CFU per milliliter (B) CFU counts was performed at two different OD. The 176ANT017 strain has a growth rate and a CFU similar to the parent strain, while the 176ANT013 and 176ANT022 mutants showed a reduced growth rate growth and a lower CFU. (C) Confocal imaging showing bacterial aggregation of 176ANT013 and 176ANT022 strains, bacteria are stained in red and Dapi in blue.

176ΔNT013 and 176ΔNT022 Exhibit Aberrant Cell Morphology and Severe Cell Separation Defects To investigate whether NTHi LytM proteins, NT013 and NT022, played a role in cell separation, single isogenic knockout mutants (176ΔNT013 and 176ΔNT022) were cultured on solid or liquid medium and compared to the wild type strain. These showed no differences in colony morphology as visualized by light microscopy. To evaluate the effect of the mutations, knockout strains were grown in liquid BHI at 37° C. There were no significant differences in the growth rate of WT and mutants, but a phenotype of aggregation was observed in liquid cultures for 176ΔNT013 and 176ΔNT022 (FIG. 2A), and was confirmed by confocal imaging (FIG. 2C). The number of bacterial colonies was also measured at two different OD by plating cultures serial dilution on agar chocolate plates. Colony forming units (CFU) per millilitre of 176ΔNT013 and 176ΔNT022 was much lower than the wild type Hi176 and of 176ΔNT017, indeed CFU derived from 176ΔNT013 and 176ΔNT022 are respectively only about 10% and 1% with respect to the parent strain (FIG. 2B).

Figure 3:
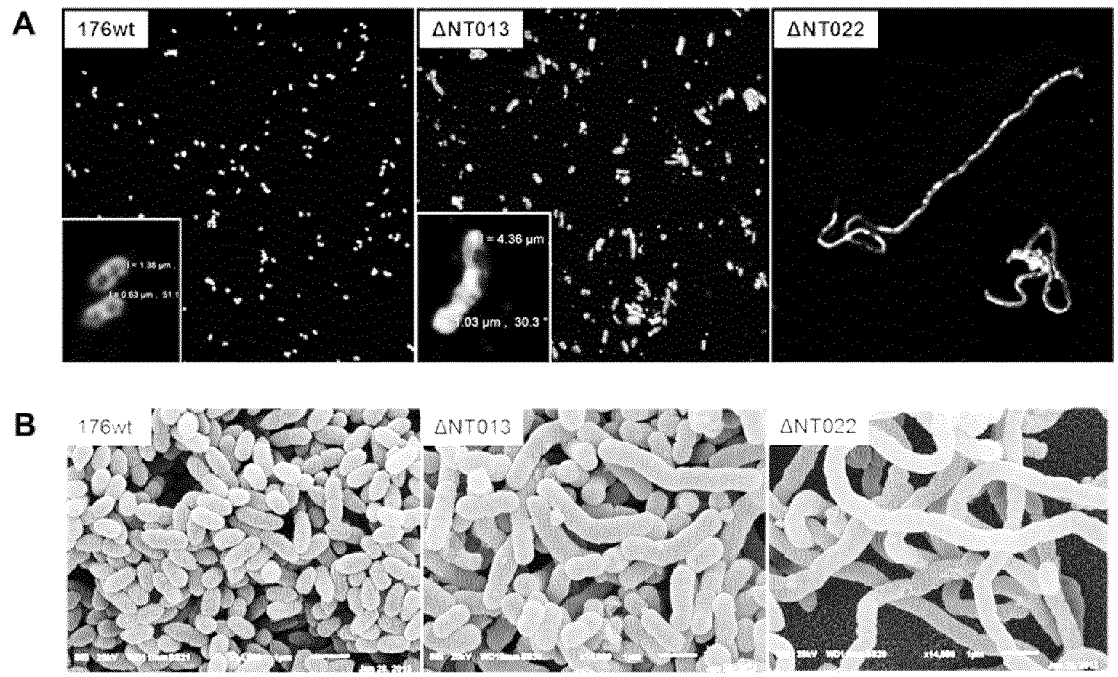
FIG. 3: Confocal and electron microscopy on LytM mutants. (A) Confocal imaging of Hil76 wt, 176ΔNT013 and 176ΔNT022, bacteria are stained in red (anti total bacterium) and blue (DAPI). (B) Scanning electron microscopy of 176 wt, 176ΔNT013 and 176ΔNT022. The mutant 176ΔNT017 does not show any difference compared to the wild type strain (data not shown).

To verify whether the bacterial aggregation phenotype was due to a failure in cell separation, we used confocal and scanning electron microscopy which clearly showed that 176ΔNT013 and 176ΔNT022 mutants differ from the wild type in dimension and morphology (FIGS. 3A and 3B).

In particular, 176ΔNT013 cells appeared roughly four times longer than the wild type strain and are bended in the central portion. On the other hand, 176ΔNT022 mutant forms longer chains (up to 0.1 mm), while no evident morphological differences were observed for 176ΔNT017. The same phenotype was observed when LytM mutants were generated in a different strain (Hi162), indicating the ubiquitous functional properties of such determinants.

This result indicates that NT013 and NT022 are involved in bacterial separation, although they are not essential for NTHi cell growth.

176ΔNT013 and 176ΔNT022 mutants release outer membrane vesicles

Figure 4:
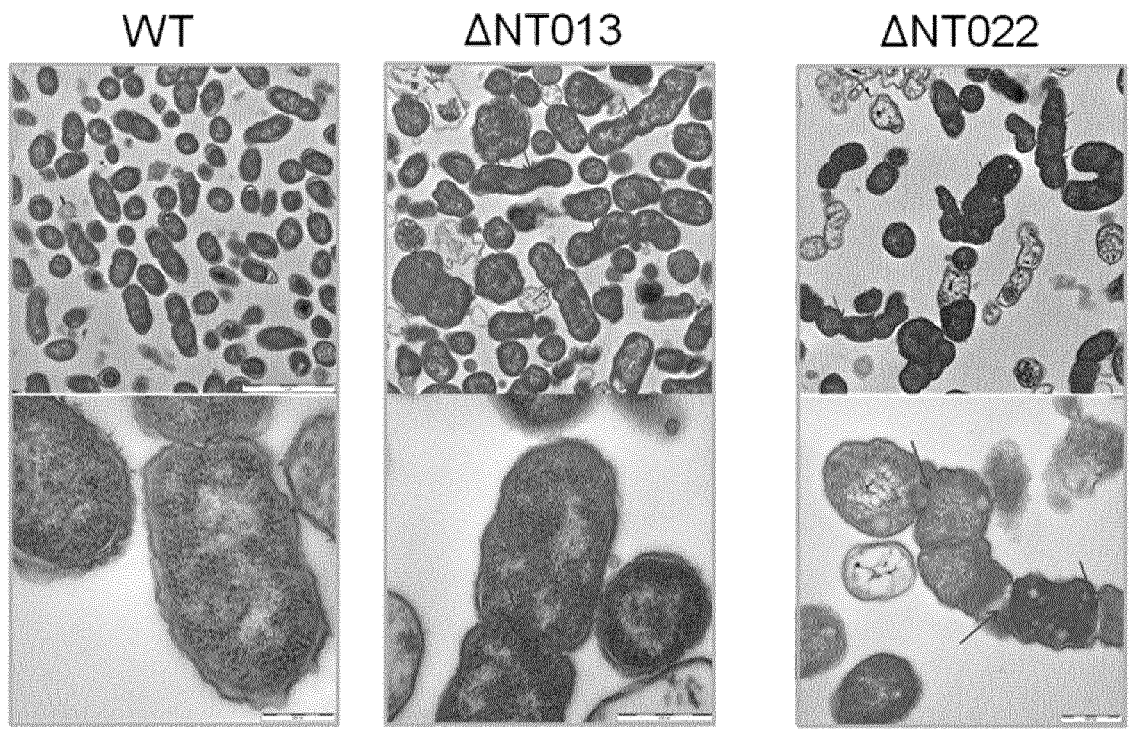
FIG. 4: Septum formation in LytM mutants. Transmission electron microscopy on Hi176 wt and LytM mutants. Red arrows indicate impaired septum formation in mutants 176ΔN7013 and 176ΔN7022.
Figure 5:
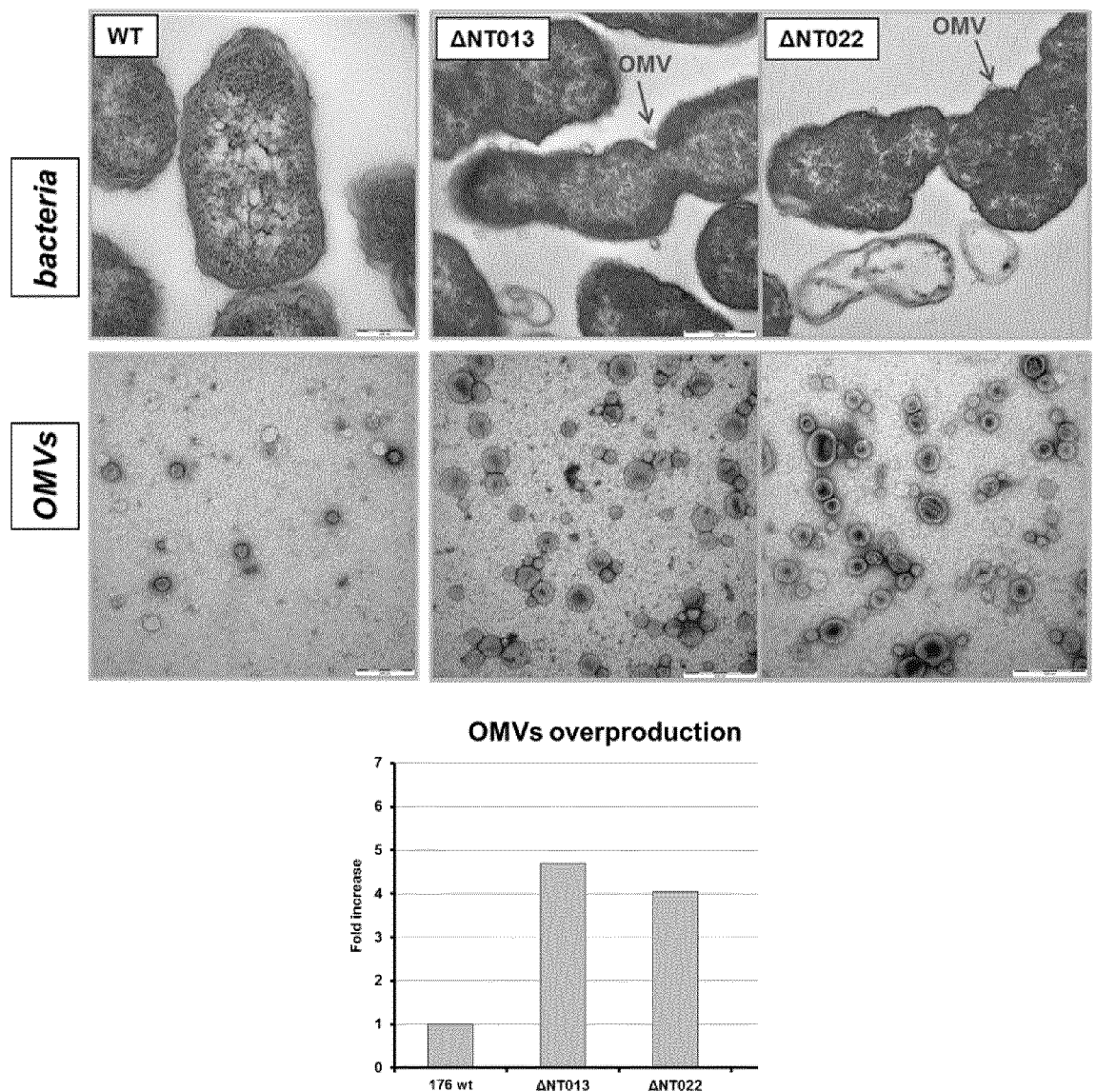
FIG. 5: The mutants 176ΔNT013 and 176ΔNT022 release more OMVs than the wild type strain. Transmission electron microscopy of Hi176WT, 176ΔNT013 and 176ΔNT022 mutants and of their respective OMVs preparations. Red arrows indicate OMVs that are released from bacterial surface.

Defective septum formation in 176ΔNT013 and 176ΔNT022 mutants was observed in transmission electron microscopy (TEM) of bacterial cell surfaces (FIG. 4). Moreover, an exclusive formation of blebs on the surface of both these mutants was highlighted (FIG. 5).

This membrane blebbing is believed to be due to an overproduction of Outer Membrane Vesicles (OMVs) which are naturally secreted by Gram negative bacteria. Native OMVs were purified from these two mutants and from the Hi176 strain to verify the quality and to quantify OMV release. Isolation of OMVs revealed that both mutant strains produce more vesicles with respect to the wild type strain (FIG. 5). TEM analysis of OMV preparations confirmed the presence of vesicles with an apparent diameter of 20 to 100 nm (FIG. 5). OMV overproduction in LytM mutants was

|  | 176 WT | ΔTolR | ΔNT013 | ΔNT022 |
|---|---|---|---|---|
| Total proteins (ng) | 101.546 | 100.127 | 101.567 | 102.663 |
| P2 | 40.2 | 17.29 | 13.0889 | 11.129 |
| P5 | 16.69 | 25.488 | 18.41 | 12.169 |
| Total proteins − (P2 + P5) | 44.62 | 57.34 | 70.06 | 79.36 |
| % P2-P5 | 56.06 | 42.73 | 31.02 | 22.7 |
| % rest of OMP | 43.94 | 57.27 | 68.98 | 77.3 |

A summary of the proteomic data relating to virulence factors in the NT017 mutant is set out below:

| Decrease >50% | | Similar | | | Increase <50% | |
|---|---|---|---|---|---|---|
| | wt | ko | | wt | ko | | wt | ko |
| HtrA | 8.281 | 1.559 | D15 | 1.429 | 1.529 | Protein 5 | 16.693 | 23.523 |
| Omp26 | 3.441 | 2.202 | Protein 6 | 0.720 | 0.864 | Iga1 protease | 0 | 9.538 |
| NT067 | 1.870 | 0.628 | phosphate binding periplasmic protein | 0.760 | 0.880 | long chain fatty acid ABC transporter | 0.648 | 1.670 |
| Protein E | 0.234 | 0 | | | | | | |
| HMW2B | 1.187 | 0.853 | PstS | | | | | |
| | | | NT018 | 0.701 | 0.575 | HxuA | 0 | 0.697 |
| | | | NT022 | 0.336 | 0.421 | opacity protein | 0.469 | 1.106 |
| | | | SurA | 0.490 | 0.370 | | | | quantified and showed a fourfold increase with respect to WT (Lowry Method for protein quantitation).

Protein Composition of Outer Membrane Vesicles

To compare the protein composition of the OMVs extracted from each strain, samples were run on a SDS-page gel and a Coomassie blue staining was performed (FIG. 6A). Protein patterns were similar between wild type and mutant strains, although a few bands showed a different intensity. As expected, mass spectrometry analysis associated these bands to a number of known surface determinants, including HMW1 and 2, HtrA, P2, P5 and OMP26 (FIG. 6B). Comparisons were made with the known TolR mutant as well as wild type.

OMVs purified from the mutants strains were analysed for their protein content and compared to OMVs purified from the wild type strain on the basis of mass spectroscopy of selected bands.

Figure 7:
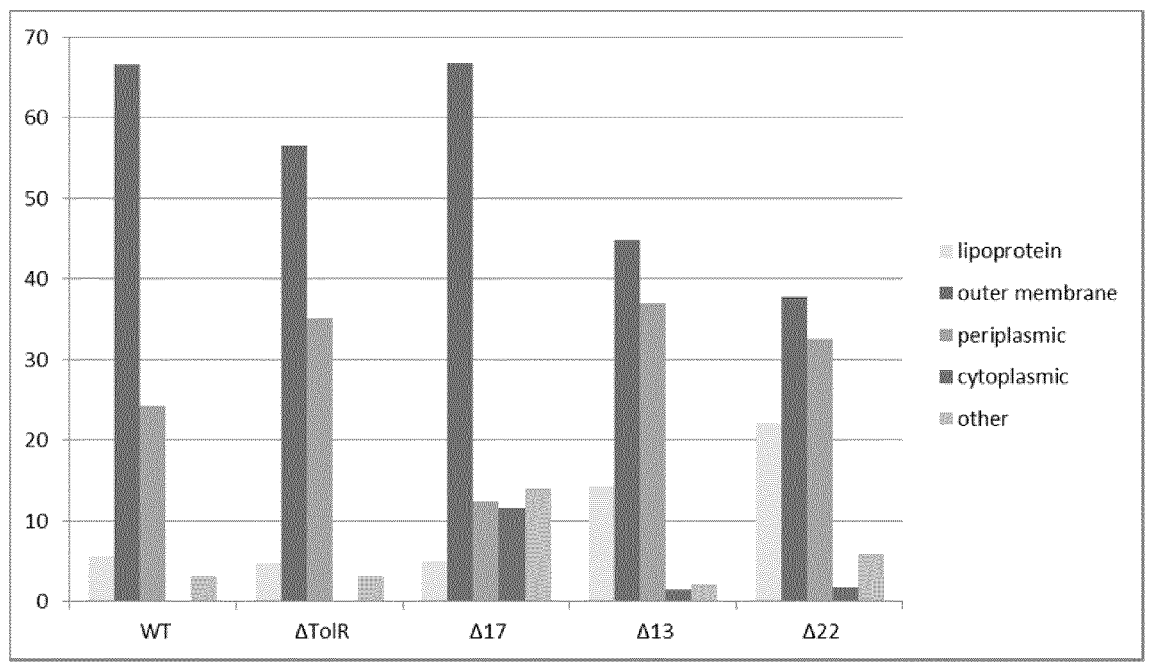
FIG. 7: Analysis of proteins found in OMVs
Figure 8:
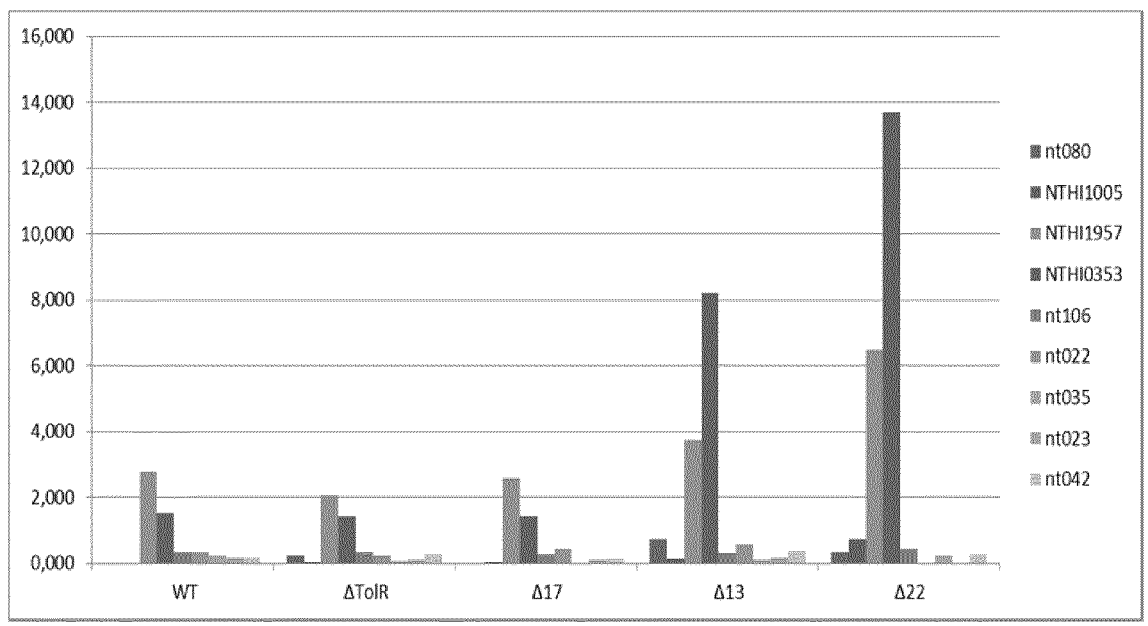
FIG. 8: Lipoproteins in OMVs. OMVs from WT, ΔtolR, Δ17 have similar amounts of lipoproteins, while Δ13 and Δ22 mutants are enriched for lipoproteins, in particular NTHI1957 and NTHI 0353 lipoproteins.
Figure 9:
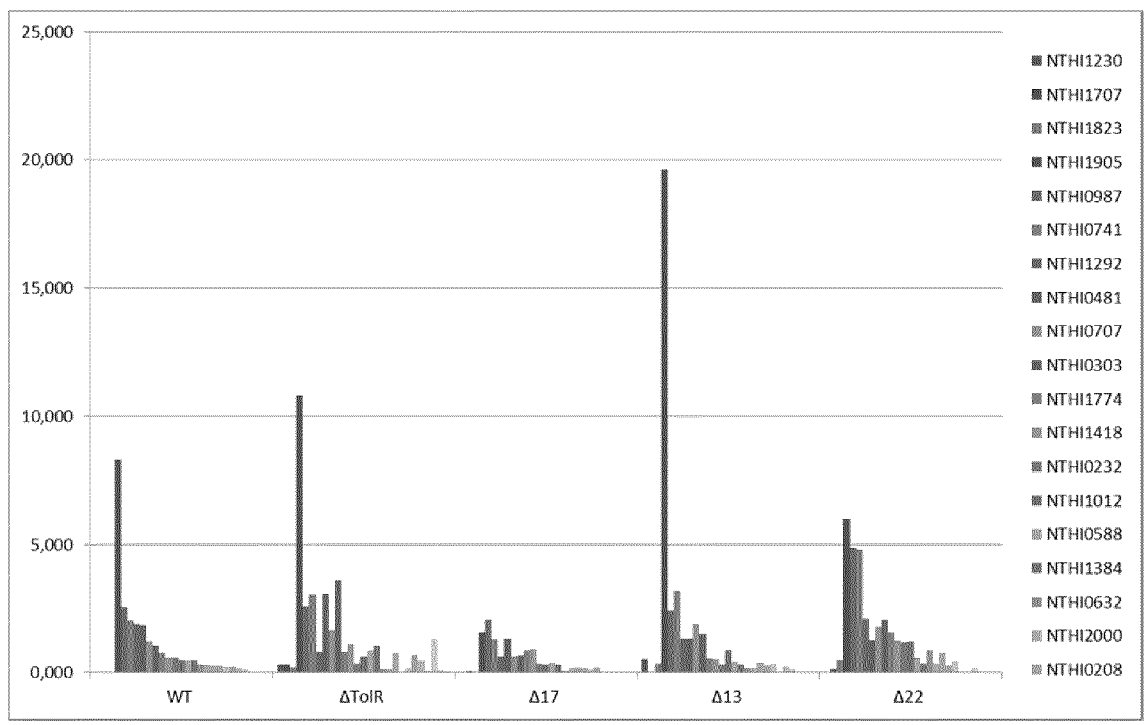
FIG. 9: Periplasmic proteins in OMVs. The major periplasmic protein is the periplasmic serine protease do HhoA. This is particularly true from the vesicle derived from Δ13. Compared to OMVs generated from the WT, OMVs derived from ΔtolR and Δ22 are enriched in periplasmic proteins. Compared to OMVs generated from the WT, OMVs derived from Δ17 contain low amount of periplasmic proteins.
Figure 10:
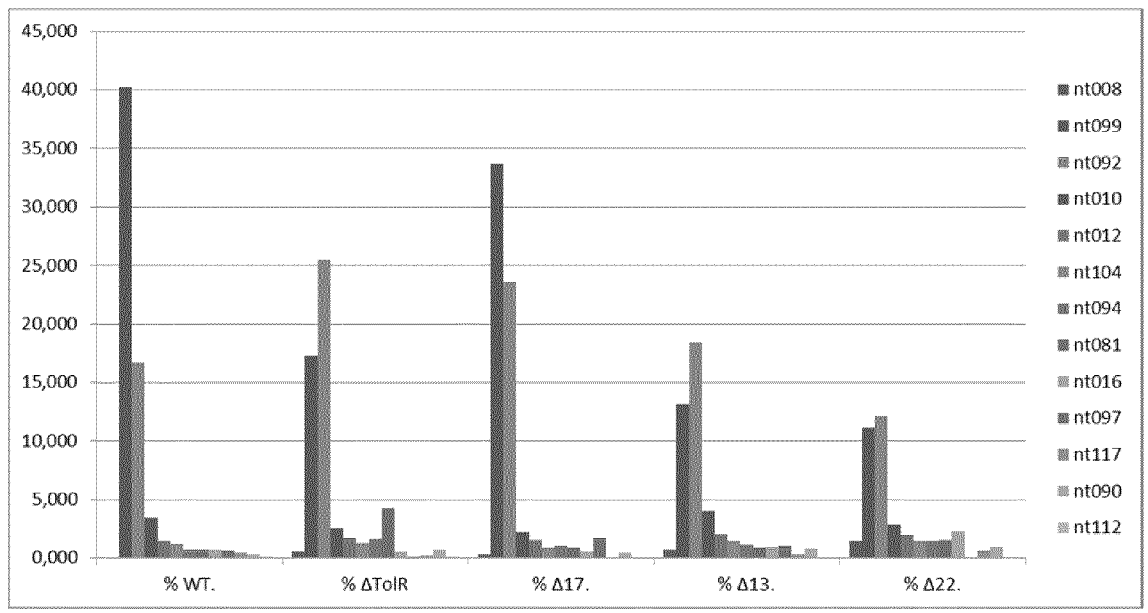
FIG. 10: Outer membrane proteins in OMVs. From each type of OMVs, the most abundant outer membrane proteins are the nt099 (outer membrane protein P2) and nt092 (outer membrane protein P5). The main drop in outer membrane protein amount observed for OMVs derived from Δ13 and Δ22 is due to the reduction of P2.
Figure 11:
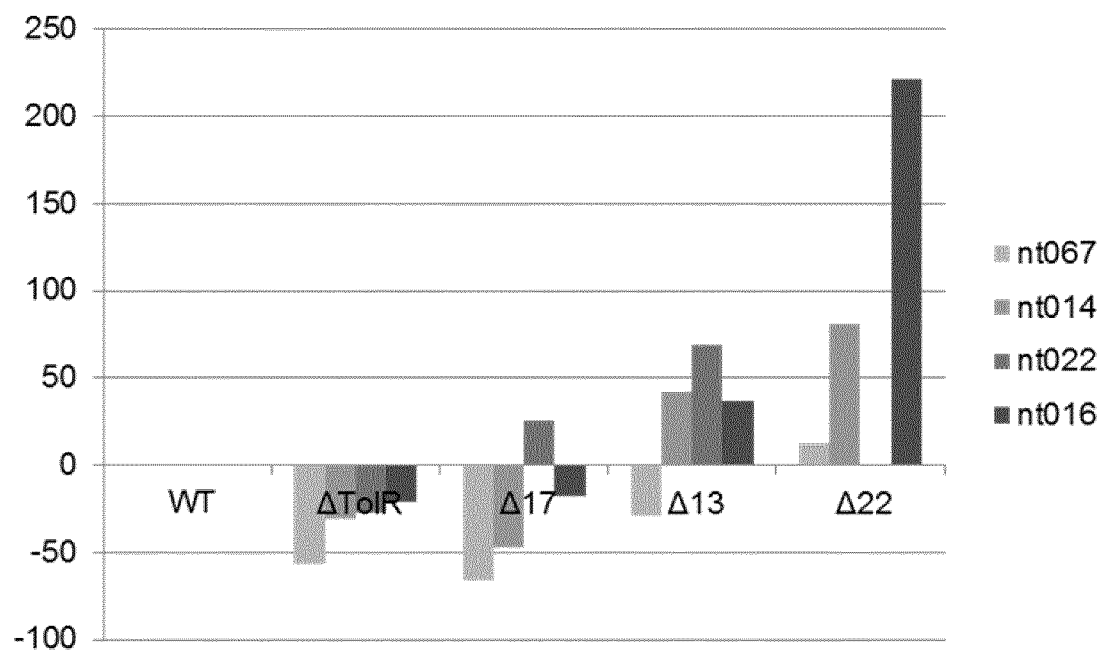
FIG. 11: Relative amounts of proteins in OMVs. Relative amounts of proteins nt067, nt014, nt022 and nt016 found in OMVs produced by mutant strains, relative to the wild type strain.

Haemophilus proteins were grouped into five classes according to their localisation within the cell, and the amount of protein from each class present in OMVs was measured. Differences were observed between wild type and mutants and this is suggestive of distinct mechanisms of OMV formation (see FIG. 7). NT013 and NT022 mutant OMVs displayed increased amounts of lipoproteins and reduced amounts of outer membrane proteins. The amounts of individual proteins were quantified within each class. The results for the lipoprotein, periplasmic protein and outer membrane protein classes are illustrated in FIG. 8, FIG. 9 and FIG. 10 respectively.

One difference is a decrease in the quantity of the outer membrane immunodominant proteins (protein 2 and protein 5) in mutant strains (see FIG. 10 and Table below). In particular in wild type the quantity of these P2 and P5 is about 56% of total, in ΔNT013 it decreases to 31% and in ΔNT022 to 23%. P2 and P5 are very abundant and variable proteins and their presence is one of the key reasons for the lack of cross reactivity in the sera generated against haemophilus OMVs. The mutant OMVs with reduced P2 and P5 concentration may therefore be used to improve cross reactivity.

Immunological studies were performed on OMVs from wild types and mutants to determine if the differences observed in OMVs protein patterns could influence TLRs activation by LPS or lipoprotein components. HEK293-hTLR2 and HEK293-hTLR4/CD14-MD2 cells were stimulated with different dilutions of OMVs from the wild type and knockout strains. No significant differences were detected (FIG. 6C-6D).

Moreover the same stimulation was extended to human Peripheral Blood Mononuclear Cells (hPBMCs) to measure proinflammatory cytokines production. No significant differences were observed (FIG. 6E-6F).

LytM Protein Knock Out in Neissena meningitidis

Three LytM proteins were identified in Neisseria meningitidis MC58 and are: NMB1483, NMB0315 and NMB1333. NMB1483 contains two LysM domains and a M23 peptidase family domain, and is the NlpD homologue found in Neisseria meningitidis group B. NMB0315 is also a lysostaphin-type zinc-dependent metallopeptidase belonging to the M23 peptidase family and is characterized by a conserved active site containing an HXH motif. NMB1333 also presents a conserved domain typical of the M23 peptidase family. The gene and protein sequences for the LytM proteins were identified in Neisseria meningitidis are set out in SEQ ID NOs: 37-42.

| NMB1483 nucleic acid | SEQ ID NO: 37 |
| NMB0315 nucleic acid | SEQ ID NO: 38 |
| NMB1333 nucleic acid | SEQ ID NO: 39 |
| NMB1483 protein | SEQ ID NO: 40 |
| NMB0315 protein | SEQ ID NO: 41 |
| NMB1333 protein | SEQ ID NO: 42 |

A knockout mutant was generated in strain MC58 of Neisseria meningitidis for gene NMB1483 (NlpD) and it was named: MC58Δ148. A detailed description of the generation of knock out mutants is described elsewhere [123].

Flanking regions to the coding sequence of the gene were amplified using the following sets of primers:

```
Up1483_Fw lgctctagaCGTTACAGCGGCAATTATTGC XbaI   SEQ ID
                                                NO: 43

Up1483_Rv tcccccgggCGCAGACAGTACAGATAGTACSmaI    SEQ ID
                                                NO: 44

Dn1483_Fw tcccccgggATGTTCCGATATATAGCCTG SmaI    SEQ ID
                                                NO: 45

Dn1483_Rv2ccgctcgaCCCCTATTTTGTGGAACATC  XhoI    SEQ ID
                                                NO: 46
```

The plasmid used for generation of the deletion mutant in MC58 was: pBS-UD1483_Ery. By chromosomal allelic exchange, the gene was substituted by an erythromycin resistance cassette.

Figure 12:
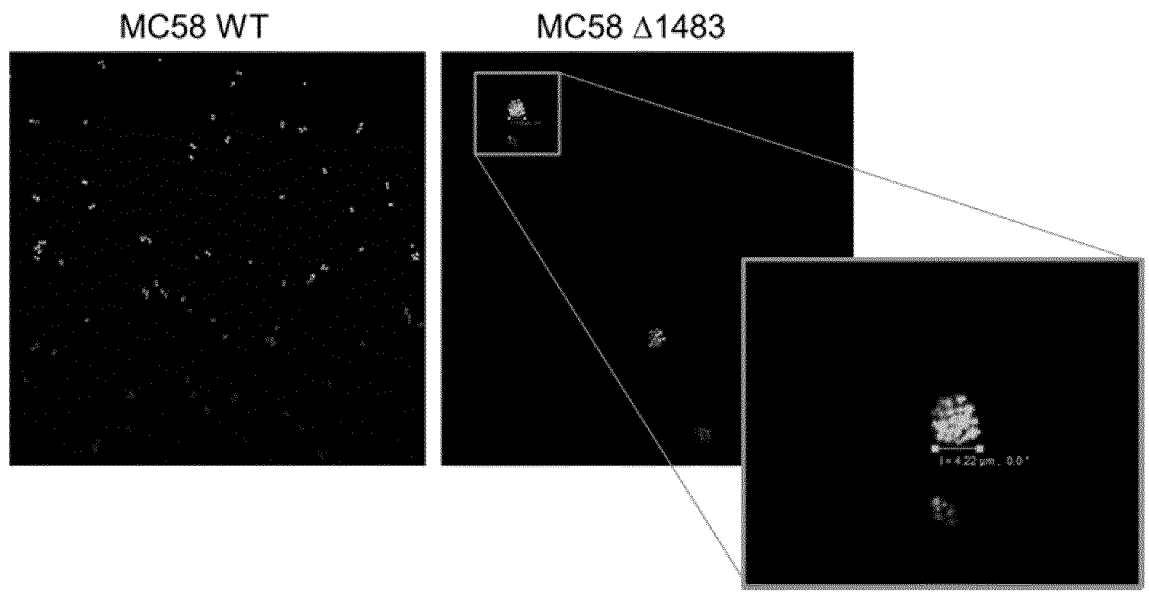
FIG. 12: DAPI staining of MC58 Δ1483 and wild type bacteria.

The MC58Δ1483 strain was analysed by confocal microscopy analysis and showed the presence of multiple aggregates of variable size, with respect to the WT strain. For confocal microscopy analysis bacteria were grown in GC medium until exponential phase ($OD_{600}$ 0.5) and fixed in 4% paraformaldehyde, before DAPI staining (See FIG. 12).

Figure 13:
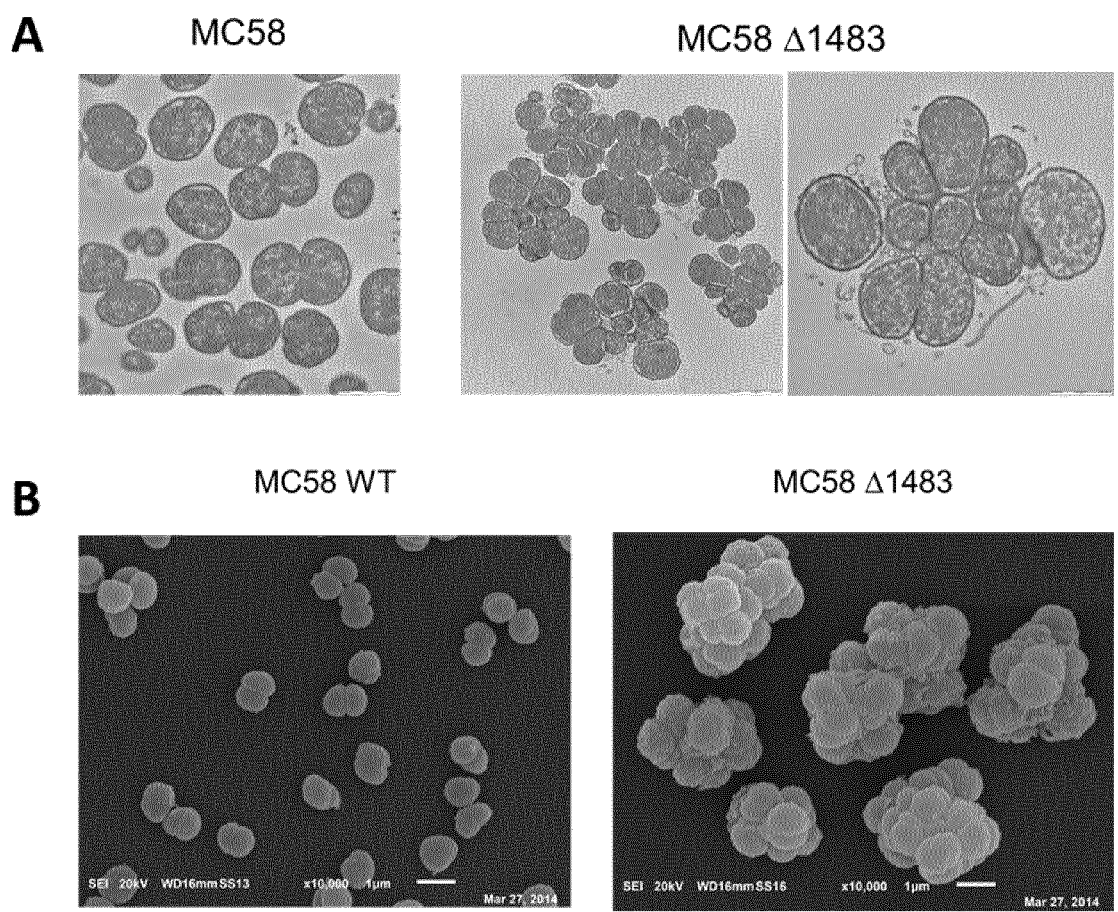
FIG. 13: TEM (A) and SEM (B) analysis of MC58 Δ1483 and wild type bacteria.

To further characterize the bacterial cell morphology TEM (transmission electron microscopy) and SEM (scanning electron microscopy) analysis was performed. For TEM analysis, bacteria were also grown in GC medium until exponential phase ($OD_{600}$ 0.5). TEM analysis confirmed the presence of bacterial aggregates and aberrant cell morphology was shown in MC58Δ1483, compared to the diplococcic observed in the WT strain. Moreover, the presence of vesicles was clearly visible in the mutant strain (See FIG. 13A).

For SEM analysis, bacteria were also grown in GC medium until exponential phase ($ODM_{600}$ 0.5). Also SEM analysis confirmed the presence of three-dimensional bacterial aggregates and of aberrant cell morphology in the MC58Δ1483 mutant (See FIG. 13B).

The MC58Δ1483 mutant was also tested for its ability to produce OMVs. In a first experiment, strains MC58 and MC58Δ483 were grown till stationary phase (OD 1.3-1.5) in 50 ml MCDM I (Meningitis chemically defined medium 1), in 250 ml shaker flasks incubated overnight at 37° C., 5% $CO_2$ and 185 rpm.

For OMVs isolation, the cultures were centrifuged at 3500 rpm for 30 min at 4° C. and supernatants were filtered using Stericup filter bottles (0.22 μm pore size).

Samples were then centrifuged at 35,000 rpm (96,000×g, average) at 4° C. for 2 h, then washed with PBS and centrifuged again at 35,000 rpm (96,000×g, average) at 4° C. for 2 h. After removal of supernatant, the pellet was resuspended in 200 to 500 μl PBS.

For checking the quality of the preparation and compare the amount of vesicles produced by the MC58 WT and MC58Δ1483 mutant strains, the same volume of OMVs was loaded for SDS-PAGE analysis and proteins were stained with Coomassie blue. The results showed a different protein pattern in the MC58Δ1483 mutant, compared to the WT strain. Total protein quantification by Lowry assay showed a two-fold increase in the production of OMVs from the mutant, compared to the WT strain (FIG. 14A) In a second experiment, strains MC58 and MC58Δ1483 were grown till exponential phase ($OD_{600}$ 0.5) in 40 ml GC medium, in 250 ml shaker flasks incubated at 37° C., 5% CO2 and 185 rpm. For OMVs isolation, the same protocol was followed.

Figure 14:
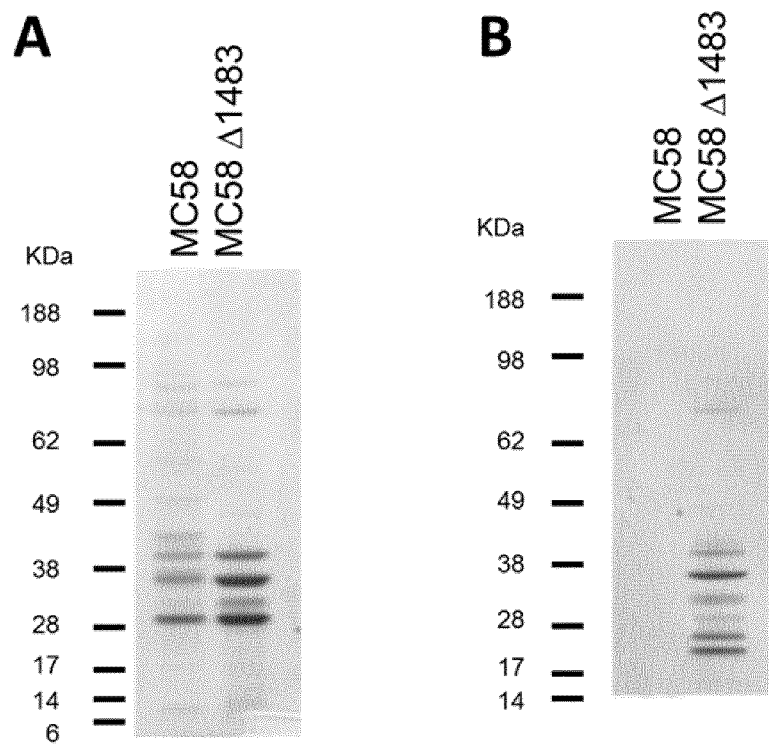
FIG. 14: Protein analysis of vesicles produced by MC58 Δ1483 and wild type bacteria.
Figure 15:
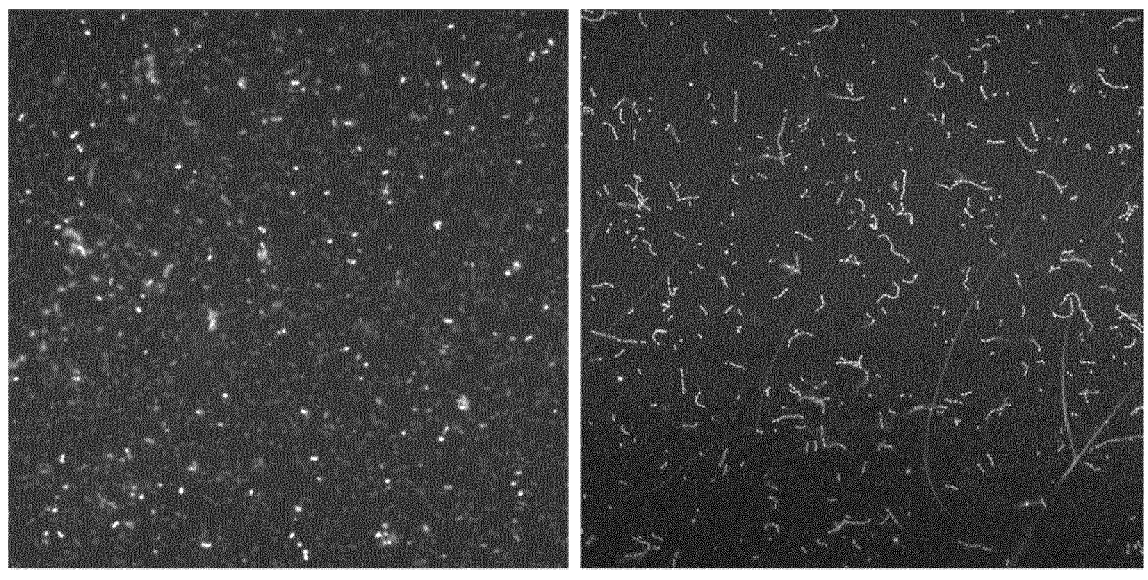
FIG. 15: DAPI staining of BP1721 knockout and wild type bacteria.
Figure 19:
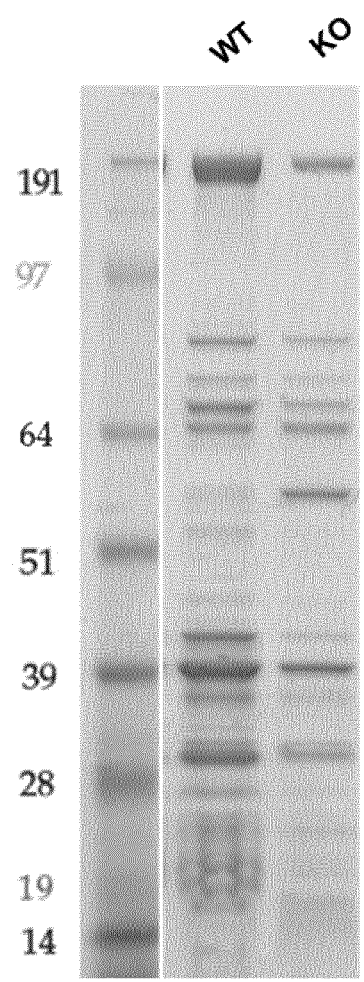
FIG. 19: Protein analysis of vesicles produced by Bp W28 9G/129K ΔNlpD and wild type bacteria.

The results from SDS-PAGE analysis showed OMV proteins only from the MC58Δ1483 mutant. No proteins were detected when the same volume of OMVs from the WT strain was loaded. Also quantification by Lowry assay confirmed the absence of OMVs in the preparation from the WT strain (FIG. 14B).

Other OMV preparations are made and a mass-spectrometry proteomic analysis of the sample is performed at exponential and stationary growth phases. The presence of the main 4CMenB vaccine antigens is evaluated and compared.

LytM Protein Knock Out in Bordetella pertussis

Six putative peptidases were identified in *Bordetella pertussis* Tohama I: BP1721, BP2956, BP0608, BP2919, BP3015 and BP1017. BP1721 and BP2919 have both a Lys-M domain (involved in binding to peptidoglygan) and a Lyt-M domain (Lysostaphin-type metallopeptidases) like NlpD from *E. coli* and NT022 from NTHi, the other four proteins have only the Lyt-M domain. The locus organization does not help to discriminate the different homologues, with the exception of BP1721 which can be clearly identified as the NlpD homologue in *B.pertussis*. Multiple alignments showed a high conservation of the peptidase catalytic site between BP2956 and NT013, and between BP0608 and NT017. Gene and protein sequences are shown in SEQ ID NO:s 47-58. BP1721 is a NlpD homologue. BP2956 is a putative NT013/YebA homologue. BP0608 is a putative NT017/EnvC homologue.

|        | Nucleic acid sequence | Protein sequence |
|--------|----------------------|------------------|
| BP1721 | SEQ ID NO: 47        | SEQ ID NO: 53    |
| BP2956 | SEQ ID NO: 48        | SEQ ID NO: 54    |
| BP0608 | SEQ ID NO: 49        | SEQ ID NO: 55    |
| BP2919 | SEQ ID NO: 50        | SEQ ID NO: 56    |
| BP3015 | SEQ ID NO: 51        | SEQ ID NO: 57    |
| BP1017 | SEQ ID NO: 52        | SEQ ID NO: 58    |

A knockout mutant was generated in strain W28 9K-129G of *Bordetella pertussis* for gene BP1721 (NlpD homologue). Flanking regions to the coding sequence of the gene were amplified using the following sets of primers:

```
BP1721     ccgGAATTCGCGGTTGCGCGCGCAGGGCAT      SEQ ID
5'For                                          NO: 59

BP1721     ggaGGATCCACGATTCTCCTGTTTGCTCAA      SEQ ID
5'Rev                                          NO: 60

BP1721     ggaGGATCCCGCCCACGCTCGTTTTCGACC      SEQ ID
3'For                                          NO: 61

BP1721     cccAAGCTTCCACGTCGGTCTCGCAGTACG      SEQ ID
3'Rev                                          NO: 62
```

Deletion of the gene BP1721 was obtained as follows:

A kanamycin resistance cassette was cloned between the BP1721 flanking regions into the suicide vector pSORTP1. The pSORTP1-BP1721KO construct was introduced into *B. pertussis* by conjugation. Integration of the plasmid into the chromosome following the first crossing-over event was selected for gentamicin resistance (present on the plasmid backbone) and kanamycin resistance (present in the plasmid insert). Loss of the plasmid following the second crossing-over event and replacement of the BP1721 gene with the kanamycin cassette was selected for streptomycin resistance (the plasmid confers sensitivity to streptomycin) and kanamycin resistance. The replacement of the BP1721 gene with the kanamycin cassette was confirmed by PCR amplification using primers external to the flanking regions of BP1721 and using *B. pertussis* W29 9K/129G as a control. The expected sizes of the amplification products were 2189 bp for the WT strain and 2574 bp for the KO strain. The primers used were: BP1721 EXT 5' FOR: AACCTGGGCTTGAACTCC (SEQ ID NO:63); BP1721 EXT 3' REV: ACACCAGCCAGGTATTGA (SEQ ID NO:64).

Cell aggregates, which could be due to altered cell division mechanisms, were already visible from the culture when the bacterium was grown in liquid medium. Cell division defects were then subsequently confirmed by confocal microscopy analysis. For the microscopy analysis 50 μl of a liquid culture were fixed with 4% paraformaldehyde and stained with DAPI to visualize DNA. The KO strain clearly exhibited a severe cell chaining phenotype, compared to the WT strain. (See FIG. 15).

Strains Bp W28 9G/129K and Bp W28 9G/129K ΔNlpD were grown until exponential phase ($OD_{600}$ 4.3-4.8) in 40 ml of Stainer-Scholte broth (supplemented with 400 μg/ml streptomycin) in 250 ml shaker flasks and incubated at 35° C. and 180 rpm.

For OMV isolation, the cultures were centrifuged at 5000×g for 45 min at 4° C. and supernatants were filtered using Stericup filter bottles (0.22 μm pore size). Samples were then centrifuged at 96000×g at 4° C. for 2 h, then washed with PBS and centrifuged again at 96000×g at 4° C. for 2 h. After removal of supernatant, the pellet was resuspended in 200 μl PBS.

To check the quality of the preparation and compare the amount of vesicles produced by the Bp W28 9G/129K and Bp W28 9G/129K ΔNlpD strains, the same volume of OMVs (10 μl) was loaded for SDS-PAGE analysis and proteins were stained with Simply Blue™ SafeStain (Life Technologies). The results showed a different protein pattern in the mutant, compared to the WT strain (see FIG. 19).

A knockout mutant is generated in strain W28 9K-129G of *Bordetella pertussis* for gene BP2956 (putative NT013/YebA homologue). Flanking regions to the coding sequence of the gene (bold) are amplified using the following sets of primers:

| | | |
|---|---|---|
| BP2956 5' For | ccgGAATTCATCAAGAAGCTGGGACGT | SEQ ID NO: 65 |
| BP2956 5' Rev | ggaGGATCCAACTTTGCGTTTGAAGCT | SEQ ID NO: 66 |
| BP2956 3' For | ggaGGATCCCAAGCAGCAGATCAAGCT | SEQ ID NO: 67 |
| BP2956 3' Rev | cccAAGCTTGTCGGCGTCGTAAGGCTG | SEQ ID NO: 68 |

Deletion of the gene BP2956 is obtained as follows. A cloramphenicol resistance cassette is cloned between the BP2956 flanking regions into the suicide vector pSORTP1. The pSORTP1-$BP2956_{KO}$ construct is introduced into *B. pertussis* by conjugation. Integration of the plasmid into the chromosome following the first crossing-over event is selected for gentamicin resistance (present on the plasmid backbone) and cloramphenicol resistance (present in the plasmid insert). Loss of the plasmid following the second crossing-over event and replacement of the BP2956 gene with the kanamycin cassette is selected for streptomycin resistance (the plasmid confers sensitivity to streptomycin) and cloramphenicol resistance.

These deletion mutant strains are analyzed for their cell morphology, OMVs production and proteomic characterization. In particular, the presence of *B. pertussis* most immunogenic antigens (PT. FHA and 69K) is evaluated. Finally, these mutants are analyzed in vitro for their function in *B. pertussis* physiology and/or pathogenesis and the OMVs produced are tested in immunogenicity and cross-reactivity studies.

Knock-out mutants for the other putative LytM protein homologues: flanking regions to the coding sequence of the gene (bold) are amplified using the following sets of primers:

| | | |
|---|---|---|
| BP0608 5' For | ccgGAATTCTGGAAAACCGTTTCACGG | SEQ ID NO: 69 |
| BP0608 5' Rev | ggaGGATCCGAATCAGTCCTTTTTCGC | SEQ ID NO: 70 |
| BP0608 3' For | ggaGGATCCATAAATATCGGGAAGTGT | SEQ ID NO: 71 |
| BP0608 3' Rev | cccAAGCTTCCGAGTTCCTTCAGATGG | SEQ ID NO: 72 |
| BP2919 5' For | ccgGAATTCCATGATGCCGACTTGCAT | SEQ ID NO: 73 |
| BP2919 5' Rev | ggaGGATCCTGAAAGAGGCAGCAAAAC | SEQ ID NO: 74 |
| BP2919 3' For | ggaGGATCCCCGGCGAAACAGCACGTA | SEQ ID NO: 75 |
| BP2919 3' Rev | cccAAGCTTAGTTCGAAGCTGGCATTG | SEQ ID NO: 76 |
| BP3015 5' For | ccgGAATTCTTGCCGATATCGGTTTTC | SEQ ID NO: 77 |
| BP3015 5' Rev | ggaGGATCCTTGCATCCTGTTATTTGA | SEQ ID NO: 78 |
| BP3015 3' For | ggaGGATCCGTTAAACTGGATCGTTTC | SEQ ID NO: 79 |
| BP3015 3' Rev | cccAAGCTTTCGAAGCCGAATTCGTTA | SEQ ID NO: 80 |
| BP1017 5' For | ccgGAATTCAGCAGATGCGCCAGATCA | SEQ ID NO: 81 |
| BP1017 5' Rev | ggaGGATCCTTGCGTCGGTCTTGCCCT | SEQ ID NO: 82 |
| BP1017 3' For | ggaGGATCCTTCGGCGTATTGCAGTTC | SEQ ID NO: 83 |
| BP1017 3' Rev | cccAAGCTTTGAGTACCTGCCTATCGT | SEQ ID NO: 84 |

It will be understood that the invention has been described by way of example only and modifications may be made whilst remaining within the scope and spirit of the invention.

[1] WO2006/046143.
[2] Berlanda Scorza et al. (2008) *Mol Cell Proteomics* 7:473-85.
[3] European patent 0011243.
[4] Fredriksen et al. (1991) *NIPH Ann.* 14(2):67-80.
[5] WO2004/019977.
[6] Hozbor et al. (1999) *Curr Microbiol* 38:273-8.
[7] Tan et al. (2010) *N Engl J Med.* 362(16):1511-20.
[8] Koeberling (2008) *J Infect Dis.* 198(2):262-70.
[9] Uehara T. et al., The EMBO Journal (2010) 29, 1412-1422

[10] Bernadac A., et al. (1998) Journal of Bacteriology 180 (18): 4872-4878
[11] WO2002/062378
[12] Rawlings et al (2006) Nucleic Acids Res. January 1; 34:D270-2
[13] Kessler et al In A. J. Barrett. N. D. Rawlings, and J. F. Woessner (ed.). Handbook of proteolytic enzymes 1998, p. 1476-1478 1st ed. Academic Press, London, United Kingdom
[14] Hogg et al (2007) Genome Biology 8:R103.
[15] Needleman & Wunsch (1970) J. Mol. Biol. 48, 443-453.
[16] Rice et al. (2000) Trends Genet 16:276-277.
[17] WO02/09746.
[18] WO01/09350.
[19] WO02/062378.
[20] WO2004/014417.
[21] Heterologous Gene Expression in E. coli: Methods and Protocols (Method in Moleclar Biology) (eds. Evans & Xu) Humana Press 2010 (ISBN 161737%62).
[22] WO2010/010983
[23] WO2011/161551
[24] Anogv et al. (2008) PLoS ONE 3(5):e2189
[25] WO02/09643.
[26] Katial et al. (2002) Infect. Immun. 70:702-707.
[27] WO2011/036562
[28] WO2004/019977.
[29] European patent 0011243.
[30] Fredriksen et al. (1991) NIPH Ann. 14(2):67-80.
[31] WO01/91788.
[32] WO2005/004908.
[33] Gennaro (2000) Remington: The Science and Practice of Pharmacy. 20th edition, ISBN: 0683306472.
[34] Vaccine Design (1995) eds. Powell & Newman. ISBN: 030644867X. Plenum.
[35] WO90/14837.
[36] Podda & Del Giudice (2003) Expert Rev Vaccines 2:197-203.
[37] Podda (2001) Vaccine 19: 2673-2680.
[38] Vaccine Adjuvants: Preparation Methods and Research Protocols (Volume 42 of Methods in Molecular Medicine series). ISBN: 1-59259-083-7. Ed. O'Hagan.
[39] U.S. Pat. No. 5,057,540.
[40] Niikura et al. (2002) Virology 293:273-280.
[41] Lenz et al. (2001) J Immunol 166:5346-5355.
[42] Pinto et al. (2003) J Infect Dis 188:327-338.
[43] Gerber et al. (2001) J Virol 75:4752-4760.
[44] WO03/024480.
[45] WO03/024481.
[46] Gluck et al. (2002) Vaccine 20:B10-B16.
[47] Meraldi et al. (2003) Vaccine 21:2485-2491.
[48] Pajak et al. (2003) Vaccine 21:836-842.
[49] Krieg (2003) Nature Medicine 9:831-835.
[50] McCluskie et a. (2002) FEMS Immunology and Medical Microbiology 32:179-185.
[51] WO98/40100.
[52] U.S. Pat. No. 6,207,646.
[53] U.S. Pat. No. 6,239,116.
[54] U.S. Pat. No. 6,429,199.
[55] Schellack et al. (2006) Vaccine 24:5461-72.
[56] Johnson et a. (1999) Bioorg Med Chem Lett 9:2273-2278.
[57] Evans et al. (2003) Expert Rev Vaccines 2:219-229.
[58] Beignon et al. (2002) Infect Immun 70:3012-3019.
[59] Pizza et al. (2001) Vaccine 19:2534-2541.
[60] Pizza et al. (2000) Int J Med Microbiol 290:455-461.
[61] Scharton-Kersten et al. (2000) Infect Immun 68:5306-5313.
[62] Ryan et al. (1999) Infect Immun 67:6270-6280.
[63] Partidos et a. (1999) Immunol Lett 67:209-216.
[64] Peppoloni et a. (2003) Expert Rev Vaccines 2:285-293.
[65] Pine et al. (2002) J Control Release 85:263-270.
[66] WO99/40936.
[67] WO99/44636.
[68] Singh et al. (2001) J Cont Release 70:267-276.
[69] WO99/27960.
[70] U.S. Pat. No. 6,090,406.
[71] U.S. Pat. No. 5,916,588.
[72] EP-A-0626169.
[73] WO99/52549.
[74] Andrianov et al. (1998) Biomaterials 19:109-115.
[75] Payne et al. (1998) Adv Drug Delivery Review 31:185-196.
[76] Stanley (2002) Clin Exp Dermatol 27:571-577.
[77] Jones (2003) Curr Opin Investig Drugs 4:214-218.
[78] WO99/11241.
[79] WO94/00153.
[80] WO98/57659.
[81] European patent applications 0835318, 0735898 and 0761231.
[82] Ogunniyi et al. (2001) Infect Immun 69:5997-6003.
[83] WO2006/110603.
[84] Mason et al. (2003) Infect Immun 71:3454-3462.
[85] Zwijnenburg et al. (2001) J Infect Dis 183:1143-6.
[86] Cheeseman M. T. et al. (2011) PLoS Genetics 7 (10): e1002336.
[87] Watson (2000) Pediatr Infect Dis J 19:331-332.
[88] Rubin (2000) Pediatr Clin North Am 47:269-285, v.
[89] Jedrzejas (2001) Microbiol Mol Biol Rev 65:187-207.
[90] Bell (2000) Pediatr Infect Dis J 19:1187-1188.
[91] Iwarson (1995) APMIS 103:321-326.
[92] Gerlich et al. (1990) Vaccine 8 Suppl:S63-68 & 79-80.
[93] Vaccines (1988) eds. Plotkin & Mortimer. ISBN 0-7216-1946-0.
[94] Del Guidice et al. (1998) Molecular Aspects of Medicine 19:1-70.
[95] Gustafsson et al. (1996) N. Engl. J. Med. 334:349-355.
[96] Rappuoli et al. (1991) TIBTECH 9:232-238.
[97] Costantino et al. (1999) Vaccine 17:1251-1263.
[98] Sutter et al. (2000) Pediatr Clin North Am 47:287-308.
[99] Zimmerman & Spann (1999) Am Fam Physician 59:113-118, 125-126.
[100] McMichael (2000) Vaccine 19 Suppl 1:5101-107.
[101] Schuchat (1999) Lancet 353(9146):51-6.
[102] WO02/34771.
[103] Dale (1999) Infect Dis Clin North Am 13:227-43, viii.
[104] Ferretti et al. (2001) PNAS USA 98: 4658-4663.
[105] Kuroda et al. (2001) Lancet 357(9264):1225-1240; see also pages 1218-1219.
[106] EP-A-0372501
[107] EP-A-0378881
[108] EP-A-0427347
[109] WO93/17712
[110] WO94/03208
[111] WO98/58668
[112] EP-A-0471177
[113] WO00/56360
[114] WO91/01146
[115] WO00/61761
[116] WO01/72337

[117] *Research Disclosure*, 453077 (January 2002)
[118] *Current Protocols in Molecular Biology* (F. M. Ausubel et al., eds., 1987) Supplement 30.
[119] Smith & Waterman (1981) *Adv. Appl. Math.* 2:482-489.
[120] Klock et al (2005) *J. Struct. Funct. Genomics*, 6:89-94
[121] Herriott, et al (1970) *J. Bacteriol.*, 101:517-524.
[122] Carlone et al (1986) *J Clin Microbiol.* 24(3): 330-332.
[123] Echenique-Rivera H, et al (2011) *PLoS Pathog. May;* 7(5)

---

The invention claimed is:

1. A pharmaceutical composition comprising (a) outer membrane vesicles from a Gram-negative bacterium in which at least one Metalloproteases of the lysostaphin-type (LytM) catalytic domain-containing protein is inactivated and (b) a pharmaceutically acceptable carrier, wherein the composition does not comprise any living and/or whole bacteria.

2. The pharmaceutical composition of claim 1, wherein the at least one LytM catalytic domain-containing protein is knocked out.

3. The pharmaceutical composition of claim 1, wherein the at least one LytM catalytic domain-containing protein comprises: an amino acid sequence with at least 95% identity to the sequence SEQ ID NO: 1, an amino acid sequence with at least 95% identity to the sequence SEQ ID NO: 3, or an amino acid sequence with at least 95% identity to the sequence SEQ ID NO: 5.

4. The pharmaceutical composition of claim 1, wherein the Gram-negative bacterium is selected from the group consisting of: non-typeable *Haemophilus* influenza (*H. influenza*), *Neisseria meningitidis* (*N. meningitidis*), and *Bordetella pertussis* (*B. pertussis*).

5. The pharmaceutical composition of claim 1, wherein the Gram-negative bacterium is non-typeable *H. influenzae*.

6. The pharmaceutical composition of claim 1, wherein the Gram-negative bacterium is not non-typeable *H. influenzae*.

7. A method of making the pharmaceutical composition of claim 1 comprising the step of admixing vesicles from a Gram-negative bacterium in which at least one LytM catalytic domain-containing protein is inactivated with a pharmaceutically acceptable carrier.

* * * * *